(12) United States Patent
Nykjær et al.

(10) Patent No.: US 8,460,657 B2
(45) Date of Patent: Jun. 11, 2013

(54) MODULATION OF THE TRPV: VPS10P RECEPTOR SYSTEM FOR THE TREATMENT OF PAIN

(75) Inventors: Anders Nykjær, Risskov (DK); Ole J. Bjerrum, Værløse (DK); Christian Bjerggaard Vægter, Lystrup (DK); Pernille Jansen, Frederikssund (DK)

(73) Assignee: H. Lundbeck A/S, Valby (DK)

( * ) Notice: Subject to any disclaimer, the term of this patent is extended or adjusted under 35 U.S.C. 154(b) by 169 days.

(21) Appl. No.: 13/000,854

(22) PCT Filed: Jun. 24, 2009

(86) PCT No.: PCT/DK2009/050143
§ 371 (c)(1), (2), (4) Date: Feb. 16, 2011

(87) PCT Pub. No.: WO2009/155932
PCT Pub. Date: Dec. 30, 2009

(65) Prior Publication Data
US 2011/0142830 A1    Jun. 16, 2011

Related U.S. Application Data

(60) Provisional application No. 61/075,627, filed on Jun. 25, 2008.

(30) Foreign Application Priority Data

Jun. 25, 2008 (DK) .................... 2008 00880

(51) Int. Cl.
*A61K 39/395* (2006.01)
*C07K 16/28* (2006.01)

(52) U.S. Cl.
USPC ............... 424/130.1; 424/133.1; 424/135.1; 424/143.1; 530/387.1; 530/388.22

(58) Field of Classification Search
None
See application file for complete search history.

(56) References Cited

FOREIGN PATENT DOCUMENTS

| WO | 2004/056385 A2 | 7/2004 |
| WO | 2007/100718 A2 | 9/2007 |
| WO | 2008/074329 A2 | 6/2008 |
| WO | 2009/132656 A2 | 11/2009 |

OTHER PUBLICATIONS

Knotkova, H. et al., Feb. 2008, Capsaicin (TRPV1 Agonist) Therapy for Pain Relief—Farewell or Revival?, Clin. J. Pain, 24(2):142-154.
Ugolini, G. et al, Feb. 20, 2007, The function neutralizing anti-TrkA antibody MNAC13 reduces inflammatory and neuropathic pain, PNAS, 104(8):2985-2990.

*Primary Examiner* — Christine J Saoud
*Assistant Examiner* — Jon M Lockard
(74) *Attorney, Agent, or Firm* — Margaret M. Buck; Mary Catherine Di Nunzio

(57) ABSTRACT

This invention relates to the use of an agent capable of binding and thus inhibit formation of a binary Vps10p-domain receptor:TrpV receptor complex, and/or formation of a further ternary Vps10p-domain receptor:TrkA:TrpV receptor complex for the preparation of a medicament for the inhibition of pain and pain signalling through said complex(es). The invention is thus beneficial in the preparation of a medicament for the treatment and/or prevention of neuropathic pain, chronic pain and acute pain. The invention furthermore relates to the identification of such agents and animal models for screening for such agents.

5 Claims, 13 Drawing Sheets

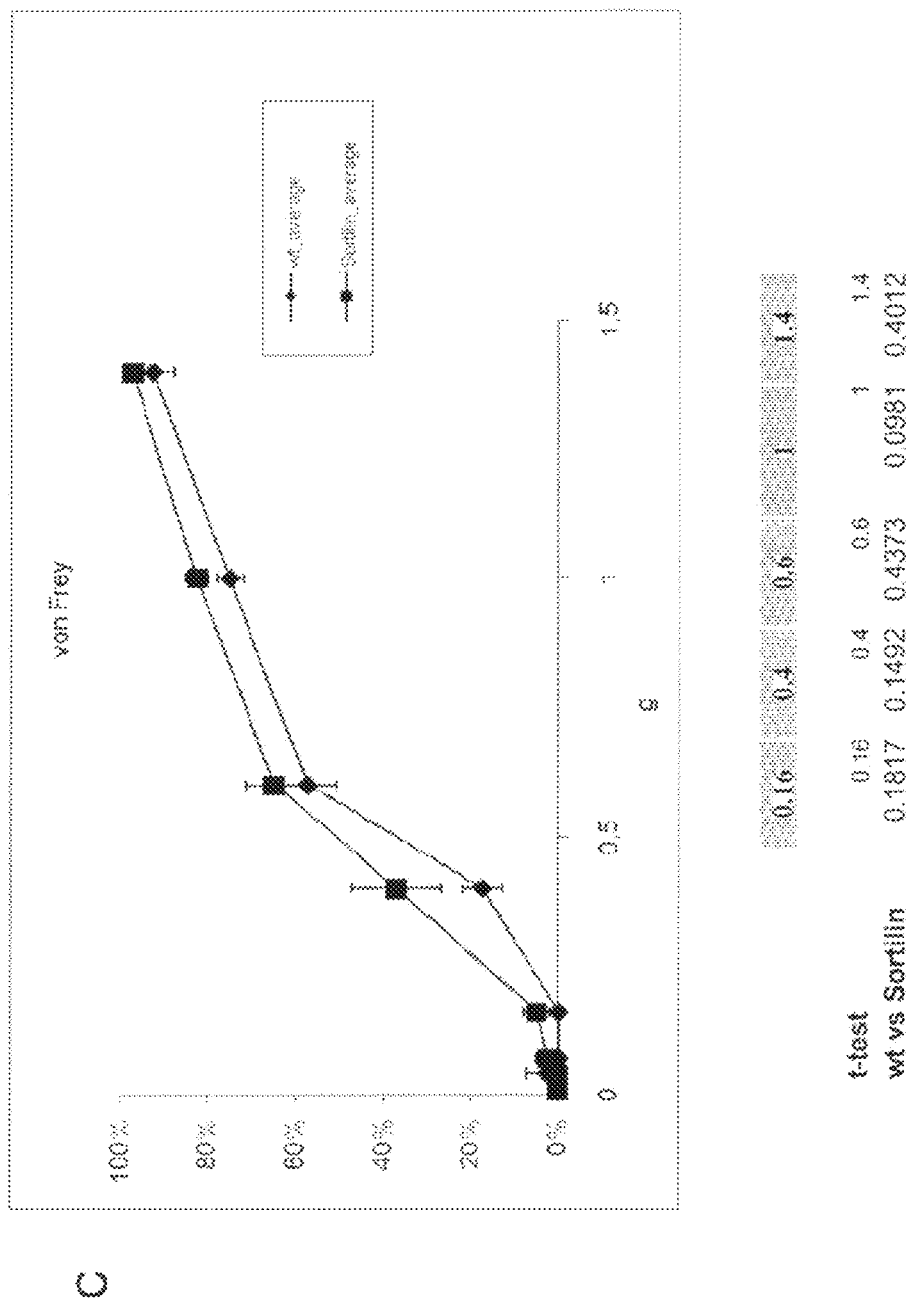

Figure 7:
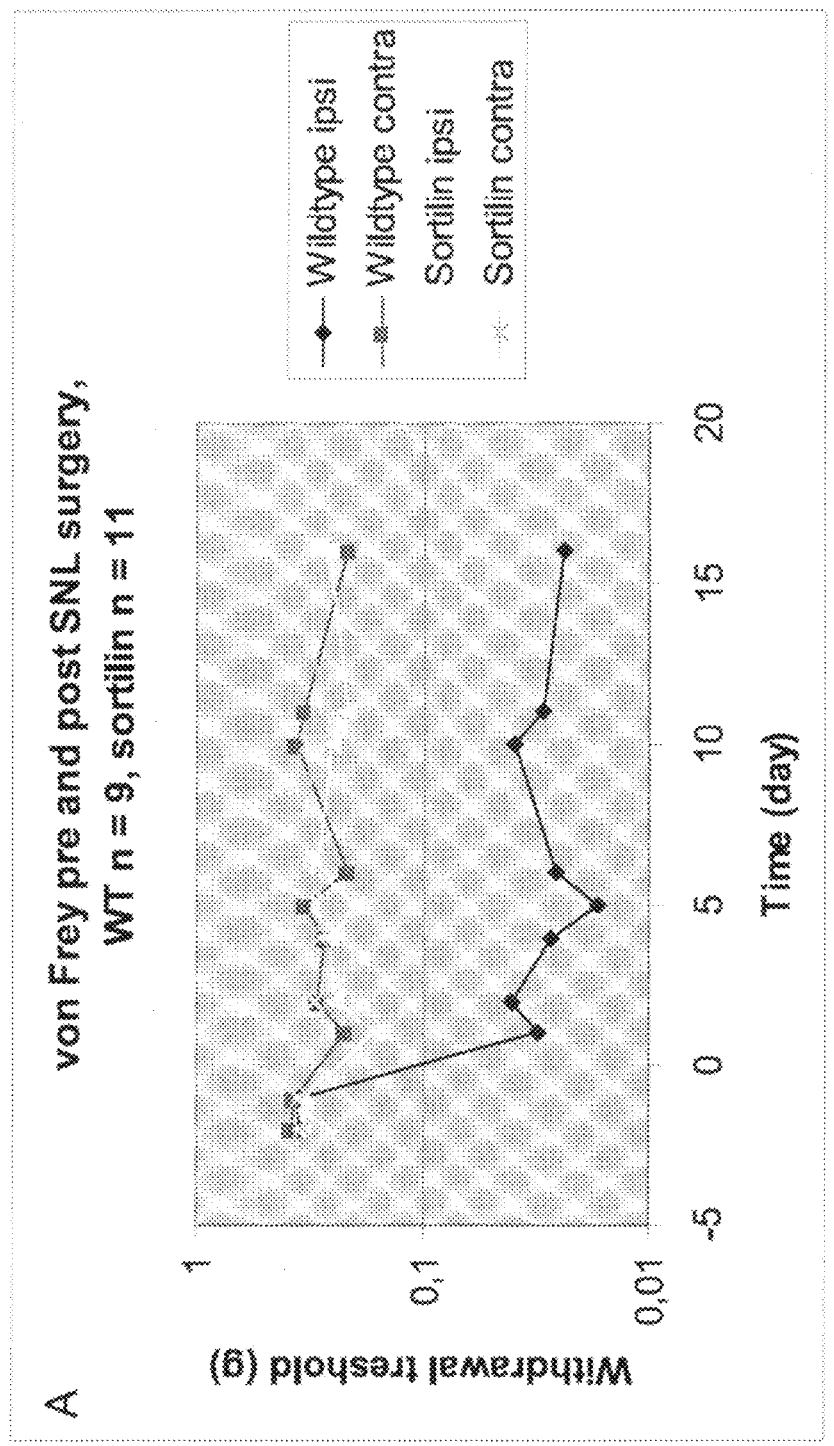

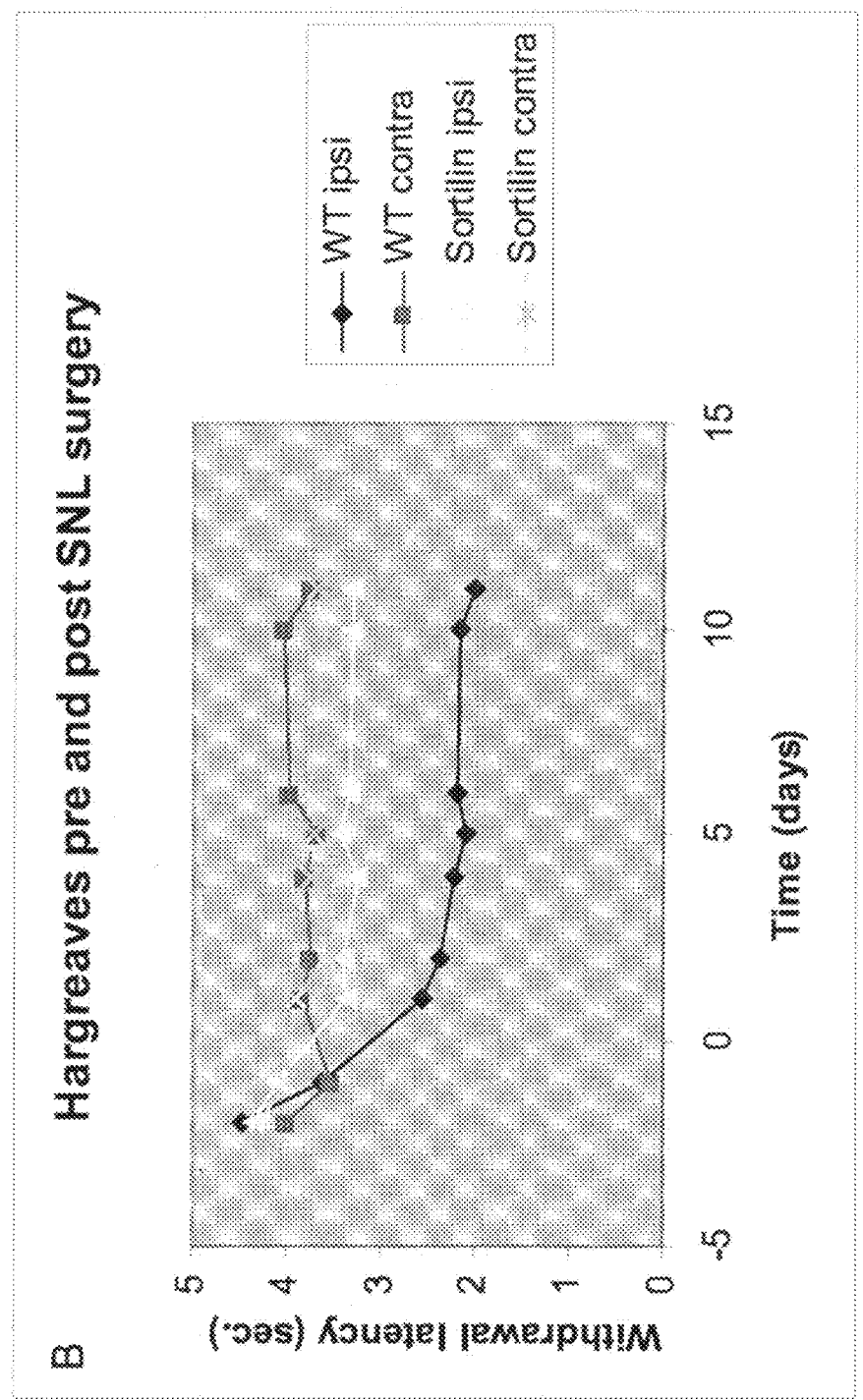
Fig. 7, continued

Competition for binding to immobilized sSortilin between 100 nM GST tagged YIL (GST-YIL) and the specified peptides.

Peptide: NT
EC50: 81nM
Sequence: pELYENKPRRPYIL
Structure:

Peptide: NT8-13
EC50: 460nM
Sequence: RRPYIL

Figure 8:
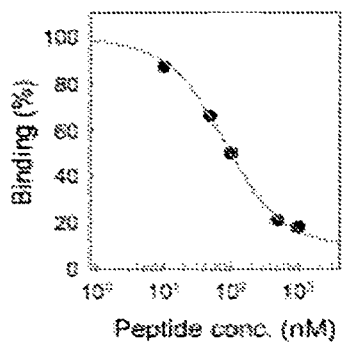
Figure 8:
Figure 8:
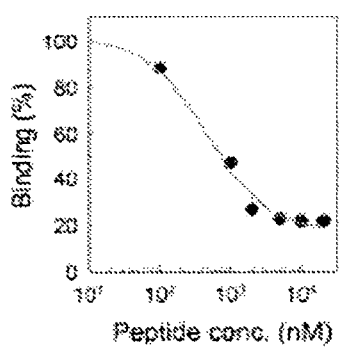
Figure 8:
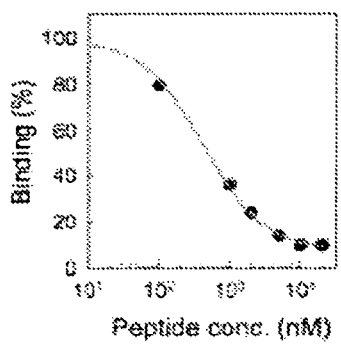
Figure 8:
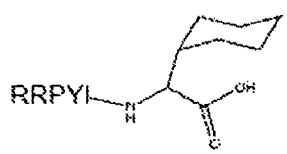

Peptide: RRPYI(chg)
EC50: 420nM
Sequence: RRPYI-cyclo-hexyl-glycine
Structure:

Competition for binding to immobilized sSortilin between 100 nM GST tagged YIL (GST-YIL) and the specified peptides.
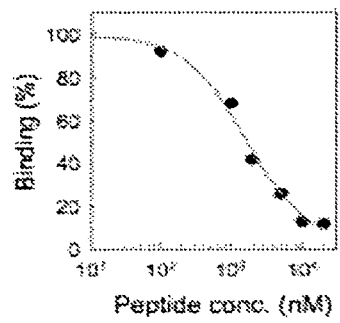
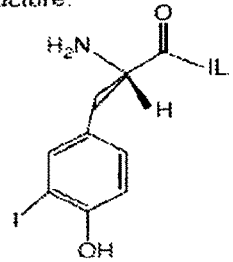
Peptide:    iodoYIL
EC50:       1675 nM
Sequence:   iodoYIL
Structure:
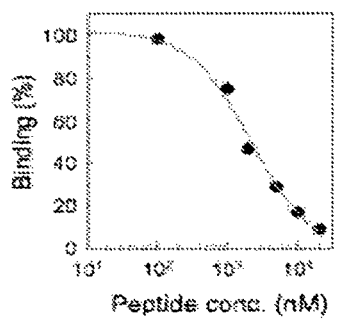
Peptide:    QIL
EC50:       1700 nM
Sequence:   QIL
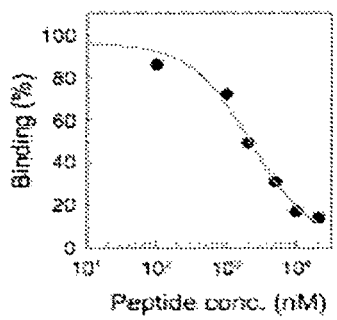
Peptide:    YCL
EC50:       2230 nM
Sequence:   YCL
Fig. 8, continued Competition for binding to immobilized sSortilin between 100 nM GST tagged YIL (GST-YIL) and the specified peptides.
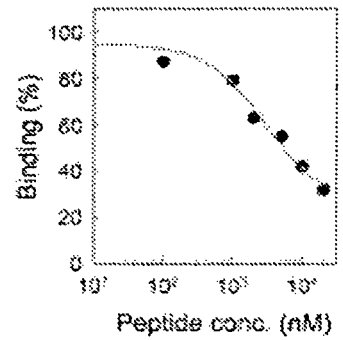
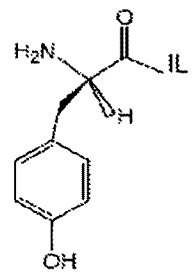
Peptide: dYIL
EC50: 3000 nM
Sequence: dYIL
Structure:
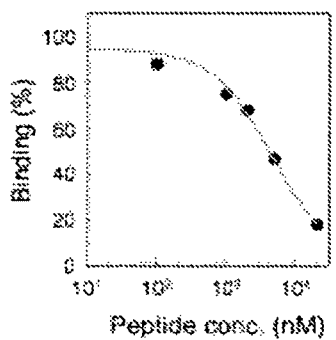
Peptide: YHL
EC50: 4580 nM
Sequence: YHL
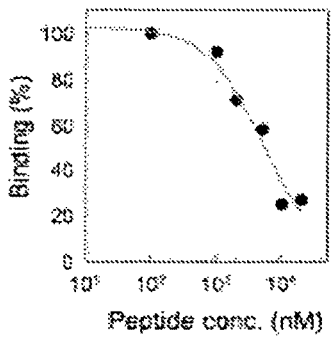
Peptide: NT69L
EC50: 5100 nM
Sequence:
Structure:
Fig. 8, continued

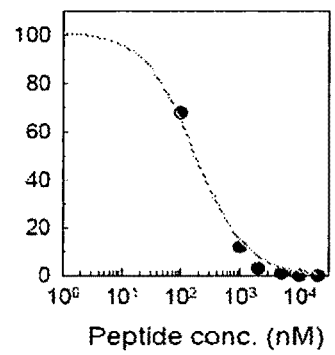
Peptide:   GST-YIL (100nM)
EC50:      200nM
Sequence:  YIL
Structure:
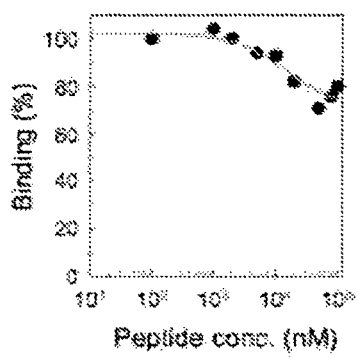
Peptide:   RRPYI(acc)
EC50:      14000 nM
Sequence:  RRPYI-1-amino-1-carboxy-cyclohexyl
Structure:
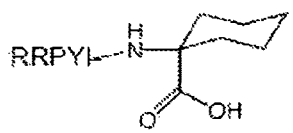
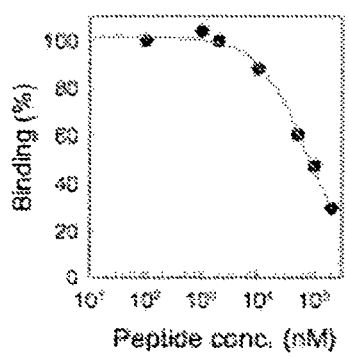
Peptide:   RRPYI(nMe)L
EC50:      68000 nM
Sequence:  RRPYI-N-methyl-Leucine
Structure:
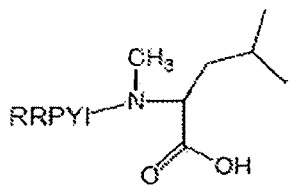
Fig. 8, continued

MODULATION OF THE TRPV: VPS10P RECEPTOR SYSTEM FOR THE TREATMENT OF PAIN

CROSS-REFERENCE TO RELATED APPLICATIONS

The present application is a §371 U.S. National Stage Application of International Application No. PCT/DK2009/050143, filed Jun. 24, 2009, which claims the benefit of priority under 35 U.S.C. §119(e) of U.S. Provisional Application No. 61/075,627, filed Jun. 25, 2008, and under 35 U.S.C. §119(a)-(d) of Danish Patent Application No. PA200800880, filed Jun. 25, 2008. Each of these applications is hereby incorporated by reference in its entirety.

This application contains a Sequence Listing, submitted in electronic form as filename Sequence_listing_0718-US-PCT, of size 91,287 bytes, created on Dec. 22, 2010. The sequence listing is hereby incorporated by reference in its entirety.

All patent and non-patent references cited in the application, or in the present application, are hereby incorporated by reference in their entirety.

FIELD OF INVENTION

The present invention relates to field of analgesia or pain relief. Specifically, the invention relates to the use of an agent for the preparation of a medicament for the treatment of pain including chronic pain and acute pain, wherein said agent is capable of binding to an entity of a pain signalling complex, wherein said complex is a binary Vps10p-domain receptor:TrpV receptor complex, and/or a ternary complex between the binary Vps10p-domain receptor:TrpV receptor complex and a third entity, such as, but not limited to TrkA receptor, thus forming a Vps10p-domain receptor:TrpV receptor:TrkA receptor ternary complex. Accordingly, the invention relates to an agent capable of inhibiting formation of said complex.

BACKGROUND OF INVENTION

Acute pain and chronic pain differ in their etiology, pathophysiology, diagnosis and treatment. Acute pain is self-limiting and serves a protective biological function by acting as a warning of on-going tissue damage. It is a symptom of a disease process experienced in or around the injured or diseased tissue. Acute pain is nociceptive in nature, and occurs secondary to chemical, mechanical and thermal stimulation of A-delta and C-polymodal pain receptors.

Chronic pain, on the other hand, serves no protective biological function. Rather than being the symptom of a disease process, chronic pain is itself a disease process. Chronic pain is unrelenting and not self-limiting and as stated earlier, can persist for years and even decades after the initial injury. Chronic, non-malignant pain is predominately neuropathic in nature and involves damage either to the peripheral or central nervous systems. Following a peripheral nerve injury (eg. crush, stretch, or axotomy) sensitization occurs which is characterized by spontaneous activity by the neuron, a lowered threshold for activation and increased response to a given stimulus.

Neuropathic pain, which is pain initiated or caused by a primary lesion or dysfunction in the nervous system are estimated to have a prevalence in USA of 1.5%, meaning in all 4 million people is affected by the conditions [1].

It manifests itself as a chronic state of hyperexcitability in the part of the nervous system transmitting the pain. Special pain receptors exist the so called nociceptors collected in the transient receptor potential receptor superclass Trp. They include the temperature sensitive vanilloid receptors (TrpV), the acid sensitising ion channels and mechano receptors [2].

Far from all lesion or diseases in the nervous system give rise to neuropathic pain. This variation is due to a genetic predisposition [3]. Thus about 8% of conventional operations where nerves inevitable is cut results in chronic pain conditions related to the scar region [4].

Pain is classified in nociceptive-, inflammatory- and neuropathic pain [5]. The first caused by a noxious stimulus is of short duration, the inflammatory pain is longer lasting and is provoked by the inflammatory mediators of the disease process which lower the threshold for pain perception. The threshold normalises when the inflammation is healed. In case of neuropathic pain, the lowered threshold induced by the injury in the affected region does not return to normal, it is so to speak irreversible set to a lower threshold than normal. This means that a stimulus not causing pain in a healthy person will give rise to pain sensation in the affected area in a patient. If a stimuli below what a normal person may sense at all is felt painful, it is called allodynia. Hyperalgesia is used to characterize the increased intensity of the pain sensation that a neuropathic person experience when a "normal" painful stimulus is applied [6].

No causal cure exists today for the neuropathic pain conditions. Only insufficient pain relieve can be offered by the healthcare system [1,7]. For the classical analgesics like opioids and non-steroidal anti-inflammatory drugs the dose-response curve is shifted to the right, meaning that much larger dose is needed for pain relief [8,9]. Anaesthetics of $Na^+$ channel blockers like carbamazepine, lamotrigine and lidocain show effect when given systematically but they produce severe adverse effects [10,11]. Treatment with anticonvulsants like gabapentin which works by decreasing the $Ca^{2+}$ influx in neurons has proven effective to dampen the pain intensity, but not to neutralise it completely. Tricyclic antidepressants mediate their effect through a range of transmitter systems e.g. the serotonergic and noradrenergic ones. They are acting both centrally and in the periphery. They are effective but the adverse effect profile is not attractive [12].

Thus there is an urgent need for drugs that modulate/interfere specifically with the molecular processes that regulate the threshold level in the affected nerve tissue to avoid the initiation or development of the processes leading to the lower threshold level for pain. Another mechanism could be constantly to suppress the molecular events that keep the threshold at the lower mode.

Analgesia

If better drugs have to be developed it is necessary to address targets that are central to the pain generation through initiation and regulation of the pain threshold level [3].

The sensitization of the pain threshold level that takes place through inflammation and involve a long row of mediators—the so called the inflammatory soup, which among others include serotonin, histamine, prostaglandins, bradykinin, substance P, calcitonin gene related peptide (CGRP), nerve growth factor (NGF) and various cytokines. In relation to nerve injury the neurotrophin NGF may be particularly important although other mediators may also participate. NGF is a member of the neurotrophin family that comprises NGF, BDNF, NT-3 and NT-4. The neurotrophins can interact with the 'non-selective' receptor $p75^{NTR}$, as well as their cognate tyrosine receptor kinase; NGF binds preferentially to tyrosine receptor kinase A (TrkA); BDNF and NT4 to TrkB; and neurotrophin 3 (NT3) to TrkC. These interactions have generally been considered to be of high affinity. However, in reality, the binding of NGF to TrkA, and of BDNF to TrkB, is of low affinity, but it can be regulated by receptor dimerization, structural modifications or association with the p75$^{NTR}$. The p75 receptor can bind to each neurotrophin, and also acts as a co-receptor for Trk receptors, sortilin and other Vps10p-domain receptors (cf. FIG. 1).

Once NGF binds, a TrkA two stages event can take place: First, at the surface of sensory neurons, TrkA physically interacts with TrpV1, a member of a large family of calcium-permeable nonselective cation channels, that is implicated in development of thermal hyperalgesia induced by tissue injury and inflammation, and in chronic and neuropathic pain [13]. Binding of NGF to TrkA strongly potentiates calcium-influx by TrpV1 and the induction of pain. Second, NGF binding to TrkA and p75NTR also results in retrograde transport of the complex back to the cell body of the neurons where it modulates the activity and transcription of proteins important for neuronal survival and differentiation, but also of enzymes and ion-channels involved in the nociceptive transmission [3,14]. Also microglia may play a role in this activation [15].

After injury of a nerve, the amount of NGF decreases in the sensory neurons, but after a while it increases again due to secretion from Schwann cells, macrophages and likely also by the neurons themselves. This stimulates the regeneration of the nerve.

Further it has been shown that proNGF, a precursor form of NGF, interacts with a heteromer receptor complex consisting of p75$^{NTR}$ and Sortilin thus forming a ternary complex. As opposed to the trophic activities elicited by mature NGF, proNGF induces apoptosis by the formation of said ternary complex via p75$^{NTR}$ and Sortilin, unless proNGF is converted into its mature form [24].

Earlier [16] related severe pain sensory neuropathies to the presence of the TrkA gene in mice. Arrett et al. (2007) [17] examined the expression of the proNGF, sortilin and p75NTR in the dorsal root ganglion. They found that a subpopulation of neurons coexpressed sortilin and p75$^{NTR}$ and that nerve injury induced a severe loss of a subpopulation of the small p75$^{NTR}$-sortilin coexpressing neurons.

Thus, these observations points to the relation between the development and maintenance of chronic and neuropathic pain conditions.

In the example section of this patent application, further experimental evidence is demonstrated for how an agent can be designed to specifically interact with the signalling cascade involved in the development of the neuropathic pain conditions described herein above, through interruption of the formation of the receptor complex.

The Vps10p-domain Receptor Family

The present inventors have studied the effect of modulation formation of a pain signalling complex, wherein said complex comprises a Vps10p-domain receptor:TrpV receptor binary complex or a Vps10p-domain receptor:TrpV receptor ternary complex, such as a complex between a Vps10p-domain receptor, TrkA, and a TrpV receptor.

The members of the Vps10p-domain receptors are Sortilin, SorLA, SorCS1, SorCS2 and SorCS3.

Sortilin

Sortilin, the archetypal member of the Vps10p-domain receptor family is occasionally also referred to as Neurotensin receptor 3 (NTR3), Glycoprotein 95 (Gp95) or 100 kDa NT receptor. Human Sortilin is accessed in Swiss Prot under ID No. Q99523.

Sortilin, (SEQ ID NO. 1) is a type I membrane receptor expressed in a number of tissues, including the brain, spinal cord, testis, liver and skeletal muscle [18-19]. Sortilin belongs to a family of receptors comprising Sortilin, SorLA [20], SorCS1, SorCS2 and SorCS3.

All the receptors in this family share the structural feature of an approximately 600-amino acid N-terminal domain with a strong resemblance to each of the two domains which constitute the luminal portion of the yeast sorting receptor Vps10p [21]. The Vps10p-domain (Vps10p-D) that among other ligands binds neurotrophic factors and neuropeptides [22-26], constitutes the entire luminal part of Sortilin (sSortilin) and is activated for ligand binding by enzymatic propeptide cleavage. Sortilin is a multifunctional type-1 receptor capable of endocytosis as well as intracellular sorting [22, 23], and as shown recently, it also engages in signaling by triggering proneurotrophin-induction of p75$^{NTR}$-mediated neuronal apoptosis [24, 25, 30, 31]. Sortilin is synthesized as a proprotein, which is converted to mature Sortilin by enzymatic cleavage and removal of a short N-terminal propeptide. Only the mature receptor binds ligands and interestingly, all its known ligands, e.g. Neurotensin (NT), lipoprotein lipase, the proforms of nerve growth factor-β (proNGF) and brain derived neurotrophic factor (proBDNF), receptor associated protein (RAP), and its own propeptide, compete for binding [23-25, 28], indicating that the diverse ligands target a shared or partially shared binding site. NT is a tridecapeptide, which binds to Sortilin, SorLA and the two G-protein coupled receptors NTR1 and NTR2 [22, 32-34].

SorLA

Sorting protein-related receptor abbreviated SorLA (Swiss prot ID no Q92673), also known as LR11, is a 250-kDa type-1 membrane protein and the second member identified in the Vps10p-domain receptor family SorLA, like sortilin, whose lumenal domain consists of a Vps10p domain only, is synthesized as a proreceptor that is cleaved by furin in late Golgi compartments. It has been demonstrated [33] that the truncation conditions the Vps10p domain for propeptide inhibitable binding of neuropeptides and the receptor-associated protein. In transfected cells, about 10% of full-length SorLA is expressed on the cell surface capable mediating endocytosis. The major pool of receptors is found in late Golgi compartments, and interaction with newly synthesized ligands has been suggested.

SorCS1-3

SorCS1 (Swiss prot ID no Q8WY21), SorCS2 (Swiss prot ID no Q96PQ0) and SorCS3 (Swiss prot ID no Q9UPU3) constitute a subgroup of mutually highly similar proteins containing both a Vps10p-D and a leucine-rich domain bordering the transmembrane domain [26, 38].

TrkA

Neurotrophic tyrosine kinase, receptor, type 1, also known as NTRK1 (Swiss prot ID no P04629) and normally referred to as TrkA (Tropomyosin-Related Kinase A) is a member of the neurotrophic tyrosine kinase receptor (NTKR) family. TrkA is the high affinity catalytic receptor for the neurotrophin, Nerve Growth Factor, or "NGF". As such, it mediates the multiple effects of NGF, which includes neuronal differentiation and survival: upon NGF binding, TrkA dimerize and autophosphorylates which results in activation of downstream members of the MAPK pathway.

The presence of TrkA leads to cell differentiation and may play a role in specifying sensory neuron subtypes. Hence mutations in this gene have also been associated with congenital insensitivity to pain [39,40,41].

TrkA is known to associate with TrpV1 and this interaction is essential for NGF-mediated potentiation of TrpV1 activity [42].

Known agents with antagonistic properties include the kinase domain inhibitor K252A.

TRPV1

The Transient receptor potential vanilloid 1, TrpV1 (Swiss prot ID no Q8NER1), also known as the vanniloid receptor or the capsaicin receptor, is a nonselective ligand-gated cation channel that may be activated by a wide variety of exogenous and endogenous stimuli, including heat greater than 43° C., low pH, anandamide, N-arachidonoyl-dopamine, and capsaicin. TRPV1 receptors are highly expressed in a subset of dorsal root ganglia neurons, show a much higher sensitivity to heat than most ion channels and are involved in the transmission and modulation of pain, as well as the integration of diverse painful stimuli [43,44].

TRPV1 antagonist agents include AMG517 (highly selective was dropped out of clinical trials due to the undesirable side effects), SB-705498 and capsazepine.

SUMMARY OF THE INVENTION

The invention in a main aspect relates to the use of at least one agent capable of binding to an entity of the:
a. Vps10p-domain receptor:TrpV receptor binary complex, and/or
b. Vps10p-domain receptor:TrkA:TrpV receptor ternary complex thus inhibiting formation of said complex, for the preparation of a medicament for the treatment of pain in a mammal.

In another main aspect, the present invention relates to the use of at least one agent capable of inhibiting formation of the:
a. Vps10p-domain receptor:TrpV receptor binary complex, and/or
b. Vps10p-domain receptor:TrkA:TrpV receptor ternary complex,
for the preparation of a medicament for the treatment of pain in a mammal.

In another main aspect, the present invention relates to at least one agent capable of inhibiting formation of the:
a. Vps10p-domain receptor:TrpV receptor binary complex, and/or
b. Vps10p-domain receptor:TrkA:TrpV receptor ternary complex,
for use in a method of treatment of pain in a mammal.

In yet another main aspect, the present invention relates to a method of treatment of pain, said method comprising administering to a mammal in need thereof, at least one agent capable of inhibiting formation of the:
a. Vps10p-domain receptor:TrpV receptor binary complex, and/or
b. Vps10p-domain receptor:TrkA:TrpV receptor ternary complex.

In another aspect the present invention relates to an in vitro method for screening for the candidate agent or candidate agent, as defined herein above comprising the steps of:
  i. providing a Vps10p-domain receptor and a TrpV receptor, or
  ii. providing a Vps10p-domain receptor and a TrpV receptor and a TrkA receptor, and
  iii. providing a library of potential agents, and
  iv. providing an assay for measuring the binding of a first entity Vps10p-domain receptor to a second entity TrpV receptor, or
  v. providing an assay for measuring the binding of a first entity TrpV receptor to a second entity Vps10p-domain receptor, or
  vi. providing an assay for measuring the binding of a first entity TrpV receptor to a second entity (Vps10p-domain receptor:TrkA receptor) binary complex, or
  vii. providing an assay for measuring the binding of a first entity (Vps10p-domain receptor:TrkA receptor) binary complex to a second entity TrpV receptor, or
  viii. providing an assay for measuring the binding of a first entity Vps10p-domain receptor to a second entity (TrpV:TrkA receptor) binary complex, or
  ix. providing an assay for measuring the binding of a first entity (TrpV:TrkA receptor) binary complex to a second entity Vps10p-domain receptor, or
  x. providing an assay for measuring the binding of a first entity TrkA receptor to a second entity (TrpV:Vps10-p domain receptor) binary complex, or
  xi. providing an assay for measuring the binding of a first entity (TrpV:Vps10p-domain receptor) binary complex to a second entity TrkA receptor, and
  xii. adding the library of potential agents to be tested to the assay selected from iv to xi, and
  xiii. determining the amount of said first entity to said second entity, and
  xiv. comparing the amount determined in step xiv) with an amount measured in the absence of the agent to be tested,
  xv. wherein the difference in the two amounts identifies an agent which alters the binding of the first entity to the second entity.

In another aspect the invention relates to a method for determining the degree of inhibition of the agent or candidate agent as defined herein above, on activity of a Vps10p-domain receptor in a cell culture expressing said receptor, wherein said Vps10p-domain receptor comprises an amino acid sequence having at least 60% sequence identity to SEQ ID NO. 1, SEQ ID NO. 2, SEQ ID NO. 3, SEQ ID NO. 4 or SEQ ID NO. 5, said method comprising the steps of:
a. providing a cell culture expressing a Vps10p-domain receptor, and
b. providing an agonist of the Vps10p-domain receptor, and
c. providing a library of potential agents, and
d. providing an assay for determination of binding to, internalisation of and signalling through, a Vps10p-domain receptor, said assay comprising
e. adding the library of potential agents to be tested c) to the cell culture a), in the presence of the agonist b), and
f. determining
  i. the amount of agent bound to the Vps10p-domain receptor, and/or
  ii. the amount of agent internalised by the Vps10p-domain receptor, and/or
  iii. the degree of signalling through the Vps10p-domain receptor, and
g. comparing the amount determined in step f) with an amount measured in the absence of the agents to be tested,
h. wherein the difference in the two amounts identifies an agent
  i. capable of binding to a Vps10p-domain receptor, and/or
  ii. capable of inhibiting signalling through a Vps10p-domain receptor, and/or
  iii. capable of inhibiting internalisation of an agonist of said Vps10p-domain receptor.

In yet another aspect the present invention relates to a method for determining the degree of inhibition of the agent or candidate agent as defined herein above, on activity of a TrpV receptor in a cell culture expressing said receptor, wherein said TrpV receptor comprises an amino acid sequence having at least 70% sequence identity to SEQ ID NO. 6, SEQ ID NO. 7, SEQ ID NO. 8 or SEQ ID NO. 9, said method comprising the steps of:

a. providing a cell culture expressing a TrpV receptor, and
b. providing an agonist of the TrpV receptor, and
c. providing a library of potential agents, and
d. providing an assay for determination of binding to a TrpV receptor, said assay comprising
e. adding the library of potential agents to be tested c) to the cell culture a), in the presence of the agonist b), and
f. determining the amount of agent bound to the TrpV receptor and
g. comparing the amount determined in step f) with an amount measured in the absence of the agent to be tested,
h. wherein the difference in the two amounts identifies an agent capable of binding to a TrpV receptor.

In another aspect the present invention relates to a method for determining the degree of inhibition of an agent or a candidate agent as defined herein above, on activity of a TrkA receptor in a cell culture expressing said receptor, wherein said TrkA receptor comprises an amino acid sequence having at least 70% sequence identity to SEQ ID NO. 10, said method comprising the steps of:
a. providing a cell culture expressing a TrkA receptor, and
b. providing an agonist of the TrkA receptor, and
c. providing a library of potential agents, and
d. providing an assay for determination of binding to a TrkA receptor, said assay comprising
e. adding the library of potential agents to be tested c) to the cell culture a), in the presence of the agonist b), and
f. determining the amount of agent bound to the TrkA receptor and
g. comparing the amount determined in step f) with an amount measured in the absence of the agent to be tested, wherein the difference in the two amounts identifies an agent capable of binding to a TrkA receptor.

In a further aspect the present invention relates to a method for determining the degree of inhibition of an agent or candidate agent as defined herein above, on activity of a Vps10p-domain receptor in a cell culture expressing said receptor and with a cell culture lacking expression of said receptor, said method comprising the steps of:
a. providing a cell culture expressing a Vps10p-domain receptor, and
b. providing a cell culture not expressing a Vps10p-domain receptor, and
c. optionally providing a cell culture overexpressing a Vps10p-domain receptor
d. providing an agonist for pain sensation of the Vps10p-domain receptor, and
e. providing a library of potential agents, and
f. providing a first assay comprising a) and a second assay comprising b) and optionally a third assay comprising c), and
g. adding the library of potential agents to be tested to the three assays, and
h. determining
  i. the amount of agent bound to the Vps10p-domain receptor, and/or
  ii. the amount of agent internalised by the Vps10p-domain receptor, and/or
  iii. the degree of signalling through the Vps10p-domain receptor, and
i. comparing the amount of agent determined in step g) using a) with the amount determined in g) using b) and the amount determined in g) using c),
j. wherein the difference in the amounts identifies an agent capable of
  i. binding to a Vps10p-domain receptor, and/or
  ii. inhibiting signalling through a Vps10p-domain receptor, and/or
  iii. inhibiting internalisation of an agonist of said Vps10p-domain receptor.

In yet another aspect the present invention relates to a method for determining the degree of inhibition of an agent or a candidate agent as defined herein above, on activity of a TrpV receptor in a cell culture expressing said receptor and with a cell culture lacking expression of said receptor, said method comprising the steps of:
a. providing a cell culture expressing a TrpV receptor, and
b. providing a cell culture not expressing a TrpV receptor, and
c. optionally providing a cell culture overexpressing a trpV receptor
d. providing an agonist of the TrpV receptor, and
e. providing a library of potential agents, and
f. providing a first assay comprising a) and a second assay comprising b) and optionally a third assay comprising c), and
g. adding the library of potential agents to be tested to the three assays, and
h. determining
  i. the amount of agent bound to the TrpV receptor, and/or
  ii. the degree of signalling through the TrpV receptor, and
i. comparing the amount of agent determined in step h) using a) with the amount determined in h) using b) and the amount determined in g) using c),
j. wherein the difference in the amounts identifies an agent capable of binding to a TrpV receptor, and/or inhibiting signalling through a TrpV.

In a further aspect the present invention relates to a method for determining the degree of inhibition of an agent or candidate agent, on activity of a TrkA receptor in a cell culture expressing said receptor and with a cell culture lacking expression of said receptor, said method comprising the steps of:
a. providing a cell culture expressing a TrkA receptor, and
b. providing a cell culture not expressing a TrkA receptor, and
c. optionally providing a cell culture overexpressing a TrkA receptor
d. providing an agonist of the TrkA receptor, and
e. providing a library of potential agents, and
f. providing a first assay comprising a) and a second assay comprising b) and optionally a third assay comprising c), and
g. adding the library of potential agents to be tested to the three assays, and
h. determining
  i. the amount of agent bound to the TrkA receptor, and/or
  ii. the amount of agent internalised by the TrkA receptor, and/or
  iii. the degree of signalling through the TrkA receptor, and
i. comparing the amount of agent determined in step h) using a) with the amount determined in h) using b) and optionally the amount determined in g) using c),
j. wherein the difference in the amounts identifies an agent capable of binding to a TrkA receptor, and/or inhibiting signalling through a TrkA.

In yet another aspect the present invention relates to a method for determining the degree of inhibition of an agent or candidate agent, on activity of a Vps10p-domain receptor in a mammal expressing said receptor with a second mammal lacking expression of said receptor and a third mammal overexpressing said receptor, said method comprising the steps of:

a. providing a mammal expressing a Vps10p-domain receptor, and
b. providing a mammal not expressing a Vps10p-domain receptor, and
c. providing a mammal overexpressing a Vps10p-domain receptor, and
d. providing an agonist for pain sensation of the Vps10p-domain receptor, and
e. providing a library of potential agents, and
f. administering said library of agents to said mammal of a), b) and c) respectively, and
g. determining the degree of pain signalling through the Vps10p-domain receptor, in each of the mammals defined in a), b) and c), using
   i. von Frey test and/or
   ii. Tail immersion assay and/or
   iii. Hot plate test, and
h. comparing the degree of pain signalling in step g) using a) with the degree determined in g) using b) with the degree determined in g) using c), wherein the difference in the degree of inhibition identifies an agent capable of binding to a Vps10p-domain receptor, inhibiting signalling through a Vps10p-domain receptor.

In yet another aspect the present invention relates to a method for determining the degree of inhibition of an agent or candidate agent as defined herein above, on activity of a TrpV receptor in a mammal expressing said receptor with a second mammal lacking expression of said receptor and a third mammal overexpressing said receptor, said method comprising the steps of:
a. providing a mammal expressing a TrpV receptor, and
b. providing a mammal not expressing a TrpV receptor, and
c. providing a mammal overexpressing a TrpV receptor, and
d. providing an agonist for pain sensation of the TrpV receptor, and
e. providing a library of potential agents, and
f. administering said library of agents to said mammal of a), b) and c) respectively, and
g. determining the degree of pain signalling through the TrpV receptor, in each of the mammals defined in a), b) and c), using von Frey test and/or Tail immersion assay and/or Hot plate test, and
h. comparing the degree of pain signalling in step g) using a) with the degree determined in g) using b) with the degree determined in g) using c), wherein the difference in the degree of inhibition identifies an agent capable of binding to a TrpV receptor and inhibiting signalling through said TrpV receptor.

In another aspect the present invention relates to a method for determining the degree of inhibition of an agent or candidate agent as defined herein above, on activity of a Vps10-p domain receptor:TrpV receptor binary complex in a mammal expressing said receptors with a second mammal lacking expression of said receptors and a third mammal overexpressing said receptors, said method comprising the steps of:
a. providing a first and a second mammal expressing both a TrpV receptor and a Vps10p-domain receptor, and
b. providing a first and a second mammal lacking expressing of a TrpV receptor and a Vps10p-domain receptor, and
c. providing a first and a second mammal overexpressing a TrpV receptor and a Vps10p-domain receptor, and
d. providing an agonist for pain sensation of the TrpV receptor and/or Vps10p-domain receptor, and
e. providing a library of potential agents capable of inhibiting signalling through a Vps10p-domain receptor:TrpV receptor binary complex, and
f. administering said library of agents to said first mammal of a), b) and c) respectively, and
g. administering placebo to said second mammal of a), b), and c), and
h. determining the degree of pain signalling through the TrpV receptor, in each of the first and second mammals defined in a), b) and c), using
   i. von Frey test and/or
   ii. Tail immersion assay and/or
   iii. Hot plate test, and
i. comparing the degree of pain signalling in the first and second mammals of step h) using a) and
j. comparing the degree of pain signalling in the first and second mammals of h) using b) and
comparing the degree of pain signalling in the first and second mammals of h) using c),
wherein the difference in the degree of inhibition of pain signalling identifies an agent capable of binding to a Vps10p-domain receptor:TrpV receptor complex and inhibiting signalling through said complex.

In an important aspect the present invention relates to a transgenic knock-out mouse in which the endogenous Vps10p-domain receptor SorCS1 and/or SorCS2 genes have been disrupted to abolish expression of a functional receptor, and wherein said mouse exhibits a reduced response towards pain stimuli relative to a non-transgenic control mouse.

In one aspect the present invention relates to a method for screening a candidate agent for the ability to reduce pain in the transgenic SorCS1-2 mouse as defined herein above comprising the steps of:
a. providing SorCS1-2 mouse as defined herein above;
b. providing wild type mouse lacking the gene disruption in SorCS1-2 as defined herein above; and
c. providing a control wild type mouse lacking the gene disruption in SorCS1-2 as defined herein above; and
d. administering to said first wild-type mouse (b) a candidate agent, and
comparing pain behaviour of said transgenic mouse of step (a) to the pain behaviour of said wild-type mouse of step (b) administered said candidate agent with to the pain behaviour of said control wild-type mouse of step (c) not administered said candidate agent; wherein a reduction in pain behaviour in said wild type mouse (b) administered said candidate agent to a level comparable with said second transgenic mouse not administered said candidate agent relatively to the control wild-type mouse (c) indicates that the candidate agent reduces pain behavior. In another main aspect the present invention relates to a transgenic mouse for conditional or obligate over-expression of Sortilin or SorCS1 or SorCS2 in neuronal tissues.

In one aspect the invention relates to a pharmaceutical composition comprising an agent as defined herein above, the activity of said agent having been determined as defined by the screening methods herein above.

In one aspect, the invention relates to a method of treatment of pain in a subject comprising administering to an individual in need thereof a therapeutically effective amount of the pharmaceutical composition as defined herein above.

In a further aspect, the present invention relates to a method for treating neuropathy by administering to an individual in need thereof a sufficient amount of the agent as defined herein.

In one aspect, the present invention relates to a kit in parts comprising:

the pharmaceutical composition as defined herein above and a medical instrument or other means for administering the pharmaceutical and instructions on how to use the kit in parts.

In another aspect, the present invention relates to an immunoconjugate comprising the antibody agent as defined herein, and a conjugate selected from the group consisting of: a cytotoxic agent such as a chemotherapeutic agent, a toxin, or a radioactive isotope; a member of a specific binding pair, such as avidin or streptavidin or an antigen.

In an important aspect the present invention relates to the use of the at least one agent as defined herein above wherein said agent is capable of inhibiting expression of a Vps10p-domain receptor or a TrpV receptor or a TrkA receptor in an animal.

In one aspect, the present invention relates to a method for marketing of a medicinal product, said product comprising at least one isolated agent, said agent being as defined herein above, and said marketing comprising the public spreading of the information that inhibition of formation of said complex has an impact on pain sensation in said subject.

OVERVIEW OF THE DRAWINGS

Figure 1:
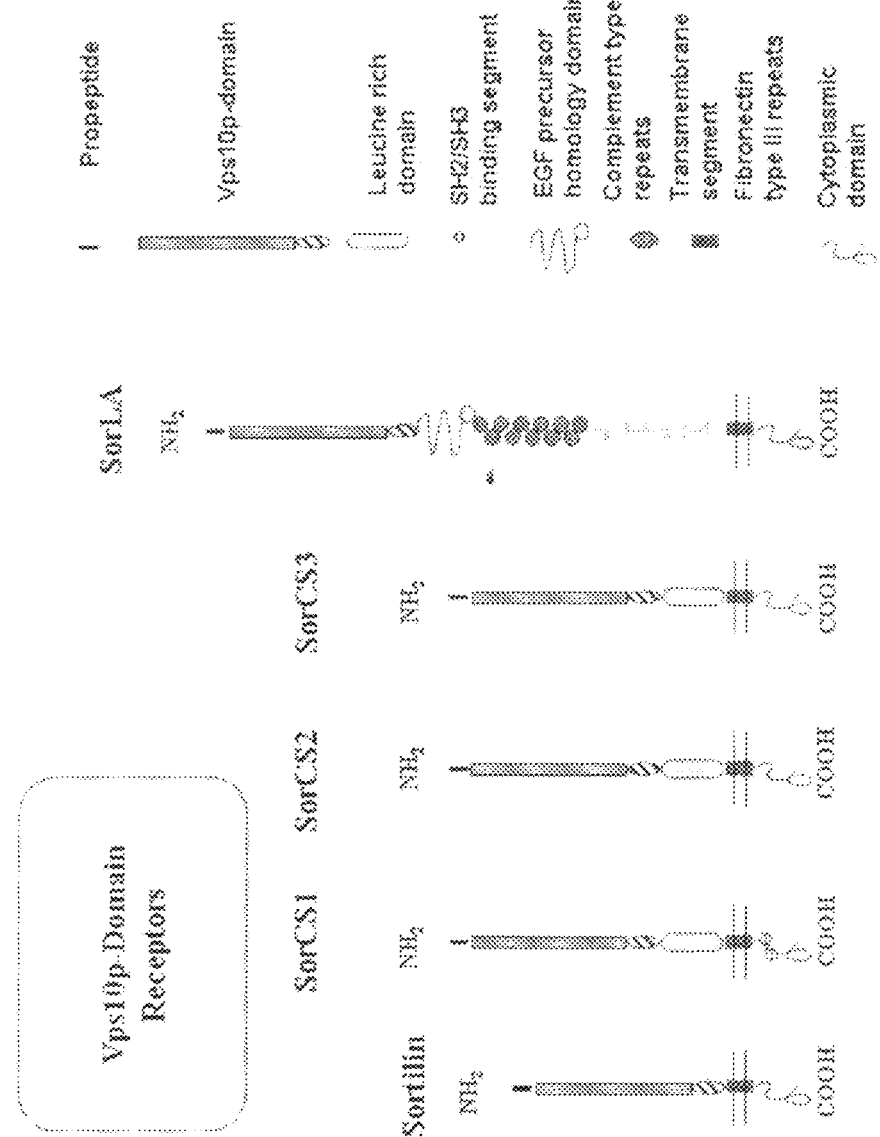
Figure 3:
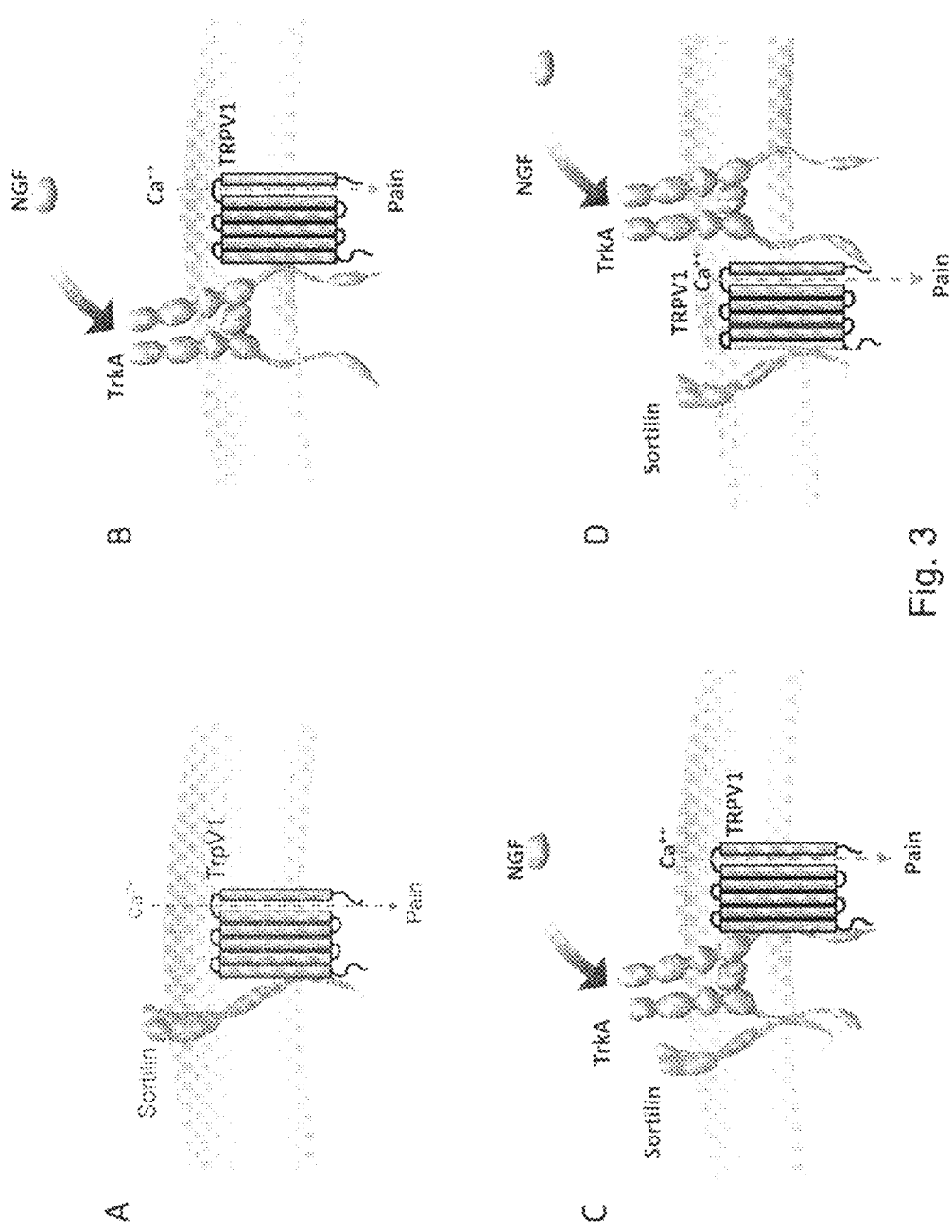
Figure 4:
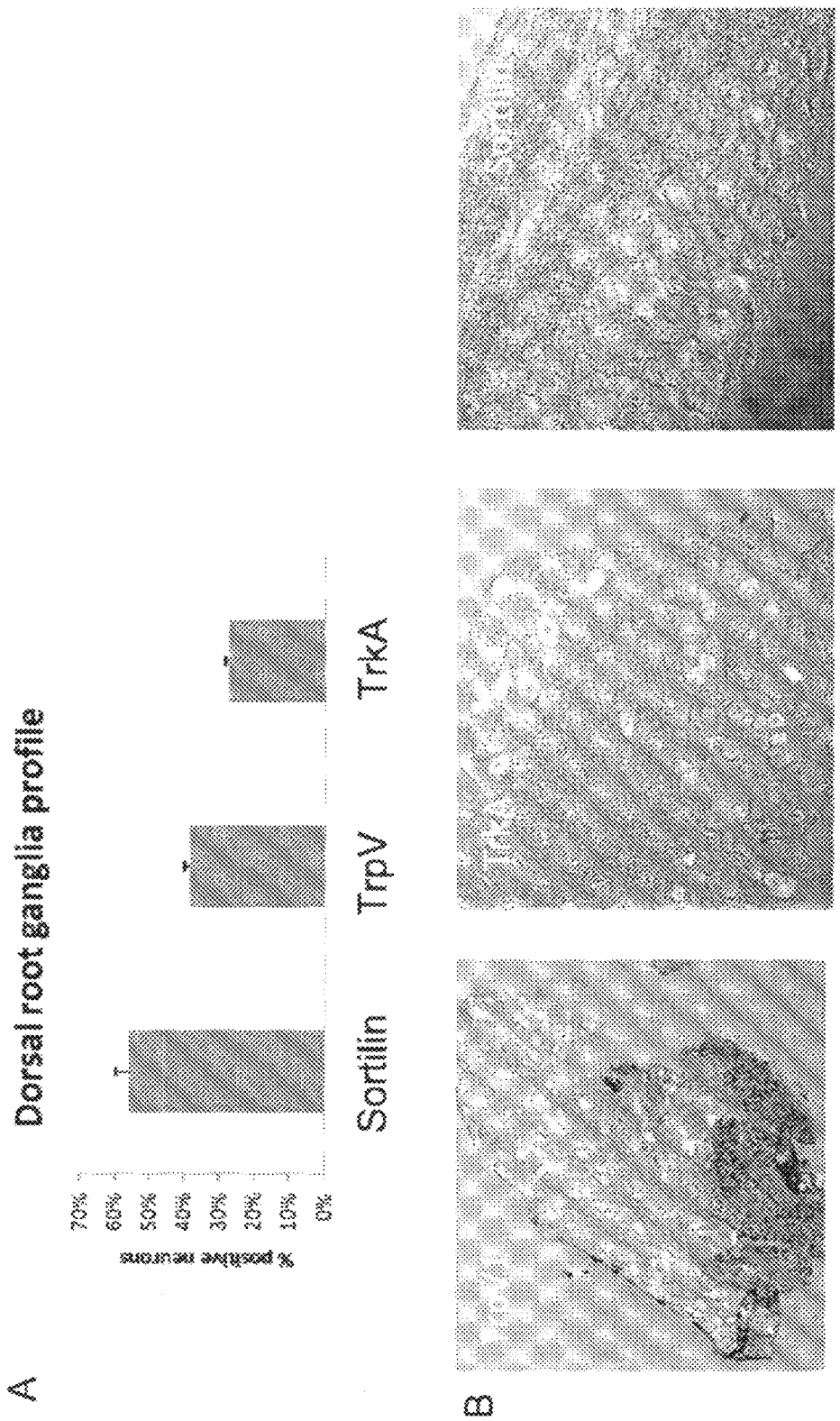

FIG. 1: Receptor overview
FIG. 2: Physical interactions of the receptors—coimmunoprecipitations.
FIG. 3: Physical interactions of the receptors—schematic
FIG. 4: Stereological and immunoflourenscence data of DRG
FIG. 5a-b: Hotplate and tail flick
FIG. 5c: von Frey
FIG. 6: Neuropathic pain in Spared Nerve Injury animal model.
FIG. 7a-b: Neuropatic pain in Spinal Nerve Ligation animal model
FIG. 8: BIACORE binding data for agents of the invention

DETAILED DESCRIPTION ON THE INVENTION

Definitions

Acute pain: Pain that comes on quickly, can be severe, but lasts a relatively short time as opposed to chronic pain Adjuvant: Any substance whose admixture with an administered immunogenic determinant/antigen increases or otherwise modifies the immune response to said determinant.

Affinity: The interaction of most ligands with their binding sites can be characterized in terms of a binding affinity. In general, high affinity ligand binding results from greater intermolecular force between the ligand and its receptor while low affinity ligand binding involves less intermolecular force between the ligand and its receptor. In general, high affinity binding involves a longer residence time for the ligand at its receptor binding site than is the case for low affinity binding. High affinity binding of ligands to receptors is often physiologically important when some of the binding energy can be used to cause a conformational change in the receptor, resulting in altered behavior of an associated ion channel or enzyme.

A ligand that can bind to a receptor, alter the function of the receptor and trigger a physiological response is called an agonist for that receptor. Agonist binding to a receptor can be characterized both in terms of how much physiological response can be triggered and the concentration of the agonist that is required to produce the physiological response. High affinity ligand binding implies that a relatively low concentration of a ligand is adequate to maximally occupy a ligand binding site and trigger a physiological response. Low affinity binding implies that a relatively high concentration of a ligand is required before the binding site is maximally occupied and the maximum physiological response to the ligand is achieved. Ligand binding is often characterized in terms of the concentration of ligand at which half of the receptor binding sites are occupied, known as the dissociation constant ($k_d$). Affinity is also the strength of binding between receptors and their ligands, for example between an antibody and its antigen.

Alcohol: A class of organic compounds containing one or more hydroxyl groups (OH). In this context a saturated or unsaturated, branched or unbranched hydrocarbon group sitting as a substituent on a larger molecule.

Alicyclic group: the term "alicyclic group" means a cyclic hydrocarbon group having properties resembling those of aliphatic groups.

Aliphatic group: in the context of the present invention, the term "aliphatic group" means a saturated or unsaturated linear or branched hydrocarbon group. This term is used to encompass alkyl, alkenyl, and alkynyl groups, for example.

Alkyl group: the term "alkyl group" means a saturated linear or branched hydrocarbon group including, for example, methyl, ethyl, isopropyl, t-butyl, heptyl, dodecyl, octadecyl, amyl, 2-ethylhexyl, and the like.

Alkenyl group: the term "alkenyl group" means an unsaturated, linear or branched hydrocarbon group with one or more carbon-carbon double bonds, such as a vinyl group.

Alkynyl group: the term "alkynyl group" means an unsaturated, linear or branched hydrocarbon group with one or more carbon-carbon triple bonds.

Amphiphil: substance containing both polar, water-soluble and nonpolar, water-insoluble groups.

Agonist: An agonist is a compound capable of increasing or effecting the activity of a receptor. Specifically, a Vps10p-domain receptor agonist is a compound capable of binding to one or more of binding sites of a Vps10p-domain receptor thereby inducing the same physiological response as a given endogenous agonist ligand compound. Analogously TrpV and TrkA agonists are compounds capable of binding to one or more of binding sites of a the TrpV and TrkA receptors thereby inducing the same physiological response as a given endogenous agonist ligand compound.

Antagonist: An antagonist is in this case synonymous with an inhibitor. An antagonist is a compound capable of decreasing the activity of an effector such as a receptor. Specifically, a Vps10p-domain receptor antagonist is a compound capable of binding to one or more of binding sites of Vps10p-domain receptor thereby inhibiting binding of another ligand thus inhibiting a physiological response. Analogously TrpV and TrkA antagonists are compounds capable of binding to one or more of binding sites of a the TrpV and TrkA receptors thereby inhibiting the physiological response of an agonist ligand compound.

antisense-RNA: an RNA molecule capable of causing gene silencing by specifically binding to an mRNA molecule of interest.

antisense-DNA: a DNA molecule capable of causing gene silencing by specifically binding to an mRNA molecule of interest.

Antibody: The term "antibody" as referred to herein includes whole antibodies and any antigen binding fragment (i.e., "antigen-binding portion") or single chain thereof.

"A whole antibody" refers to a glycoprotein comprising at least two heavy (H) chains and two light (L) chains interconnected by disulfide bonds, or an antigen binding portion thereof. Each heavy chain is comprised of a heavy chain variable region (abbreviated herein as $V_H$) and a heavy chain constant region (abbreviated herein as $C_H$). Each light chain is comprised of a light chain variable region (abbreviated herein as $V_L$) and a light chain constant region (abbreviated herein as $C_L$). The $V_H$ and $V_L$ regions can be further subdivided into regions of hypervariability, termed complementarity determining regions (CDRs), interspersed with regions that are more conserved, termed framework regions (FRs). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody, as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR), and (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody.

A further example of an antigen binding-domain is immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. Such binding-domain immunoglobulin fusion proteins are further disclosed in US 2003/0118592 and US 2003/0133939.

These antibody fragments are obtained using conventional techniques known to those with skill in the art, and the fragments are screened for utility in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "discontinuous epitope", as used herein, means a conformational epitope on a protein antigen which is formed from at least two separate regions in the primary sequence of the protein. A discontinuous epitope may also be formed by at least two regions of one or more proteins, in such a case the antigen may be formed by one or more proteins.

The term "bispecific molecule" is intended to include any agent, e.g., a protein, peptide, or protein or peptide complex, which has two different binding specificities. For example, the molecule may bind to, or interact with, (a) a cell surface antigen and (b) an Fc receptor on the surface of an effector cell. The term "multispecific molecule" or "heterospecific molecule" is intended to include any agent, e.g., a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to the CaOU-1 epitope, and to other cell surface antigens or targets, such as Fc receptors on effector cells.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library, and wherein the selected human antibody is at least 90%, more preferably at least 95%, even more preferably at least 96%, 97%, 98%, or 99% identical in amino acid sequence to the amino acid sequence encoded by the germline immunoglobulin gene. Typically, a human antibody derived from a particular human germline sequence will display no more than 10 amino acid differences, more preferably, no more than 5, or even more preferably, no more than 4, 3, 2, or 1 amino acid difference from the amino acid sequence encoded by the germline immunoglobulin gene.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences.

In certain embodiments, however, such recombinant human antibodies can be subjected to in vitro mutagenesis (or, when an animal transgenic for human Ig sequences is used, in vivo somatic mutagenesis) also called affinity maturation and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

An "isolated antibody", as used herein, is intended to refer to an antibody which is substantially free of other antibodies having different antigenic specificities (e.g., an isolated antibody that specifically binds to the CaOU-1 epitope is substantially free of antibodies that specifically bind antigens other than the CaOU-1 epitope). An isolated antibody that specifically binds to an epitope, isoform or variant of the human CaOU-1 epitope may, however, have cross-reactivity to other related antigens, e.g., from other species (e.g., CaOU-1 epitope species homologs). Moreover, an isolated antibody may be substantially free of other cellular material and/or chemicals.

As used herein, "specific binding" refers to antibody binding to a predetermined antigen. Typically, the antibody binds with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less, when measured as apparent affinities based on $IC_{50}$ values in FACS, and binds to the predetermined antigen with an affinity corresponding to a $K_D$ that is at least ten-fold lower, such as at least 100-fold lower than its affinity for binding to a non-specific antigen (e.g., BSA, casein) other than the predetermined antigen or a closely-related antigen.

Avidity: The functional combining strength of an antibody with its antigen which is related to both the affinity of the reaction between the epitopes and paratopes, and the valencies of the antibody and antigen Antibody Classes: Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains constant domains that correspond to the different classes of immunoglobulins are called alpha (α), delta (δ), epsilon (ε), gamma (γ) and mu (μ), respectively. The light chains of antibodies can be assigned to one of two clearly distinct types, called kappa (κ) and lambda (λ), based on the amino sequences of their constant domain. The subunit structures and three-dimensional configurations of different classes of immunoglobulins are well known.

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof. Alternatively, an antibody combining site is known as an antigen binding site.

Chimeric antibody: An antibody in which the variable regions are from one species of animal and the constant regions are from another species of animal. For example, a chimeric antibody can be an antibody having variable regions which derive from a mouse monoclonal antibody and constant regions which are human.

Complementarity determining region or CDR: Regions in the V-domains of an antibody that together form the antibody recognizing and binding domain.

Constant Region or constant domain or C-domain: Constant regions are those structural portions of an antibody molecule comprising amino acid residue sequences within a given isotype which may contain conservative substitutions therein. Exemplary heavy chain immunoglobulin constant regions are those portions of an immunoglobulin molecule known in the art as CH1, CH2, CH3, CH4 and CH5. An exemplary light chain immunoglobulin constant region is that portion of an immunoglobulin molecule known in the art as $C_L$.

Diabodies: This term refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90: 6444-6448 (1993).

Fv: dual chain antibody fragment containing both a $V_H$ and a $V_L$.

Human antibody framework: A molecule having an antigen binding site and essentially all remaining immunoglobulin-derived parts of the molecule derived from a human immunoglobulin.

Humanised antibody framework: A molecule having an antigen binding site derived from an immunoglobulin from a non-human species, whereas some or all of the remaining immunoglobulin-derived parts of the molecule is derived from a human immunoglobulin. The antigen binding site may comprise: either a complete variable domain from the non-human immunoglobulin fused onto one or more human constant domains; or one or more of the complementarity determining regions (CDRs) grafted onto appropriate human framework regions in the variable domain. In a humanized antibody, the CDRs can be from a mouse monoclonal antibody and the other regions of the antibody are human.

Immunoglobulin: The serum antibodies, including IgG, IgM, IgA, IgE and IgD.

Immunoglobulin isotypes: The names given to the Ig which have different H chains, the names are IgG ($IgG_{1,2,3,4}$), IgM, IgA ($IgA_{1,2}$), sIgA, IgE, IgD.

Immunologically distinct: The phrase immunologically distinct refers to the ability to distinguish between two polypeptides on the ability of an antibody to specifically bind one of the polypeptides and not specifically bind the other polypeptide.

Monoclonal Antibody: The phrase monoclonal antibody in its various grammatical forms refers to a population of antibody molecules that contains only one species of antibody combining site capable of immunoreacting with a particular antigen. A monoclonal antibody thus typically displays a single binding affinity for any antigen with which it immunoreacts. A monoclonal antibody may contain an antibody molecule having a plurality of antibody combining sites, each immunospecific for a different antigen, e.g., a bispecific monoclonal antibody.

Polyclonal antibody: Polyclonal antibodies are a mixture of antibody molecules recognising a specific given antigen, hence polyclonal antibodies may recognise different epitopes within said antigen.

Single Chain Antibody or scFv: The phrase single chain antibody refers to a single polypeptide comprising one or more antigen binding sites, most commonly one antigen binding site. Furthermore, although the H and L chains of an Fv fragment are encoded by separate genes, they may be linked either directly or via a peptide, for example a synthetic linker can be made that enables them to be made as a single protein chain (known as single chain antibody, sAb; Bird et al. 1988 Science 242:423-426; and Huston et al. 1988 PNAS 85:5879-5883) by recombinant methods. Such single chain antibodies are also encompassed within the term "antibody", and may be utilized as binding determinants in the design and engineering of a multispecific binding molecule.

Valency: The term valency refers to the number of potential antigen binding sites, i.e. binding domains, in a polypeptide. A polypeptide may be monovalent and contain one antigen binding site or a polypeptide may be bivalent and contain two antigen binding sites. Additionally, a polypeptide may be tetravalent and contain four antigen binding sites. Each antigen binding site specifically binds one antigen. When a polypeptide comprises more than one antigen binding site, each antigen binding site may specifically bind the same or different antigens. Thus, a polypeptide may contain a plurality of antigen binding sites and therefore be multivalent and a polypeptide may specifically bind the same or different antigens.

V-domain: Variable domain are those structural portions of an antibody molecule comprising amino acid residue sequences forming the antigen binding sites. An exemplary light chain immunoglobulin variable region is that portion of an immunoglobulin molecule known in the art as $V_L$.

$V_L$: Variable domain of the light chain.

$V_H$: Variable domain of the heavy chain.

Apoptosis: Apoptosis is a process of suicide by a cell in a multi-cellular organism. It is one of the main types of programmed cell death (PCD), and involves an orchestrated series of biochemical events leading to a characteristic cell morphology and death.

Apoptosis inhibitor: Any compound capable of decreasing the process of apoptosis.

Aromatic group: the term "aromatic group" or "aryl group" means a mono- or polycyclic aromatic hydrocarbon group.

Binding: The term "binding" or "associated with" refers to a condition of proximity between chemical entities or compounds, or portions thereof. The association may be non-covalent-wherein the juxtaposition is energetically favoured by hydrogen bonding or van der Waals or electrostatic interactions-or it may be covalent.

Binding site: The term "binding site" or "binding pocket", as used herein, refers to a region of a molecule or molecular complex that, as a result of its shape, favourably associates with another molecule, molecular complex, chemical entity or compound. As used herein, the pocket comprises at least a deep cavity and, optionally a shallow cavity.

Binding site 1 of Sortilin: A high affinity binding site of neurotensin or synonymously binding site 1 is a binding site of sortilin (SEQ ID NO. 1) having high affinity for neurotensin or a fragment or variant of neurotensin, and having affinity for the sortilin propeptide or a fragment thereof (Amino acid residues 34-77 of SEQ ID NO. 1) said binding site comprising amino acid residues R325, S316, Y351, I353, K260, I327, F314, F350 to M363, S305, F306, T398 to G400, I303-G309, Q349-A356, Y395 and T402 of SEQ ID NO. 1. More preferably, binding site 1 comprises amino acids R325, S316, Y351, I353, K260, I327, F314, F350 to M363, S305, F306 and T398 to G400 of SEQ ID NO. 1. Most preferably binding site 1 of sortilin comprises amino acids R325, S316, Y351, I353, K260, I327, F314 and F350 to M363 of SEQ ID NO. 1. Binding site 1 is a promiscuous binding site.

Binding site 2 of Sortilin: A binding site of sortilin having low affinity for neurotensin or a fragment or variant of neurotensin, said binding site comprising amino acid residues L572, L114, V112, R109 to S111, S115 to G118, T570, G571, W586, W597, T168-I174, L572, A573 and S584 to F588 of SEQ ID NO. 1. More preferably the sortilin low affinity binding site of neurotensin comprises amino acids L572, L114, V112, R109 to S111, S115 to G118, T570, G571, W586 and W597 of SEQ ID NO. 1. Most preferably the sortilin low affinity binding site of neurotensin comprises amino acids L572, L114 and V112. Binding site 2 is promiscuous and may bind the propeptide of Sortilin (amino acid residues 34-77 of SEQ ID NO. 1).

Binding site 3 of Sortilin: A promiscuous binding site of sortilin comprising amino acid residues D403, S420, D422, N423, S424, I425, E426, E444, T451, Y466, E470, I498, S499 and V500 of SEQ ID NO. 1, more preferably comprising amino acid residues D403, N423, S424, I425, T451, Y466, I498 and V500 of SEQ ID NO. 1, most preferably comprising amino acid residues T451, Y466, I498 and V500 of SEQ ID NO. 1.

Bioreactive agent: The term "bioactive agent" as used herein refers to any a substance which may be used in connection with an application that is therapeutic or diagnostic, such as, for example, in methods for diagnosing the presence or absence of a disease in a patient and/or methods for the treatment of a disease in a patient. "Bioactive agent" refers to substances, which are capable of exerting a biological effect in vitro and/or in vivo. The bioactive agents may be neutral, positively or negatively charged. Suitable bioactive agents include, for example, prodrugs, diagnostic agents, therapeutic agents, pharmaceutical agents, drugs, oxygen delivery agents, blood substitutes, synthetic organic molecules, polypeptides, peptides, vitamins, steroids, steroid analogues and genetic determinants, including nucleosides, nucleotides and polynucleotides.

Cationic group: A chemical group capable of functioning as a proton donor when a compound comprising the chemical group is dissolved in a solvent, preferably when dissolved in water.

Chronic pain: Pain (an unpleasant sense of discomfort) that persists or progresses over a long period of time. In contrast to acute pain that arises suddenly in response to a specific injury and is usually treatable, chronic pain persists over time and is often resistant to medical treatments.

Chronic pain may be related to a number of different medical conditions including (but not limited to) diabetes, arthritis, migraine, fibromyalgia, cancer, shingles, sciatica, and previous trauma or injury. Chronic pain may worsen in response to environmental and/or psychological factors. Currently a variety of treatment options are available for people with chronic pain. The goal of pain management is to provide symptom relief and improve an individual's level of functioning in daily activities. A number of types of medications have been used in the management of chronic pain, including acetaminophen, ibuprofen, aspirin, COX-2 inhibitors, anti-migraine medications, sedatives, opioids, and antidepressants. These medications may be co-administered together with the medicament of the present invention. Nonmedicinal treatments for chronic pain can include exercise, physical therapy, counseling, electrical stimulation, biofeedback, acupuncture, hypnosis, chiropractic medicine, and other treatments which may also be combined with treatment with agents of the present invention.

Complex: As used herein the term "complex" refers to the combination of a molecule or a protein, conservative analogues or truncations thereof associated with a chemical entity. Specifically the present invention relate to a binary complex between a Vps10p-domain receptor and a TrpV receptor wherein said binary complex optionally may bind a third receptor component such as, but not limited to a TrkA receptor or a fragment or variant thereof. The inventors have found that the binary and the ternary complex mentioned above are involved in transduction of pain signals which may be limited or abolished by inhibiting formation of said binary or ternary complex.

Coordinate: The term "coordinate" as use herein, refers to the information of the three dimensional organization of the atoms contributing to a protein structure. The final map containing the atomic coordinates of the constituents of the crystal may be stored on a data carrier; typically the data is stored in PDB format or in mmCIF format, both of which are known to the person skilled in the art. However, crystal coordinates may as well be stored in simple tables or text formats. The PDB format is organized according to the instructions and guidelines given by the Research Collaboratory for Structural Biology.

Cyclic group: the term "cyclic group" means a closed ring hydrocarbon group that is classified as an alicyclic group, aromatic group, or heterocyclic group.

Cycloalkenyl: means a monovalent unsaturated carbocyclic radical consisting of one, two or three rings, of three to eight carbons per ring, which can optionally be substituted with one or two substituents selected from the group consisting of hydroxy, cyano, lower alkenyl, lower alkoxy, lower haloalkoxy, alkenylthio, halo, haloalkenyl, hydroxyalkenyl, nitro, alkoxycarbonenyl, amino, alkenylamino, alkenylsulfonyl, arylsulfonyl, alkenylaminosulfonyl, arylaminosulfonyl, alkylsulfonylamino, arylsulfonylamino, alkenylaminocarbonyl, arylaminocarbonyl, alkenylcarbonylamino and arylcarbonylamino.

Cycloalkyl: means a monovalent saturated carbocyclic radical consisting of one, two or three rings, of three to eight carbons per ring, which can optionally be substituted with one or two substituents selected from the group consisting of hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino and arylcarbonylamino.

Dipole-dipole interaction: The term "dipole-dipole interaction" as used herein refers to the attraction which can occur among two or more polar molecules. Thus, "dipole-dipole interaction" refers to the attraction of the uncharged, partial positive end of a first polar molecule to the uncharged, partial negative end of a second polar molecule. "Dipole-dipole interaction" also refers to intermolecular hydrogen bonding.

Electrostatic interaction: The term "electrostatic interaction" as used herein refers to any interaction occurring between charged components, molecules or ions, due to attractive forces when components of opposite electric charge are attracted to each other. Examples include, but are not limited to: ionic interactions, covalent interactions, interactions between a ion and a dipole (ion and polar molecule), interactions between two dipoles (partial charges of polar molecules), hydrogen bonds and London dispersion bonds (induced dipoles of polarizable molecules). Thus, for example, "ionic interaction" or "electrostatic interaction" refers to the attraction between a first, positively charged molecule and a second, negatively charged molecule. Ionic or electrostatic interactions include, for example, the attraction between a negatively charged bioactive agent.

Entity: An entity is unit. Specifically an entity of the Vps10p-domain receptor:TrpV receptor binary complex may be a Vps10p-domain receptor selected from the group consisting of Sortilin (SEQ ID NO. 1), SorLA (SEQ ID NO. 2), SorCS1 (SEQ ID NO. 3), SorCS2 (SEQ ID NO. 4) and SorCS3 (SEQ ID NO. 5), and/or a TrpV receptor selected from the group consisting of TrpV1 (SEQ ID NO. 6), TrpV2 (SEQ ID NO. 7), TrpV3 (SEQ ID NO. 8) and TrpV4 (SEQ ID NO. 9).

Accordingly an entity of the Vps10p-domain receptor:TrkA:TrpV receptor ternary complex may be a Vps10p-domain receptor selected from the group consisting of Sortilin Sortilin (SEQ ID NO. 1), SorLA (SEQ ID NO. 2), SorCS1 (SEQ ID NO. 3), SorCS2 (SEQ ID NO. 4) and SorCS3 (SEQ ID NO. 5), and/or a TrpV receptor selected from the group consisting of TrpV1 (SEQ ID NO. 6), TrpV2 (SEQ ID NO. 7), TrpV3 (SEQ ID NO. 8) and TrpV4 (SEQ ID NO. 9), and/or a TrkA receptor (SEQ ID NO. 10).

Fab-fragment: The fragment antigen binding Fab fragment is a region on an antibody which binds to antigens. It is composed of one constant and one variable domain of each of the heavy and the light chain. These domains shape the paratope—the antigen binding site—at the amino terminal end of the monomer. The two variable domains bind the epitope on their specific antigens.

In an experimental setting, Fc and Fab fragments can be generated in the laboratory. The enzyme papain can be used to cleave an immunoglobulin monomer into two Fab fragments and an Fc fragment. The enzyme pepsin cleaves below hinge region, so a F(ab')2 fragment and a Fc fragment is formed. The variable regions of the heavy and light chains can be fused together to form a single chain variable fragment (scFv), which is only half the size of the Fab fragment yet retains the original specificity of the parent immunoglobulin.

Form a ring: means that the atoms mentioned are connected through a bond when the ring structure is formed.

Fragments: The polypeptide fragments according to the present invention, including any functional equivalents thereof, may in one embodiment comprise less than 500 amino acid residues, such as less than 450 amino acid residues, for example less than 400 amino acid residues, such as less than 350 amino acid residues, for example less than 300 amino acid residues, for example less than 250 amino acid residues, such as less than 240 amino acid residues, for example less than 225 amino acid residues, such as less than 200 amino acid residues, for example less than 180 amino acid residues, such as less than 160 amino acid residues, for example less than 150 amino acid residues, such as less than 140 amino acid residues, for example less than 130 amino acid residues, such as less than 120 amino acid residues, for example less than 110 amino acid residues, such as less than 100 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues. Fragments of neurotensin include but is not limited to the C-terminal amino acids of neurotensin PYIL and YIL.

Functional equivalency: "Functional equivalency" as used in the present invention is, according to one preferred embodiment, established by means of reference to the corresponding functionality of a predetermined fragment of the sequence.

Functional equivalents or variants of a Vps10p-domain receptor modulator will be understood to exhibit amino acid sequences gradually differing from the preferred predetermined proneurotrophin activity modulator sequence, as the number and scope of insertions, deletions and substitutions including conservative substitutions increase. This difference is measured as a reduction in homology between the preferred predetermined sequence and the fragment or functional equivalent.

A functional variant obtained by substitution may well exhibit some form or degree of native proneurotrophin activity modulator activity, and yet be less homologous, if residues containing functionally similar amino acid side chains are substituted. Functionally similar in this respect refers to dominant characteristics of the side chains such as hydrophobic, basic, neutral or acidic, or the presence or absence of steric bulk. Accordingly, in one embodiment of the invention, the degree of identity is not a principal measure of a fragment being a variant or functional equivalent of a preferred predetermined fragment according to the present invention.

Gene "silencing": a process leading to reduced expression of endogenous genes. Gene silencing is preferably the result of post-transcriptional reduction of gene expression.

Group: (Moiety/substitution) as is well understood in this technical area, a large degree of substitution is not only tolerated, but is often advisable. Substitution is anticipated on the materials of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, or S atoms, for example, in the chain as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like. The same definitions apply to "alkenyl group" and "alkenyl moiety"; to "alkynyl group" and "alkynyl moiety"; to "cyclic group" and "cyclic moiety; to "alicyclic group" and "alicyclic moiety"; to "aromatic group" or "aryl group" and to "aromatic moiety" or "aryl moiety"; as well as to "heterocyclic group" and "heterocyclic moiety".

Heterocyclic group: the term "heterocyclic group" means a closed ring hydrocarbon in which one or more of the atoms in the ring is an element other than carbon (e.g., nitrogen, oxygen, sulphur, etc.).

Heterocyclyl means a monovalent saturated cyclic radical, consisting of one to two rings, of three to eight atoms per ring, incorporating one or two ring heteroatoms (chosen from N, O or $S(O)_{0-2}$, and which can optionally be substituted with one or two substituents selected from the group consisting of hydroxyl, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminofarbonyl, arylaminocarbonyl, alkylcarbonylamino, or arylcarbonylamino.

Heteroaryl means a monovalent aromatic cyclic radical having one to three rings, of four to eight atoms per ring, incorporating one or two heteroatoms (chosen from nitrogen, oxygen, or sulphur) within the ring which can optionally be substituted with one or two substituents selected from the group consisting of hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonlamino and arylcarbonylamino.

Homology: The homology between amino acid sequences may be calculated using well known scoring matrices such as any one of BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, and BLOSUM 90.

Fragments sharing homology with fragments of SEQ ID NO:1 to 13, respectively, are to be considered as falling within the scope of the present invention when they are preferably at least about 60 percent homologous, for example at least 65 percent homologous, for example at least 70 percent homologous, for example at least 75 percent homologous, for example at least 80 percent homologous, for example at least 85 percent homologous, for example at least 90 percent homologous, for example at least 92 percent homologous, such as at least 94 percent homologous, for example at least 95 percent homologous, such as at least 96 percent homologous, for example at least 97 percent homologous, such as at least 98 percent homologous, for example at least 99 percent homologous with said predetermined fragment sequences, respectively. According to one embodiment of the invention, the homology percentages refer to identity percentages.

A further suitably adaptable method for determining structure and function relationships of peptide fragments is described in U.S. Pat. No. 6,013,478, which is herein incorporated by reference. Also, methods of assaying the binding of an amino acid sequence to a receptor moiety are known to the skilled artisan.

In addition to conservative substitutions introduced into any position of a preferred predetermined proneurotrophin activity modulator, or a fragment thereof, it may also be desirable to introduce non-conservative substitutions in any one or more positions of such a proneurotrophin activity modulator.

A non-conservative substitution leading to the formation of a functionally equivalent fragment of proneurotrophin activity modulator would for example i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Variants obtained by substitution of amino acids may in one preferred embodiment be made based upon the hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

In addition to the variants described herein, sterically similar variants may be formulated to mimic the key portions of the variant structure and that such compounds may also be used in the same manner as the variants of the invention. This may be achieved by techniques of modelling and chemical designing known to those of skill in the art. It will be understood that all such sterically similar constructs fall within the scope of the present invention.

In a further embodiment the present invention relates to functional variants comprising substituted amino acids having hydrophilic values or hydropathic indices that are within +/−4.9, for example within +/−4.7, such as within +/−4.5, for example within +/−4.3, such as within +/−4.1, for example within +/−3.9, such as within +/−3.7, for example within +/−3.5, such as within +/−3.3, for example within +/−3.1, such as within +/−2.9, for example within +/−2.7, such as within +/−2.5, for example within +/−2.3, such as within +/−2.1, for example within +/−2.0, such as within +/−1.8, for example within +/−1.6, such as within +/−1.5, for example within +/−1.4, such as within +/−1.3 for example within +/−1.2, such as within +/−1.1, for example within +/−1.0, such as within +/−0.9, for example within +/−0.8, such as within +/−0.7, for example within +/−0.6, such as within +/−0.5, for example within +/−0.4, such as within +/−0.3, for example within +/−0.25, such as within +/−0.2 of the value of the amino acid it has substituted.

The importance of the hydrophilic and hydropathic amino acid indices in conferring interactive biologic function on a protein is well understood in the art (Kyte & Doolittle, 1982 and Hopp, U.S. Pat. No. 4,554,101, each incorporated herein by reference).

The amino acid hydropathic index values as used herein are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5) (Kyte & Doolittle, 1982).

The amino acid hydrophilicity values are: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) (U.S. Pat. No. 4,554,101).

In addition to the peptidyl compounds described herein, sterically similar compounds may be formulated to mimic the key portions of the peptide structure and that such compounds may also be used in the same manner as the peptides of the invention. This may be achieved by techniques of modelling and chemical designing known to those of skill in the art. For example, esterification and other alkylations may be employed to modify the amino terminus of, e.g., a di-arginine peptide backbone, to mimic a tetra peptide structure. It will be understood that all such sterically similar constructs fall within the scope of the present invention.

Peptides with N-terminal alkylations and C-terminal esterifications are also encompassed within the present invention. Functional equivalents also comprise glycosylated and covalent or aggregative conjugates formed with the same or other proneurotrophin activity modulator fragments and/or proneurotrophin activity modulator molecules, including dimers or unrelated chemical moieties. Such functional equivalents are prepared by linkage of functionalities to groups which are found in fragment including at any one or both of the N- and C-termini, by means known in the art.

Functional equivalents may thus comprise fragments conjugated to aliphatic or acyl esters or amides of the carboxyl terminus, alkylamines or residues containing carboxyl side chains, e.g., conjugates to alkylamines at aspartic acid residues; O-acyl derivatives of hydroxyl group-containing residues and N-acyl derivatives of the amino terminal amino acid or amino-group containing residues, e.g. conjugates with fMet-Leu-Phe or immunogenic proteins. Derivatives of the acyl groups are selected from the group of alkyl-moieties (including C3 to C10 normal alkyl), thereby forming alkanoyl species, and carbocyclic or heterocyclic compounds, thereby forming aroyl species. The reactive groups preferably are difunctional compounds known per se for use in cross-linking proteins to insoluble matrices through reactive side groups.

Covalent or aggregative functional equivalents and derivatives thereof are useful as reagents in immunoassays or for affinity purification procedures. For example, a fragment of proneurotrophin activity modulator according to the present invention may be insolubilized by covalent bonding to cyanogen bromide-activated Sepharose by methods known per se or adsorbed to polyolefin surfaces, either with or without glutaraldehyde cross-linking, for use in an assay or purification of anti-neurotrophin activity modulator antibodies or cell surface receptors. Fragments may also be labelled with a detectable group, e.g., radioiodinated by the chloramine T procedure, covalently bound to rare earth chelates or conjugated to another fluorescent moiety for use in e.g. diagnostic assays.

Mutagenesis of a preferred predetermined fragment of proneurotrophin activity modulator can be conducted by making amino acid insertions, usually on the order of about from 1 to 10 amino acid residues, preferably from about 1 to 5 amino acid residues, or deletions of from about from 1 to 10 residues, such as from about 2 to 5 residues.

In one embodiment the ligand of binding site 1, 2 or 3 is an oligopeptide synthesised by automated synthesis. Any of the commercially available solid-phase techniques may be employed, such as the Merrifield solid phase synthesis method, in which amino acids are sequentially added to a growing amino acid chain (see Merrifield, J. Am. Chem. Soc. 85:2149-2146, 1963).

Equipment for automated synthesis of polypeptides is commercially available from suppliers such as Applied Biosystems, Inc. of Foster City, Calif., and may generally be operated according to the manufacturer's instructions. Solid phase synthesis will enable the incorporation of desirable amino acid substitutions into any fragment of proneurotrophin activity modulator according to the present invention. It will be understood that substitutions, deletions, insertions or any subcombination thereof may be combined to arrive at a final sequence of a functional equivalent. Insertions shall be understood to include amino-terminal and/or carboxyl-terminal fusions, e.g. with a hydrophobic or immunogenic protein or a carrier such as any polypeptide or scaffold structure capable as serving as a carrier.

Oligomers including dimers including homodimers and heterodimers of fragments of sortilin inhibitors according to the invention are also provided and fall under the scope of the invention. Proneurotrophin activity modulator functional equivalents and variants can be produced as homodimers or heterodimers with other amino acid sequences or with native sortilin inhibitor sequences. Heterodimers include dimers containing immunoreactive sortilin inhibiting fragments as well as sortilin inhibiting fragments that need not have or exert any biological activity.

Vpas10p-domain receptor antagonists including but not limited to Sortilin inhibiting peptide fragments may be synthesised both in vitro and in vivo. Method for in vitro synthesis are well known, and methods being suitable or suitably adaptable to the synthesis in vivo of sortilin inhibitors are also described in the prior art. When synthesized in vivo, a host cell is transformed with vectors containing DNA encoding a sortilin peptide inhibitor or a fragment thereof. A vector is defined as a replicable nucleic acid construct. Vectors are used to mediate expression of proneurotrophin activity modulator. An expression vector is a replicable DNA construct in which a nucleic acid sequence encoding the predetermined sortilin inhibitting fragment, or any functional equivalent thereof that can be expressed in vivo, is operably linked to suitable control sequences capable of effecting the expression of the fragment or equivalent in a suitable host. Such control sequences are well known in the art. Both prokaryotic and eukaryotic cells may be used for synthesising ligands.

Cultures of cells derived from multicellular organisms however represent preferred host cells. In principle, any higher eukaryotic cell culture is workable, whether from vertebrate or invertebrate culture. Examples of useful host cell lines are VERO and HeLa cells, Chinese hamster ovary (CHO) cell lines, and WI38, BHK, COS-7, 293 and MDCK cell lines. Preferred host cells are eukaryotic cells known to synthesize endogenous sortilin inhibitors. Cultures of such host cells may be isolated and used as a source of the fragment, or used in therapeutic methods of treatment, including therapeutic methods aimed at promoting or inhibiting a growth state, or diagnostic methods carried out on the human or animal body.

Hydrophobic bond: The term "hydrogen bond" as used herein refers to an attractive force, or bridge, which may occur between a hydrogen atom which is bonded covalently to an electronegative atom, for example, oxygen, sulphur, or nitrogen, and another electronegative atom. The hydrogen bond may occur between a hydrogen atom in a first molecule and an electronegative atom in a second molecule (intermolecular hydrogen bonding). Also, the hydrogen bond may occur between a hydrogen atom and an electronegative atom which are both contained in a single molecule (intramolecular hydrogen bonding).

Hydrophobic interaction: The term "hydrophobic interaction" as used herein refers to any interaction occurring between essentially non-polar (hydrophobic) components located within attraction range of one another in a polar environment (e.g. water). As used herein, attraction range is on the scale of from 0.1 up to 2 nm. A particular type of hydrophobic interaction is exerted by "Van der Waal's forces", i.e. the attractive forces between non-polar molecules that are accounted for by quantum mechanics. Van der Waal's forces are generally associated with momentary dipole moments which are induced by neighbouring molecules and which involve changes in electron distribution.

Inhibiting: The term inhibiting as used herein refers to the prevention of binding between two or more components of a Vps10p-domain receptor:TrpV receptor binary complex, and/or a Vps10p-domain receptor:TrkA:TrpV receptor ternary complex.

In vitro/in vivo: the terms are used in their normal meaning.

Lesions: are caused by any process that damages tissues. A cancerous tumor is an example of a lesion, however the surrounding tissue damaged by a tumor is also a lesion. Trauma, including electrocution and chemical burns can also cause lesions. Certain diseases present lesions, for example the skin deformities caused by chicken pox. Lesions can also be caused by metabolic processes, like an ulcer or autoimmune activity, as in the case with many forms of arthritis. Lesions are sometimes intentionally inflicted during neurosurgery, such as the carefully-placed brain lesion used to treat epilepsy and other brain disorders.

Ligand: a substance, compound or biomolecule such as a protein including receptors, that is able to bind to and form a complex with (a second) biomolecule to serve a biological purpose. In a narrower sense, it is a signal triggering molecule binding to a site on a target protein, by intermolecular forces such as ionic bonds, hydrogen bonds and Van der Waals forces. The docking (association) is usually reversible (dissociation). Actual irreversible covalent binding between a ligand and its target molecule is rare in biological systems. As opposed to the meaning in metalorganic and inorganic chemistry, it is irrelevant, whether or not the ligand actually binds at a metal site, as it is the case in hemoglobin. Ligand binding to receptors may alter the chemical conformation, i.e. the three dimensional shape of the receptor protein. The conformational state of a receptor protein determines the functional state of a receptor. The tendency or strength of binding is called affinity. Ligands include substrates, inhibitors, activators, non-self receptors, co-receptors and neurotransmitters. Radioligands are radioisotope labeled compounds and used in vivo as tracers in PET studies and for in vitro binding studies.

Moieties of a particular compound cover group(s) or part(s) of said particular compound.

Neuropathic pain: is a chronic pain initiated or caused by a primary lesion or dysfunction in the nervous system.

Pharmaceutical agent: The terms "pharmaceutical agent" or "drug" or "medicament" refer to any therapeutic or prophylactic agent which may be used in the treatment (including the prevention, diagnosis, alleviation, or cure) of a malady, affliction, condition, disease or injury in a patient. Therapeutically useful genetic determinants, peptides, polypeptides and polynucleotides may be included within the meaning of the term pharmaceutical or drug. As defined herein, a "therapeutic agent", "pharmaceutical agent" or "drug" or "medicament" is a type of bioactive agent.

Pharmaceutical composition: or drug, medicament or agent refers to any chemical or biological material, compound, or composition capable of inducing a desired therapeutic effect when properly administered to a patient. Some drugs are sold in an inactive form that is converted in vivo into a metabolite with pharmaceutical activity. For purposes of the present invention, the terms "pharmaceutical composition" and "medicament" encompass both the inactive drug and the active metabolite.

Polypeptide: The term "polypeptide" as used herein refers to a molecule comprising at least two amino acids. The amino acids may be natural or synthetic. "Oligopeptides" are defined herein as being polypeptides of length not more than 100 amino acids. The term "polypeptide" is also intended to include proteins, i.e. functional biomolecules comprising at least one polypeptide; when comprising at least two polypeptides, these may form complexes, be covalently linked or may be non-covalently linked. The polypeptides in a protein can be glycosylated and/or lipidated and/or comprise prosthetic groups.

Polynucleotide: "Polynucleotide" as used herein refers to a molecule comprising at least two nucleic acids. The nucleic acids may be naturally occurring or modified, such as locked nucleic acids (LNA), or peptide nucleic acids (PNA). Polynucleotide as used herein generally pertains to i) a polynucleotide comprising a predetermined coding sequence, or ii) a polynucleotide encoding a predetermined amino acid sequence, or iii) a polynucleotide encoding a fragment of a polypeptide encoded by polynucleotides (i) or (ii), wherein said fragment has at least one predetermined activity as specified herein; and iv) a polynucleotide the complementary strand of which hybridizes under stringent conditions with a polynucleotide as defined in any one of (i), (ii) and (iii), and encodes a polypeptide, or a fragment thereof, having at least one predetermined activity as specified herein; and v) a polynucleotide comprising a nucleotide sequence which is degenerate to the nucleotide sequence of polynucleotides (iii) or (iv);

or the complementary strand of such a polynucleotide.

Purified antibody: The term a "purified antibody" is an antibody at least 60 weight percent of which is free from the polypeptides and naturally-occurring organic molecules with which it is naturally associated. Preferably, the preparation comprises antibody in an amount of at least 75 weight percent, more preferably at least 90 weight percent, and most preferably at least 99 weight percent.

Root mean square deviation: The term "root mean square deviation" (rmsd) is used as a mean of comparing two closely related structures and relates to a deviation in the distance between related atoms of the two structures after structurally minimizing this distance in an alignment. Related proteins with closely related structures will be characterized by relatively low RMSD values whereas larger differences will result in an increase of the RMSD value.

Sequence identity: Sequence identity is determined in one embodiment by utilising fragments of proneurotrophin activity modulator peptides comprising at least 25 contiguous amino acids and having an amino acid sequence which is at least 80%, such as 85%, for example 90%, such as 95%, for example 99% identical to the amino acid sequence of any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10 respectively, wherein the percent identity is determined with the algorithm GAP, BESTFIT, or FASTA in the Wisconsin Genetics Software Package Release 7.0, using default gap weights.

The following terms are used to describe the sequence relationships between two or more polynucleotides: "predetermined sequence", "comparison window", "sequence identity", "percentage of sequence identity", and "substantial identity".

A "predetermined sequence" is a defined sequence used as a basis for a sequence comparison; a predetermined sequence may be a subset of a larger sequence, for example, as a segment of a full-length DNA or gene sequence given in a sequence listing, such as a polynucleotide sequence of SEQ ID NO:1, or may comprise a complete DNA or gene sequence. Generally, a predetermined sequence is at least 20 nucleotides in length, frequently at least 25 nucleotides in length, and often at least 50 nucleotides in length.

Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a predetermined sequence of at least 20 contiguous nucleotides and wherein the portion of the polynucleotide sequence in the comparison window may comprise additions or deletions (i.e., gaps) of 20 percent or less as compared to the predetermined sequence (which does not comprise additions or deletions) for optimal alignment of the two sequences.

Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a predetermined sequence over a comparison window of at least 20 nucleotide positions, frequently over a window of at least 25-50 nucleotides, wherein the percentage of sequence identity is calculated by comparing the predetermined sequence to the polynucleotide sequence which may include deletions or additions which total 20 percent or less of the predetermined sequence over the window of comparison. The predetermined sequence may be a subset of a larger sequence, for example, as a segment of the full-length SEQ ID NO:1 polynucleotide sequence illustrated herein.

As applied to polypeptides, a degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences.

An "unrelated" or "non-homologous" sequence shares less than 40% identity, though preferably less than 25% identity, with one of the proneurotrophin activity modulator polypeptide sequences of the present invention. The term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine, a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine.

Additionally, variants are also determined based on a predetermined number of conservative amino acid substitutions as defined herein below. Conservative amino acid substitution as used herein relates to the substitution of one amino acid (within a predetermined group of amino acids) for another amino acid (within the same group), wherein the amino acids exhibit similar or substantially similar characteristics.

Within the meaning of the term "conservative amino acid substitution" as applied herein, one amino acid may be substituted for another within the groups of amino acids indicated herein below:
i) Amino acids having polar side chains (Asp, Glu, Lys, Arg, His, Asn, Gln, Ser, Thr, Tyr, and Cys)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gln)
ix) Amino acids having hydroxy side chains (Ser, Thr)
x) Amino acids having sulphur-containing side chains (Cys, Met),
xi) Neutral, weakly hydrophobic amino acids (Pro, Ala, Gly, Ser, Thr)
xii) Hydrophilic, acidic amino acids (Gln, Asn, Glu, Asp), and
xiii) Hydrophobic amino acids (Leu, Ile, Val)

Accordingly, a variant or a fragment thereof according to the invention may comprise, within the same variant of the sequence or fragments thereof, or among different variants of the sequence or fragments thereof, at least one substitution, such as a plurality of substitutions introduced independently of one another.

It is clear from the above outline that the same variant or fragment thereof may comprise more than one conservative amino acid substitution from more than one group of conservative amino acids as defined herein above.

The addition or deletion of at least one amino acid may be an addition or deletion of from preferably 2 to 250 amino acids, such as from 10 to 20 amino acids, for example from 20 to 30 amino acids, such as from 40 to 50 amino acids. However, additions or deletions of more than 50 amino acids, such as additions from 50 to 100 amino acids, addition of 100 to 150 amino acids, addition of 150-250 amino acids, are also comprised within the present invention. The deletion and/or the addition may—independently of one another—be a deletion and/or an addition within a sequence and/or at the end of a sequence.

siRNA: "small interfering RNA" (siRNA) is a short (often, but not restricted to, less than 30 nucleotides long) double-stranded RNA molecule capable of causing gene-specific silencing in mammalian cells.

Substituted lower alkyl means a lower alkyl having one to three substituents selected from the group consisting of hydroxyl, alkoxy, amino, amido, carboxyl, acyl, halogen, cyano, nitro and thiol.

Treatment: The term "treatment" as used herein refers to a method involving therapy including surgery of a clinical condition in an individual including a human or animal body. The therapy may be ameliorating, curative or prophylactic, i.e. reducing pain symptoms.

Variants: The term "variants" as used herein refers to amino acid sequence variants said variants preferably having at least 60% identity, for example at least 63% identity, such as at least 66% identity, for example at least 70% sequence identity, for example at least 72% sequence identity, for example at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with any of the predetermined sequences.

Up-regulation of expression: a process leading to increased expression of genes, preferably of endogenous genes.

Pain

The present inventors have discovered that pain sensations may be eliminated by preventing interaction between a Vps10p-domain receptor in complex with a TrpV receptor and a third component including but not limited to the TrkA receptor. Pain may be subdivided in chronic pain and acute pain which in turn may be further sub-divided.

Accordingly, in one embodiment of the present invention the pain is chronic pain.

In another embodiment of the present invention the pain is neuropathic pain.

In another embodiment of the present invention the chronic pain is neuropathic pain.

In another embodiment of the present invention the acute pain is neuropathic pain.

In a further embodiment of the present invention the neuropathic pain is selected from the group consisting of peripheral neuropathic pain, central neuropathic pain and mixed neuropathic pain.

In a further embodiment the neuropathic pain is due to mechanical injury to peripheral or central nerves, metabolic injury, infectious injury or cancer invasion of nerves by tumour and cytotoxic treatment.

In a further embodiment the mechanical injury is due to accidental lesions, compression or axotomy including amputation and operation.

In one embodiment the metabolic injury causing the pain is diabetic neuropathy.

In another embodiment the infectious injury causing the pain is herpes zoster and HIV neuropathy.

In a further embodiment the pain as described herein above is acute pain.

The Target Receptor Complex

The (analgesic) agent according to the invention, as defined herein is aimed at preventing formation of a specified target complex, said target complex upon formation and being capable of inducing a pain sensation.

In one embodiment the Vps10p domain receptor of said complex is at least 60% identical to SEQ ID NO. 1.

In another embodiment said Vps10p-domain receptor is selected from the group consisting of SEQ ID NO. 1, SEQ ID NO. 2, SEQ ID NO. 3, SEQ ID NO. 4 and SEQ ID NO. 5.

In one embodiment of the present invention the TrpV receptor of the complex is selected from the group consisting of SEQ ID NO. 6, SEQ ID NO. 7, SEQ ID NO. 8 and SEQ ID NO. 9.

In another embodiment of the present invention the TrkA receptor is SEQ ID NO. 10.

In one embodiment the mammal to which agents of the present invention are administered, is a human being.

Analgesic Agent

In a main aspect the present invention relate to the use of at least one agent (antagonist, compound, inhibitor or its synonyms) capable of binding to a receptor (an entity) of the Vps10p-domain receptor:TrpV receptor binary complex, and/or Vps10p-domain receptor:TrkA:TrpV receptor ternary complex thus inhibiting the pain transducing activity of said complex, in the manufacture of a medicament, for the treatment and/or prevention of pain, including but not limited to acute pain, neuropathic pain and chronic pain, in an animal.

The invention in a further main aspect relates to the use of at least one agent capable of binding to an entity of the:
a. Vps10p-domain receptor:TrpV receptor binary complex, and/or
b. Vps10p-domain receptor:TrkA:TrpV receptor ternary complex thus inhibiting formation of said complex, for the preparation of a medicament for the treatment of pain in a mammal.

The invention also relate to the use of at least one agent capable of inhibiting formation of the:
a. Vps10p-domain receptor:TrpV receptor binary complex, and/or
b. Vps10p-domain receptor:TrkA:TrpV receptor ternary complex,
for the preparation of a medicament for the treatment of pain in a mammal.

The invention in one aspect relates to at least one agent capable of inhibiting formation of the:
a. Vps10p-domain receptor:TrpV receptor binary complex, and/or
b. Vps10p-domain receptor:TrkA:TrpV receptor ternary complex,
for use in a method of treatment of pain in a mammal.

In one embodiment of the present invention the at least one agent as discussed herein above is selected from proteins, peptides, polypeptides, antibodies, antisense RNA, antisense-DNA, small organic molecules, siRNA, soluble Vps10p-domain receptors and fragments and variants thereof, soluble TrpV receptors and fragments and variants thereof and soluble TrkA receptors and fragments and variants thereof.

In one embodiment the mammal to which agents of the present invention are administered, is a human being, a mouse or a rat.

In one embodiment the mammal to which agents of the present invention are administered, is a rabbit.

Biding Epitope

The present invention relates to agents capable of inhibiting the target complex as defined herein above. The invention does so by binding to an entity of said complex.

Accordingly, in one embodiment the at least one agent is bound to at least one amino acid residue of the binding site comprising amino acid residues R325, S316, Y351, I353, K260, I327, F314, F350 to M363, S305, F306, T398 to G400, I303-G309, Q349-A356, Y395 and T402 of SEQ ID NO. 1 or a fragment or variant thereof.

In another embodiment the at least one agent of the present invention is bound to at least one amino acid residue of the binding site comprising amino acid residues R325, S316, Y351, I353, K260, I327, F314, F350 to M363, S305, F306 and T398 to G400 of SEQ ID NO. 1 or a fragment or variant thereof.

In another embodiment the at least one agent of the present invention is bound to at least one amino acid residue of the binding site comprising amino acid residues R325, S316, Y351, I353, K260, I327, F314 and F350 to M363 of SEQ ID NO. 1 or a fragment or variant thereof.

In another embodiment the at least one agent of the present invention is bound to at least one amino acid residue of the binding site comprising amino acid residues L572, L114, V112, R109 to S111, S115 to G118, T570, G571, W586, W597, T168-I174, L572, A573 and S584 to F588 of SEQ ID NO. 1 or a fragment or variant thereof.

In another embodiment the at least one agent of the present invention is bound to at least one amino acid residue of the binding site comprising amino acid residues L572, L114, V112, R109 to S111, S115 to G118, T570, G571, W586 and W597 of SEQ ID NO. 1 or a fragment or variant thereof.

In another embodiment the at least one agent of the present invention is bound to at least one amino acid residue of the binding site comprising amino acid residues L572, L114 and V112 of SEQ ID NO. 1 or a fragment or variant thereof.

In another embodiment the at least one agent of the present invention is bound to at least one amino acid residue of the binding site comprising amino acid residues D403, S420, D422, N423, S424, I425, E426, E444, T451, Y466, E470, I498, S499 and V500 of SEQ ID NO. 1 or a fragment or variant thereof.

In another embodiment the at least one agent of the present invention is bound to at least one amino acid residue of the binding site comprising amino acid residues D403, N423, S424, I425, E444, T451, Y466, I498 and V500 of SEQ ID NO. 1 or a fragment or variant thereof.

In another embodiment the at least one agent of the present invention is bound to at least one amino acid residue of the binding site comprising amino acid residues E444, T451, Y466, I498 and V500 of SEQ ID NO. 1 or a fragment or variant thereof.

Structural Definition of the Agent of the Present Invention

Agents capable of binding to the epitopes defined above, are selected from the group consisting of proteins, peptides, oligopeptides, polypeptides, antibodies, antisense RNA, antisense-DNA, small organic molecules, siRNA and soluble receptors selected from the group consisting of TrpV receptors, TrkA receptors and Vps10p-domain receptors and fragments and variants thereof, or a combination thereof.

In one embodiment, the agent of the present invention is selected from the group consisting of:
a. an isolated polypeptide selected from the group consisting of
   i. an amino acid sequence consisting of SEQ ID NOs: 1, 2, 3, 4, 5, 6, 7, 8, 9 or 10;
   ii. a biologically active sequence variant of the amino acid sequence of a) wherein the variant has at least 70% sequence identity to said SEQ ID NO: 1, 2, 3, 4, 5, 6, 7, 8, 9 or 10; or
   iii. a biologically active fragment of any of i or ii wherein said fragment comprises at least 50 contiguous amino acids of any of a) through b), and having at least 70% sequence identity to SEQ ID NO: 1, 2, 3, 4, 5, 6, 7, 8, 9 or 10 in a range of overlap of at least 50 amino acids, wherein the biological activity is inhibiting formation of the: Vps10p-domain receptor:TrpV receptor binary complex, and/or the Vps10p-domain receptor:TrkA:TrpV receptor ternary complex; or
b. an isolated nucleotide comprising a nucleic acid sequence encoding a polypeptide as defined under a) or a nucleic acid sequence being a complementary sequence to a sequence encoding a polypeptide as defined under a), or
c. an expression vector comprising the nucleic acid sequence as defined under b), or
d. a composition of cells, wherein said cells are transformed or transduced with the vector as defined under c), or
e. a packaging cell line comprising the nucleic acid sequence as defined under b).

In a further embodiment, the polypeptide is a naturally occurring allelic variant of the sequence selected from the group consisting of SEQ ID NO: SEQ ID NOs: 1, 2, 3, 4, 5, 6, 7, 8, 9 and 10.

In yet another embodiment, the polypeptide is a variant polypeptide described therein, wherein any amino acid specified in the selected sequence is altered to provide a conservative substitution.

In one embodiment, the polypeptide has at least 70% sequence identity, such as 75% sequence identity, such as 80% sequence identity, such as 85% sequence identity, such as 90% sequence identity, such as 95% sequence identity, such as 96% sequence identity, such as 97% sequence identity, such as 98% sequence identity, such as 99% sequence identity, such as 100% sequence identity to a protein having a sequence selected from the group consisting of SEQ ID NOs: 1, 2, 3, 4, 5, 6, 7, 8, 9 and 10.

In one embodiment, the polypeptide is glycosylated.

In yet another embodiment, polypeptide is a soluble polypeptide being a fragment of any of said SEQ ID NOs: 1, 2, 3, 4, 5, 6, 7, 8, 9 or 10.

In yet another embodiment, the polypeptide is capable of forming at least one intramolecular cystine bridge.

In yet another embodiment, the polypeptide comprises a dimer of said polypeptide linked through at least one intermolecular cystine bridge.

In yet another embodiment, the polypeptide of the invention further comprises an affinity tag, such as a polyhis tag, a GST tag, a HA tag, a Flag tag, a C-myc tag, a HSV tag, a V5 tag, a maltose binding protein tag, a cellulose binding domain tag.

In one embodiment, the agent of the present invention is a nucleotide encoding a polypeptide having at least 70% sequence identity to a sequence selected from the group consisting of SEQ ID NOs: 1, 2, 3, 4, 5, 6, 7, 8, 9 or 10.

In a further embodiment, the nucleotide of the invention encodes a polypeptide having at least 70% sequence identity, such as 75% sequence identity, such as 80% sequence identity, such as 85% sequence identity, such as 90% sequence identity, such as 95% sequence identity, such as 96% sequence identity, such as 97% sequence identity, such as 98% sequence identity, such as 99% sequence identity, such as 100% sequence identity sequence identity to a sequence selected from the group consisting of SEQ ID NOs: 1, 2, 3, 4, 5, 6, 7, 8, 9 and 10.

In yet another embodiment, the agent of the present invention is a vector comprising the nucleic acid molecule as defined herein above.

In a further embodiment, the vector is selected from the group consisting of vectors derived from the Retroviridae family including lentivirus, HIV, SIV, FIV, EAIV, CIV.

In another embodiment, the vector is selected from the group consisting of alphavirus, adenovirus, adeno associated virus, baculovirus, HSV, coronavirus, Bovine papilloma virus, Mo-MLV, preferably adeno associated virus.

In a further embodiment, the vector comprises a promoter operably linked to the nucleic acid molecule.

In one embodiment, said promoter is selected from the group consisting of: CMV, human UbiC, RSV, Tet-regulatable promoter, Mo-MLV-LTR, Mx1, EF-1alpha, PDGF beta and CaMK II.

In one embodiment, the agent of the present invention is a cell transformed or transduced with one or more vectors as defined herein above. Said cell may be implanted into a subject in order to produce polypeptide agents according to the invention. The cells may furthermore be encapsulated into a biocompatible capsule and administered to the subject in need thereof. In this manner, the agent according to the present invention may be locally administered into the Central Nervous System, thus avoiding difficulties in passing the Blood Brain Barrier.

In one embodiment, the cell capable of producing the agent of the present invention is selected from the group consisting of *Saccharomyces cerevisiae, E. coli, Aspergillus* and Sf9 insect cells.

In another embodiment, the cell capable of producing the agent of the present invention is selected from the group consisting of mammalian cells selected from the group consisting of human, feline, porcine, simian, canine, murine and rat cells.

In a further embodiment, the mammalian cell capable of producing the agent of the present invention is selected from the group consisting of neurons and glial cells.

In an embodiment the mammalian cell is selected from the group consisting of CHO, CHO-K1, HEI193T, HEK293, COS, PC12, HiB5, RN33b and BHK cells.

In yet another embodiment, the invention relates to a packaging cell line capable of producing an infective virus particle, said virus particle comprising a Retroviridae derived genome comprising a 5' retroviral LTR, a tRNA binding site, a packaging signal, a promoter operably linked to a polynucleotide sequence encoding the polypeptide agent as defined herein above, an origin of second strand DNA synthesis, and a 3' retroviral LTR.

In a further embodiment, wherein the genome of the virus particle is lentivirally derived and the LTRs are lentiviral.

In one embodiment, the agent of the invention is capable of binding to the Vps10p-domain receptor entity of the invention. In a preferred embodiment, the agent is a Sortilin binding agent, inhibiting formation of a Sortilin:TrpV:TrkA complex.

In one such embodiment, the agent of the present invention has the general structure of formula (I):

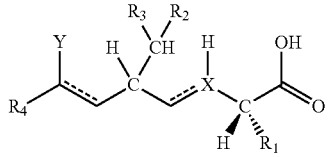

(I)

wherein X is an atom acting as hydrogen donor said atom selected from the group consisting of N, O, S, P and wherein Y is an electronegative atom acting as hydrogen bond acceptor selected from the group consisting of O, N, S, F, Cl, Br, I, and wherein $R_1$ is C3-6 alkyl, C4-6 cyclyl, a heterocyclic or a heteroaromatic structure having one ring, 4 to 6 ring members in each and 1 to 3 heteroatoms, or a heteroalkyl comprising 1 to 3 heteroatoms selected from the group consisting of N, O, $S(O)_{0-2}$, and wherein $R_2$ is a hydrogen, a C1-12 alkyl or an aromatic, a carbocyclic, a heterocyclic or a heteroaromatic structure having 1-3 rings, 3-8 ring members in each and 0 to 4 heteroatoms, or a heteroalkyl comprising 1 to 8 heteroatoms selected from the group consisting of N, O, $S(O)_{0-2}$, and wherein $R_3$ is hydrogen, SH, imidazole, C1-12 alkyl or an aromatic, a carbocyclic, a heterocyclic or a heteroaromatic structure having 1-3 rings, 3-8 ring members in each and 0 to 4 heteroatoms, or a heteroalkyl comprising 1 to 8 heteroatoms selected from the group consisting of N, O, S, and wherein $R_4$ is selected from the functional groups C1-100 linear or branched alkyl, linear or branched alkenyl, linear or branched alkynyl, phenyl, benzyl, haloalkane, chloroalkane, bromoalkane, iodoalkane, haloformyl, hydroxyl, carbonyl, aldehyde, carbonate ester, carboxylate, carboxyl, ether, ester, hydroperoxy, peroxy, carboxamide, primary amine, secondary amine, tertiary amine, ammonium, primary ketimine, secondary ketimine, primary aldimine, secondary aldimine, imide, azide, azo (diimide), cyanate, isocyanide, isothiocyanate, nitrate, nitrile, nitrosooxy, nitro, nitroso, priidyl, phosphino, phosphate, phosphono, sulfonyl, sulfinyl, sulfhydryl (SH), thiocyanate, disulfide, a linker L2 or L3, and an amino acid sequence being at least 50% identical to SEQ ID NO: 10 or a fragment thereof.

In another embodiment, the agent has the general structure of formula (II):

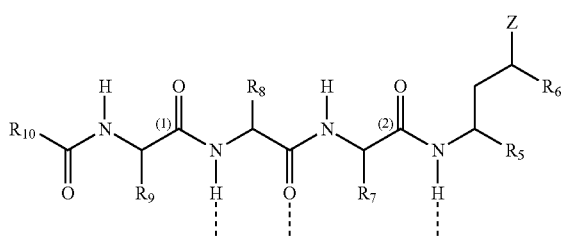

(II)

wherein Z is a hydrogen bond donor or acceptor selected from the group consisting of carbonyl, hydroxyl, amino, imino, amide, sulfhydryl, chloro, fluoro, and wherein $R_5$ is selected from the group consisting of H, $CH_3$, and a linker L2, and wherein $R_6$ is selected from the group consisting of H, $-CH_3$, $-CH_2CH_3$ and $-OCH_3$, and wherein $R_7$ is selected from the group consisting of side chains of glutamate, glutamine, lysine, arginine, histidine, tyrosine, methionine, cysteine, aliphatic C4-6 groups, and wherein $R_8$ is selected from the group consisting of side chains of tyrosine, histidine, serine, threonine, aspartate, asparagine, cysteine, phenylalanine, iodo-tyrosine and $-CH_2-NH_2$, and wherein $R_9$ is selected from the group consisting of side chain of lysine, arginine, glutamine, C3-8 aliphatic and heteroaliphatic groups, carbocyclic and heterocyclic groups comprising 5 or 6 membered rings, and wherein $R_{10}$ is selected from the group consisting of a pyroglutamate, poly-carbohydrates and a polypeptide of length greater than equal to 10, and wherein $R_{11}$ and $R_{12}$ individually are selected from the group consisting of H, C1-12 linear or branched alkyl, linear or branched alkenyl, linear or branched alkynyl, phenyl, benzyl, haloalkane, chloroalkane, bromoalkane, iodoalkane, haloformyl, hydroxyl, carbonyl, aldehyde, carbonate ester, carboxylate, carboxyl, ether, ester, hydroperoxy, peroxy, carboxamide, primary amine, secondary amine, tertiary amine, ammonium, primary ketimine, secondary ketimine, primary aldimine, secondary aldimine, imide, azide, azo (diimide), cyanate, isocyanide, isothiocyanate, nitrate, nitrile, nitrosooxy, nitro, nitroso, priidyl, phosphino, phosphate, phosphono, sulfonyl, sulfinyl, sulfhydryl (SH), and wherein the covalent bonds (1) and (2) individually are selected from the group consisting of single bonds and double bonds.

In another embodiment the agent has the general structure of formula (III):

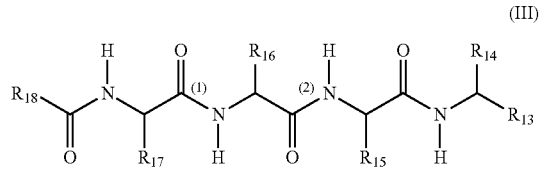

(III)

wherein $R_{13}$ is selected from the group consisting of H, C1-12 alkyl, alkenyl, alkynyl and a linker L3, and wherein $R_{14}$, $R_{15}$, $R_{17}$, $R_{19}$, $R_{20}$ individually are selected from the group consisting of H, C1-12 alkyl, alkenyl and alkynyl, and wherein $R_{16}$ is selected from the group consisting of sidechains of phenylalanine, leucine, isoleucine, valine, methionine, histidine, cysteine, lysine and aliphatic C3-7, and wherein $R_{18}$ is selected from the group consisting of H, $-CH_3$ and $-CH_2OH$, and wherein the covalent bonds (1) and (2) individually are selected from the group consisting of single bonds and double bonds.

In one embodiment, the linker L2 mentioned herein above is selected from the group consisting of a peptide backbone of 5 to 6 residues, C15-20 alkyl, C15-20 alkenyl and C15-20 alkynyl.

In a further embodiment said linker L2 links the general formula (I) to the general formula (II), thereby forming an agent having the general formula (IV):

[Formula (I)]–[Linker L2]–[Formula (II)]    (IV)

On one embodiment, the linker L3 is selected from the group consisting of a peptide backbone of 12 to 20 residues, C30-60 alkyl, C30-60 alkenyl, C30-60 alkynyl.

In a further embodiment said linker L3 links the general formula (I) to the general formula (I) to the general formula (III), thereby forming an agent having the general formula (V):

[Formula (I)]–[Linker L3]–[Formula (III)]     (V)

In one embodiment, the agent is a peptide or artificial peptide, or synthetic peptide or a mixed molecule comprising a natural and a non-natural part, said agent selected from the group consisting of peptides having the sequence RRPYI (cyclohexyl-glycine), iodoYIL, QIL, YCL, dYIL, YHL, RRPYI-1-amino-1-carboxycyclohexyl, RRPYI(n-Methyl-Leucin and YIL, depicted in FIG. 8.

In one embodiment the agent is RRPYI(cyclo-hexyl-glycine) depicted in FIG. 8.

In one embodiment the agent is iodoYIL depicted in FIG. 8.

In one embodiment the agent is QIL depicted in FIG. 8.

In one embodiment the agent is YCL depicted in FIG. 8.

In one embodiment the agent is dYIL depicted in FIG. 8.

In one embodiment the agent is YHL depicted in FIG. 8.

In one embodiment the agent is RRPYI-1-amino-1-carboxycyclohexyl depicted in FIG. 8.

In one embodiment the agent is RRPYI(n-Methyl-Leucin depicted in FIG. 8.

In one embodiment the agent is YIL depicted in FIG. 8.

Antibodies

An antibody binds tightly to a particular target molecule, thereby either inactivating it directly or marking it for destruction. The antibody recognizes its target (antigen) with remarkable specificity and strength dictated by the sum of many chemical forces, including hydrogen bonds, hydrophobic and van der Waal's forces, as well as ionic interactions. In general, the more complex the target is chemically, the more immunogenic it will be. The antigenic determinant may encompass short linear amino acid stretches or a more complicated, three-dimensional protein module.

Conceptually, antibodies directed against a target receptor may inhibit ligand binding in two ways: competitive or allosteric. Competitive inhibition involves the direct binding of the antibody to or near the ligand binding site on the receptor, thereby displacing the ligand from its receptor or sterically inhibiting the approach of the ligand to the ligand binding site. Allosteric inhibition involves the binding of the antibody to a site on the receptor polypeptide that is distinct from the ligand binding epitope. However, binding to this site will induce a conformational change in the overall structure of the receptor that makes it more difficult or even impossible for the ligand to bind to its cognate recognition site.

It is an aspect of the present invention to provide antibodies or functional equivalents thereof specifically recognising and binding epitopes of the Vps10p-domain receptors, TrpV receptors and a third component to which the previous two components of a ternary complex may bind. An example of a third epitope is the TrkA receptor.

The antibody or functional equivalent thereof may be any antibody known in the art, for example a polyclonal or a monoclonal antibody derived from a mammal or a synthetic antibody, such as a single chain antibody or hybrids comprising antibody fragments. Furthermore, the antibody may be mixtures of monoclonal antibodies or artificial polyclonal antibodies. In addition functional equivalents of antibodies may be antibody fragments, in particular epitope binding fragments. Furthermore, antibodies or functional equivalent thereof may be a small molecule mimicking? an antibody. Naturally occurring antibodies are immunoglobulin molecules consisting of heavy and light chains. In preferred embodiments of the invention, the antibody is a monoclonal antibody.

Monoclonal antibodies (Mab's) are antibodies, wherein every antibody molecule are similar and thus recognises the same epitope. Monoclonal antibodies are in general produced by a hybridoma cell line. Methods of making monoclonal antibodies and antibody-synthesizing hybridoma cells are well known to those skilled in the art. Antibody producing hybridomas may for example be prepared by fusion of an antibody producing B lymphocyte with an immortalized B-lymphocyte cell line. Monoclonal antibodies according to the present invention may for example be prepared as described in Antibodies: A Laboratory Manual, By Ed Harlow and David Lane, *Cold Spring Harbor Laboratory Press*, 1988. Said monoclonal antibodies may be derived from any suitable mammalian species, however frequently the monoclonal antibodies will be rodent antibodies for example murine or rat monoclonal antibodies. It is preferred that the antibodies according to the present invention are monoclonal antibodies or derived from monoclonal antibodies.

Polyclonal antibodies is a mixture of antibody molecules recognising a specific given antigen, hence polyclonal antibodies may recognise different epitopes within said antigen. In general polyclonal antibodies are purified from serum of a mammal, which previously has been immunized with the antigen. Polyclonal antibodies may for example be prepared by any of the methods described in Antibodies: A Laboratory Manual, By Ed Harlow and David Lane, *Cold Spring Harbor Laboratory Press*, 1988. Polyclonal antibodies may be derived from any suitable mammalian species, for example from mice, rats, rabbits, donkeys, goats, sheeps, cows or camels. The antibody is preferably not derived from a non-mammalian species, i.e. the antibody is for example preferably not a chicken antibody. The antibody may also for example be an artificial polyclonal antibody as for example described in U.S. Pat. Nos. 5,789,208 or 6,335,163, both patent specifications are hereby incorporated by reference into the application in their entirety.

The antibodies according to the present invention may also be recombinant antibodies. Recombinant antibodies are antibodies or fragments thereof or functional equivalents thereof produced using recombinant technology. For example recombinant antibodies may be produced using a synthetic library or by phage display. Recombinant antibodies may be produced according to any conventional method for example the methods outlined in "Recombinant Antibodies", Frank Breitling, Stefan Dübel, Jossey-Bass, September 1999.

The antibodies according to the present invention may also be bispecific antibodies, i.e. antibodies specifically recognising two different epitopes. Bispecific antibodies may in general be prepared starting from monoclonal antibodies, or from recombinant antibodies, for example by fusing two hybridoma's in order to combine their specificity, by Chemical crosslinking or using recombinant technologies. Anti-bodies according to the present invention may also be tri-specific antibodies.

Functional equivalents of antibodies may in one preferred embodiment be a fragment of an antibody, preferably an antigen binding fragment or a variable region. Examples of antibody fragments useful with the present invention include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments which are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

Preferred antibody fragments retain some or essential all the ability of an antibody to selectively binding with its antigen or receptor. Some preferred fragments are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule and can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association (V$_H$-V$_L$ dimer). It is in this configuration that the three CDRs of each variable domain interact to define an antigen binding site on the surface of the V$_H$-V$_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

In one embodiment of the present invention the antibody is a single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "scFv" antibody fragments. Generally, the Fv polypeptide further comprises a polypeptide linker between the VH and VL domains that enables the scFv to form the desired structure for antigen binding.

In another embodiment of the present invention the functional equivalent of an antibody is a small molecule mimicking an antibody. Such molecules may be a non-immunoglobulin binding members. Thus the epitope polypeptide of the present invention binding may be derived from a naturally occurring protein or polypeptide; said protein or polypeptide may for example be designed de novo, or may be selected from a library. The binding member may be a single moiety, e.g., a polypeptide or protein domain, or it may include two or more moieties, e.g., a pair of polypeptides such as a pair polypeptides. The binding polypeptide may for example, but not exclusively, be a lipocalin, a single chain MHC molecule, an Anticalin™ (Pieris), an Affibody™, or a Trinectin™ (Phy-los), Nanobodies (Ablynx). The binding member may be selected or designed by recombinant methods known by people well known in the art.

Human Antibodies

Human monoclonal antibodies of the invention can be produced by a variety of techniques, including conventional monoclonal antibody methodology, e.g., the standard somatic cell hybridization technique of Kohler and Milstein, *Nature* 256:495 (1975). Although somatic cell hybridization procedures are preferred, in principle, other techniques for producing monoclonal antibody can be employed, e.g., viral or oncogenic transformation of B-lymphocytes or phage display techniques using libraries of human antibody genes.

Binding Epitopes for Antibodies on the Vps10p-domain Receptor Sortilin

In one preferred embodiment, the agent of the present invention is an antibody selected from the group consisting of: polyclonal antibodies, monoclonal antibodies, humanised antibodies, single chain antibodies, recombinant antibodies, antibody fragments including Fab fragments.

In a preferred embodiment the antibody is directed against an extracellular part of the Vps10p-domain receptor. This embodiment is useful both in vivo and in vitro.

In another embodiment, the antibody agent of the present invention is directed to the intracellular domain of the Vps10p-domain receptor. This embodiment is particularly useful for in vitro purposes.

In another embodiment, the Vps10p-domain receptor is selected from the group consisting of Sortilin (SEQ ID NO: 1), SorLA (SEQ ID NO: 2), SorCS1 (SEQ ID NO: 3), SorCS2 (SEQ ID NO: 4) and SorCS3 (SEQ ID NO: 5).

In a preferred embodiment the Vps10p-domain receptor is Sortilin (SEQ ID NO: 1).

In one embodiment, human monoclonal antibodies are directed against an epitope comprising amino acid residues R325, S316, Y351, I353, K260, I327, F314, F350 to M363, S305, F306, T398 to G400, I303-G309, Q349-A356, Y395 and T402 of SEQ ID NO. 1 or a soluble or membrane bound fragment or variant thereof.

In another embodiment, human monoclonal antibodies are directed against an epitope comprising amino acid residues R325, S316, Y351, I353, K260, I327, F314, F350 to M363, S305, F306 and T398 to G400 of SEQ ID NO. 1 or a soluble or membrane bound fragment or variant thereof.

In another embodiment, human monoclonal antibodies are directed against an epitope comprising amino acid residues R325, S316, Y351, I353, K260, I327, F314 and F350 to M363 of SEQ ID NO. 1 or a soluble or membrane bound fragment or variant thereof.

In another embodiment, human monoclonal antibodies are directed against an epitope comprising amino acid residues L572, L114, V112, R109 to S111, S115 to G118, T570, G571, W586, W597, T168-I174, L572, A573 and S584 to F588 of SEQ ID NO. 1 or a soluble or membrane bound fragment or variant thereof.

In another embodiment, human monoclonal antibodies are directed against an epitope comprising amino acid residues L572, L114, V112, R109 to S111, S115 to G118, T570, G571, W586 and W597 of SEQ ID NO. 1 or a soluble or membrane bound fragment or variant thereof.

In another embodiment, human monoclonal antibodies are directed against an epitope comprising amino acid residues L572, L114 and V112 of SEQ ID NO. 1.

In another embodiment, human monoclonal antibodies are directed against an epitope comprising amino acid residues D403, S420, D422, N423, S424, I425, E426, T451, Y466, E470, I498, S499 and V500 of SEQ ID NO. 1 or a soluble or membrane bound fragment or variant thereof.

In another embodiment, human monoclonal antibodies are directed against an epitope comprising amino acid residues D403, N423, S424, I425, T451, Y466, I498 and V500 of SEQ ID NO. 1 or a soluble or membrane bound fragment or variant thereof.

In another embodiment, human monoclonal antibodies are directed against an epitope comprising amino acid residues T451, Y466, I498 and V500 of SEQ ID NO. 1 or a soluble or membrane bound fragment or variant thereof.

In one important embodiment, the antibody of the present invention is selected from the antibodies described in table 1.

Accordingly, the antibodies of the present invention may be selected from, but are not limited to antibodies selected from the group consisting of goat anti-extracellular domain of human SorLA antibody, rabbit anti-cytoplasmic domain of human SorLA antibody, rabbit anti-complementary repeat of human SorLA antibody, rabbit anti-extracellular domain of human SorLA antibody, rabbit anti-cytoplasmic domain of human SorLA antibody, rabbit anti-Vps10p-domain of human SorLA antibody, rabbit anti-peptide sequence in Vps10p-domain of human SorLA antibody, rabbit anti-C-terminal of human SorLA antibody, rabbit anti-Cytoplasmic tail of human SorLA antibody, mouse anti-Extracellular domain of human SorLA antibody, rabbit anti-Extracellular domain of human Sortilin antibody, rabbit anti-cytoplasmic domain of human Sortilin antibody, rabbit anti-propeptide of human Sortilin antibody, rabbit anti Vps10p-domain of human Sortilin antibody, goat anti-Extracellular domain of human Sortilin, mouse anti-Extracellular domain of human Sortilin antibody, goat anti-Extracellular domain of human SorCS1 antibody, rabbit anti-Extracellular domain of human SorCS1 antibody, rabbit anti-Leucine rich domain of human SorCS1 antibody, mouse anti-Extracellular domain of human SorCS1 antibody, sheep anti-Extracellular domain of human SorCS2 antibody, goat anti-Extracellular domain of human SorCS2 antibody, rabbit anti-Extracellular domain of human SorCS2 antibody, rabbit anti-28 C-terminal amino acids of human SorCS2 antibody, rabbit anti-propeptide of human SorCS2 antibody, mouse anti-Extracellular domain of human SorCS2, rabbit anti-15 C-terminal amino acids of human SorCS3 antibody, rabbit anti-N-terminal domain of human SorCS3 antibody, rabbit anti-Extracellular domain of human SorCS3, mouse anti-Extracellular domain of human SorCS3 and goat anti-Extracellular domain of human SorCS3 antibody, or a combination of the above.

In one embodiment, the antibody is directed against the TrpV receptor.

In a further embodiment, the antibody is directed against the TrkA receptor.

The person skilled in the art of producing antibodies, may, based on the information provided above, at his or her discretion produce an antibody capable of inhibiting pain according to the present invention Immunizations To generate fully human monoclonal antibodies to the epitopes of interest to the present invention, transgenic or transchromosomal mice containing human immunoglobulin genes (e.g., HCo12, HCo7 or KM mice) can be immunized with an enriched preparation of the antigen and/or cells expressing the epitopes of the receptor targets of the present invention, as described, for example, by Lonberg et al. (1994), supra; Fishwild et al. (1996), supra, and WO 98/24884. Alternatively, mice can be immunized with DNA encoding the CaOU-1 epitope. Preferably, the mice will be 6-16 weeks of age upon the first infusion.

Cumulative experience with various antigens has shown that the HuMAb transgenic mice respond best when initially immunized intraperitoneally (i.p.) or subcutaneously (s.c.) with antigen expressing cells in complete Freund's adjuvant, followed by every other week i.p. immunizations (up to a total of 10) with the antigen expressing cells in PBS. The immune response can be monitored over the course of the immunization protocol with plasma samples being obtained by retro-orbital bleeds. The plasma can be screened by FACS analysis, and mice with sufficient titers of anti-antigen human immunoglobulin can be used for fusions. Mice can be boosted intravenously with antigen expressing cells for example 4 and 3 days before sacrifice and removal of the spleen.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; and Queen, C. et al. (1989) *Proc. Natl. Acad. Sci. USA* 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody which contains mutations throughout the variable gene but typically clustered in the CDRs. For example, somatic mutations are relatively infrequent in the amino terminal portion of framework region 1 and in the carboxy-terminal portion of framework region 4. For this reason, it is not necessary to obtain the entire DNA sequence of a particular antibody in order to recreate an intact recombinant antibody having binding properties similar to those of the original antibody (see WO 99/45962). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266:19867-19870); and HindIII sites are engineered upstream of the translation initiation sites.

For both the heavy and light chain variable regions, the optimized coding and corresponding non-coding, strand sequences are broken down into 30-50 nucleotides approximately at the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region (including the BbsI site of the kappa light chain, or the AgeI site of the gamma heavy chain) in the PCR amplification to generate fragments that can easily be cloned into the expression vector constructs.

The reconstructed heavy and light chain variable regions are then combined with cloned promoter, leader, translation initiation, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Monovalent Antibodies

The monospecific binding polypeptide may be monovalent, i.e. having only one binding domain.

For a monovalent antibody, the immunoglobulin constant domain amino acid residue sequences comprise the structural portions of an antibody molecule known in the art as CH1, CH2, CH3 and CH4. Preferred are those binding polypeptides which are known in the art as $C_L$. Preferred $C_L$ polypeptides are selected from the group consisting of $C_{kappa}$ and $C_{lambda}$.

Furthermore, insofar as the constant domain can be either a heavy or light chain constant domain ($C_H$ or $C_L$, respectively), a variety of monovalent binding polypeptide compositions are contemplated by the present invention. For example, light chain constant domains are capable of disulfide bridging to either another light chain constant domain, or to a heavy chain constant domain. In contrast, a heavy chain constant domain can form two independent disulfide bridges, allowing for the possibility of bridging to both another heavy chain and to a light chain, or to form polymers of heavy chains.

Thus, in another embodiment, the invention contemplates an isolated monovalent binding polypeptide wherein the constant chain domain C has a cysteine residue capable of forming at least one disulfide bridge, and where at least two monovalent polypeptides are covalently linked by said disulfide bridge.

In preferred embodiments, the constant chain domain C can be either $C_L$ or $C_H$. Where C is $C_L$, the $C_L$ polypeptide is preferably selected from the group consisting of $C_{kappa}$ and $C_{lambda}$.

In another embodiment, the invention contemplates a binding polypeptide composition comprising a monovalent polypeptide as above except where C is $C_L$ having a cysteine residue capable of forming a disulfide bridge, such that the composition contains two monovalent polypeptides covalently linked by said disulfide bridge.

Multispecificity, Including Bispecificity

In a preferred embodiment the present invention relates to multispecific binding polypeptides, which have affinity for and are capable of binding at least two different entities. Multispecific binding polypeptides can include bispecific binding polypeptides.

In one embodiment the multispecific molecule is a bispecific antibody (BsAb), which carries at least two different binding domains, where preferably at least one of which is of antibody origin.

A bispecific molecule of the invention can also be a single chain bispecific molecule, such as a single chain bispecific antibody, a single chain bispecific molecule comprising one single chain antibody and a binding domain, or a single chain bispecific molecule comprising two binding domains. Multispecific molecules can also be single chain molecules or may comprise at least two single chain molecules.

The multispecific, including bispecific, antibodies may be produced by any suitable manner known to the person skilled in the art.

The traditional approach to generate bispecific whole antibodies was to fuse two hybridoma cell lines each producing an antibody having the desired specificity. Because of the random association of immunoglobulin heavy and light chains, these hybrid hybridomas produce a mixture of up to 10 different heavy and light chain combinations, only one of which is the bispecific antibody. Therefore, these bispecific antibodies have to be purified with cumbersome procedures, which considerably decrease the yield of the desired product.

Alternative approaches include in vitro linking of two antigen specificities by chemical cross-linking of cysteine residues either in the hinge or via a genetically introduced C-terminal Cys as described above. An improvement of such in vitro assembly was achieved by using recombinant fusions of Fab's with peptides that promote formation of heterodimers. However, the yield of bispecific product in these methods is far less than 100%.

A more efficient approach to produce bivalent or bispecific antibody fragments, not involving in vitro chemical assembly steps, was described by Holliger et al. (1993). This approach takes advantage of the observation that scFv's secreted from bacteria are often present as both monomers and dimers. This observation suggested that the $V_H$ and $V_L$ of different chains could pair, thus forming dimers and larger complexes. The dimeric antibody fragments, also named "diabodies" by Holliger et al., are in fact small bivalent antibody fragments that assembled in vivo. By linking the $V_H$ and $V_L$ of two different antibodies 1 and 2, to form "cross-over" chains $V_H1V_L2$ and $V_H2$-$V_L1$, the dimerisation process was shown to reassemble both antigen-binding sites. The affinity of the two binding sites was shown to be equal to the starting scFv's, or even to be 10-fold increased when the polypeptide linker covalently linking $V_H$ and $V_L$ was removed, thus generating two proteins each consisting of a $V_H$ directly and covalently linked to a $V_L$ not pairing with the $V_H$. This strategy of producing bispecific antibody fragments was also described in several patent applications. Patent application WO 94/09131 (SCOTGEN LTD; priority date Oct. 15, 1992) relates to a bispecific binding protein in which the binding domains are derived from both a $V_H$ and a $V_L$ region either present at two chains or linked in an scFv, whereas other fused antibody domains, e.g. C-terminal constant domains, are used to stabilise the dimeric constructs. Patent application WO 94/13804 (CAMBRIDGE ANTIBODY TECHNOLOGY/ MEDICAL RESEARCH COUNCIL; first priority date Dec. 4, 1992) relates to a polypeptide containing a $V_H$ and a $V_L$ which are incapable of associating with each other, whereby the V-domains can be connected with or without a linker.

Mallender and Voss, 1994 (also described in patent application WO 94/13806; DOW CHEMICAL CO; priority date Dec. 11, 1992) reported the in vivo production of a single-chain bispecific antibody fragment in *E. coli*. The bispecificity of the bivalent protein was based on two previously produced monovalent scFv molecules possessing distinct specificities, being linked together at the genetic level by a flexible polypeptide linker. Traditionally, whenever single-chain antibody fragments are referred to, a single molecule consisting of one heavy chain linked to one (corresponding) light chain in the presence or absence of a polypeptide linker is implicated. When making bivalent or bispecific antibody fragments through the "diabody" approach (Holliger et al., (1993) and patent application WO 94/09131) or by the "double scFv" approach (Mallender and Voss, 1994 and patent application WO 94/13806), again the $V_H$ is linked to a (the corresponding) $V_L$.

The multispecific molecules described above can be made by a number of methods. For example, all specificities can be encoded in the same vector and expressed and assembled in the same host cell. This method is particularly useful where the multispecific molecule is a mAb×mAb, mAb×Fab, Fab× F(ab')$_2$ or ligand×Fab fusion protein. Various other methods for preparing bi- or multivalent antibodies are described for example described in U.S. Pat. Nos. 5,260,203; 5,455,030; 4,881,175; 5,132,405; 5,091,513; 5,476,786; 5,013,653; 5,258,498; and 5,482,858.

By using a bispecific or multispecific binding polypeptide according to the invention the invention offers several advantages as compared to monospecific/monovalent binding polypeptides.

It may be preferred that the at least one other binding domain is capable of binding an immunoactive cell, such as a leucocyte, a macrophage, a lymphocyte, a basophilic cell, and/or an eosinophilic cell, in order to increase the effect of the binding polypeptide in a therapeutic method. This may be accomplished by establishing that the at least one other binding domain is capable of specifically binding a mammalian protein, such as a human protein, such as a protein selected from any of the cluster differentiation proteins (CD), in particular CD64 and/or CD89. A method for producing bispecific antibodies having CD64 specificity is described in U.S. Pat. No. 6,071,517 to Medarex, Inc.

The production and characterization of these preferred monoclonal antibodies are described by Fanger et al. in WO 88/00052 and in U.S. Pat. No. 4,954,617. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. In other embodiments, the anti-Fcγ receptor antibody is a humanized form of mAb 22 (H22). The production and characterization of the H22 antibody is described in Graziano, R. F. et al. (1995) *J. Immunol.* 155 (10):4996-5002 and WO 94/10332. The H22 antibody producing cell line was deposited at the American Type Culture Collection on Nov. 4, 1992 under the designation HA022CL1 and has the accession No. CRL 11177.

In still other preferred embodiments, the binding specificity for an Fc receptor is provided by an antibody that binds to a human IgA receptor, e.g., an Fcα receptor (FcαI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148:1764).

FcαRI, FcγRI, FcγRII and FcγRIII, especially FcγRII and FcγRIII, are preferred trigger receptors for use in the invention because they (1) are expressed primarily on immune effector cells, e.g., monocytes, PMNs, macrophages and dendritic cells; (2) are expressed at high levels (e.g., 5,000-100,000 per cell); (3) are mediators of cytotoxic activities (e.g., ADCC, phagocytosis); and (4) mediate enhanced antigen presentation of antigens, including self-antigens, targeted to them.

While human monoclonal antibodies are preferred, other antibodies which can be employed in the bispecific or multispecific molecules of the invention are murine, chimeric and humanized monoclonal antibodies. Such murine, chimeric and humanized monoclonal antibodies can be prepared by methods known in the art.

Bispecific and multispecific molecules of the present invention can be made using chemical techniques (see e.g., D. M. Kranz et al. (1981) *Proc. Natl. Acad. Sci. USA* 78:5807), "polydoma" techniques (see U.S. Pat. No. 4,474,893), or recombinant DNA techniques.

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific and multispecific molecule is a mAb×mAb, mAb×Fab, Fab× F(ab')$_2$ or ligand×Fab fusion protein. A bispecific and multispecific molecule of the invention, e.g., a bispecific molecule can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing bi- and multispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific and multispecific molecules to their specific targets can be confirmed by enzyme-linked immunosorbent assay (ELISA), a radioimmunoassay (RIA), FACS analysis, a bioassay (e.g., growth inhibition), or a Western Blot Assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a γ counter or a scintillation counter or by autoradiography.

Humanised Antibody Framework

It is not always desirable to use non-human antibodies for human therapy, since the non-human "foreign" epitopes may elicit immune response in the individual to be treated. To eliminate or minimize the problems associated with non-human antibodies, it is desirable to engineer chimeric antibody derivatives, i.e., "humanized" antibody molecules that combine the non-human Fab variable region binding determinants with a human constant region (Fc). Such antibodies are characterized by equivalent antigen specificity and affinity of the monoclonal and polyclonal antibodies described above, and are less immunogenic when administered to humans, and therefore more likely to be tolerated by the individual to be treated.

Accordingly, in one embodiment the binding polypeptide has a binding domain carried on a humanised antibody framework, also called a humanised antibody.

Humanised antibodies are in general chimeric antibodies comprising regions derived from a human antibody and regions derived from a non-human antibody, such as a rodent antibody. Humanisation (also called Reshaping or CDR-grafting) is a well-established technique for reducing the immunogenicity of monoclonal antibodies (mAbs) from xenogeneic sources (commonly rodent), increasing the homology to a human immunoglobulin, and for improving their activation of the human immune system. Thus, humanized antibodies are typically human antibodies in which some CDR residues and possibly some framework residues are substituted by residues from analogous sites in rodent antibodies.

It is further important that humanized antibodies retain high affinity for the antigen and other favourable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of certain residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is maximized, although it is the CDR residues that directly and most substantially influence antigen binding.

One method for humanising MAbs related to production of chimeric antibodies in which an antigen binding site comprising the complete variable domains of one antibody are fused to constant domains derived from a second antibody, preferably a human antibody. Methods for carrying out such chimerisation procedures are for example described in EP-A-0 120 694 (Celltech Limited), EP-A-0 125 023 (Genentech Inc.), EP-A-0 171 496 (Res. Dev. Corp. Japan), EP-A-0173494 (Stanford University) and EP-A-0 194 276 (Celltech Limited). A more complex form of humanisation of an antibody involves the re-design of the variable region domain so that the amino acids constituting the non-human antibody binding site are integrated into the framework of a human antibody variable region (Jones et al., 1986).

The humanized antibody of the present invention may be made by any method capable of replacing at least a portion of a CDR of a human antibody with a CDR derived from a non-human antibody. Winter describes a method which may be used to prepare the humanized antibodies of the present invention (UK Patent Application GB 2188638A, filed on Mar. 26, 1987), the contents of which is expressly incorporated by reference. The human CDRs may be replaced with non-human CDRs using oligonucleotide site-directed mutagenesis as described in the examples below.

As an example the humanized antibody of the present invention may be made as described in the brief explanation below. The humanized antibodies of the present invention may be produced by the following process:

(a) constructing, by conventional techniques, an expression vector containing an operon with a DNA sequence encoding an antibody heavy chain in which the CDRs and such minimal portions of the variable domain framework region that are required to retain antibody binding specificity are derived from a non-human immunoglobulin, and the remaining parts of the antibody chain are derived from a human immunoglobulin, thereby producing the vector of the invention;

(b) constructing, by conventional techniques, an expression vector containing an operon with a DNA sequence encoding a complementary antibody light chain in which the CDRs and such minimal portions of the variable domain framework region that are required to retain donor antibody binding specificity are derived from a non-human immunoglobulin, and the remaining parts of the antibody chain are derived from a human immunoglobulin, thereby producing the vector of the invention;

(c) transfecting the expression vectors into a host cell by conventional techniques to produce the transfected host cell of the invention; and (d) culturing the transfected cell by conventional techniques to produce the humanised antibody of the invention.

The host cell may be cotransfected with the two vectors of the invention, the first vector containing an operon encoding a light chain derived polypeptide and the second vector containing an operon encoding a heavy chain derived polypeptide. The two vectors contain different selectable markers, but otherwise, apart from the antibody heavy and light chain coding sequences, are preferably identical, to ensure, as far as possible, equal expression of the heavy and light chain polypeptides. Alternatively, a single vector may be used, the vector including the sequences encoding both the light and the heavy chain polypeptides. The coding sequences for the light and heavy chains may comprise cDNA or genomic DNA or both.

The host cell used to express the altered antibody of the invention may be either a bacterial cell such as *E. coli*, or a eukaryotic cell. In particular a mammalian cell of a well defined type for this purpose, such as a myeloma cell or a Chinese hamster ovary cell may be used.

The general methods by which the vectors of the invention may be constructed, transfection methods required to produce the host cell of the invention and culture methods required to produce the antibody of the invention from such host cells are all conventional techniques. Likewise, once produced, the humanized antibodies of the invention may be purified according to standard procedures as described below.

Human Antibody Framework

In a more preferred embodiment the invention relates to a binding polypeptide, wherein the binding domain is carried by a human antibody framework, i.e. wherein the antibodies have a greater degree of human peptide sequences than do humanised antibodies.

Human mAb antibodies directed against human proteins can be generated using transgenic mice carrying the complete human immune system rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immunol 7:33-40; Tuaillon et al. 1993 PNAS 90:3720-3724; Bruggeman et al. 1991 Eur J Immunol 21:1323-1326).

Such transgenic mice are available from Abgenix, Inc., Fremont, Calif., and Medarex, Inc., Annandale, N.J. It has been described that the homozygous deletion of the antibody heavy-chain joining region (1H) gene in chimeric and germline mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA 90:2551 (1993); Jakobovits et al., Nature 362:255-258 (1993); Bruggermann et al., Year in Immunol. 7:33 (1993); and Duchosal et al. Nature 355:258 (1992). Human antibodies can also be derived from phage-display libraries (Hoogenboom et al., J. Mol. Biol. 227: 381 (1991); Marks et al., J. Mol. Biol. 222:581-597 (1991); Vaughan, et al., Nature Biotech 14:309 (1996)).

The inventors of this application have raised antibodies against several parts of the Vps10p-domain receptors. In one embodiment, the present invention is directed to antibodies against the common feature of this receptor family—the Vps10p domain.

TABLE 1

Antibodies against Vps10p-domain receptors

| Receptor | Name | Antigen | Species | Western | IH/IC | Ref. |
| --- | --- | --- | --- | --- | --- | --- |
| SorLA | SORLA goat | extracellular domain | goat | X | X | Schmidt et. al., J. Biol. Chem. 282: 32956-67, 2007 |
|  | Hale SORLA | Cytoplasmic domain | rabbit | X |  |  |
|  | SORLA LA | Complement type repeat | rabbit | X |  |  |
|  | Sol SORLA | extracellular domain | rabbit | X | X | Andersen et al., PNAS 103: 13461-6, 2005 |
|  | SORLA tail | Cytoplasmic domain | rabbit | X |  |  |
|  | SORLA VPS | VPS10p domain | rabbit | X |  |  |
|  | #606870 | Peptide seq. in Vps10p-domain | rabbit | X |  |  |
|  | #642739 | C-terminal | rabbit | X |  |  |
|  | #643739 | Cytoplasmic tail | rabbit | X |  |  |
|  | 20C11 | Extracellular domain | mouse | X | X |  |
|  | AG4 | Extracellular domain | mouse | X |  |  |
| Sortilin | #5264 | Extracellular domain | rabbit | X | X | Munck Petersen et al, EMBO J. 18: 595-604, 1999 |
|  | #5448 | Cytoplasmic domain | rabbit | X | X | Jansen et al, Nature Neurosci. 10: 1449-1457, 2007 |
|  | #5287 | Cytoplasmic domain | rabbit | X |  |  |
|  | CP 96 334 SR 96 204 | propeptide | Rabbit | X |  | Munck Petersen et al, EMBO J. 18: 595-604, 1999 |

TABLE 1-continued

| Antibodies against Vps10p-domain receptors | | | | | | |
|---|---|---|---|---|---|---|
| Receptor | Name | Antigen | Species | Western | IH/IC | Ref. |
| | #5438 | Vps10p | rabbit | X | | |
| | Sortilin goat/Laika | Extracellular domain | goat | X | | |
| | F9 | Extracellular domain | mouse | X | X | |
| | F11 | Extracellular domain | mouse | X | X | |
| | AF2934 | Extracellular domain | goat | X | X | R&D Systems, Jansen et al, Nature Neurosci. 10: 1449-1457, 2007 |
| | AF3154 | Extracellular domain | goat | X | X | R&D Systems; Jansen et al, Nature Neurosci. 10: 1449-1457, 2007 |
| | anti-NTR3 | Extracellular domain | mouse | X | X | BD Transduction Laboratories, |
| | ANT-009 | Extracellular domain | mouse | X | X | Alomone Labs; Nykjaer et al, Nature 427: 843-848, 2004 |
| SorCS1 | AF3457 | Extracellular domain | goat | X | X | BD Transduction Laboratories |
| | SorCS1 goat | Extracellular domain | goat | X | | |
| | L-SorCS1 | Extracellular domain | rabbit | X | X | Hermey et al, J. Biol. Chem. 279: 50221-50229, 2003 |
| | Leu-SorCS1 | Leucine-rich domain | rabbit | X | X | Hermey et al, J. Biol. Chem. 279: 50221-50229, 2003 |
| | #5466 | Extracellular domain | rabbit | X | X | |
| | 1D | Extracellular domain | mouse | X | | |
| | 4H | Extracellular domain | mouse | X | | |
| | 6B | Extracellular domain | mouse | X | | |
| | 4A | Extracellular domain | mouse | X | | |
| SorCS2 | AF4237 | Extracellular domain | sheep | X | | BD Transduction Laboratories |
| | SorCS2 goat | Extracellular domain | goat | X | X | |
| | #5422 | Extracellular domain | rabbit | X | X | Hermey et al, Biochem. J., 395: 285-93, 2006 |
| | #5431 | 28 C-terminal amino acids | rabbit | X | X | |
| | SorCS2-prp | propeptide | rabbit | X | | Schousboe Sjoegaard, Dissertation, Aarhus University, 2005 |
| | M1 | Extracellular domain | mouse | | X | Roland Holst, Master of Science Thesis, Aarhus University, 2006 |
| | M3 | Extracellular domain | mouse | | X | Roland Holst, Master of Science Thesis, Aarhus |

TABLE 1-continued

Antibodies against Vps10p-domain receptors

| Receptor | Name | Antigen | Species | Western | IH/IC | Ref. |
|---|---|---|---|---|---|---|
| | M4 | Extracellular domain | mouse | | X | University, 2006<br>Roland Holst, Master of Science Thesis, Aarhus University, 2006 |
| | M7 | Extracellular domain | mouse | | X | Roland Holst, Master of Science Thesis, Aarhus University, 2006 |
| | M9 | Extracellular domain | mouse | | X | Roland Holst, Master of Science Thesis, Aarhus University, 2006 |
| | M10 | Extracellular domain | mouse | | X | Roland Holst, Master of Science Thesis, Aarhus University, 2006 |
| | M13 | Extracellular domain | mouse | X | | Roland Holst, Master of Science Thesis, Aarhus University, 2006 |
| | M15 | Extracellular domain | mouse | | X | Roland Holst, Master of Science Thesis, Aarhus University, 2006 |
| | M18 | Extracellular domain | mouse | X | X | Roland Holst, Master of Science Thesis, Aarhus University, 2006 |
| | M19 | Extracellular domain | mouse | X | X | Roland Holst, Master of Science Thesis, Aarhus University, 2006 |
| | S21 | Extracellular domain | mouse | X | | Roland Holst, Master of Science Thesis, Aarhus University, 2006 |
| | SorCS2-GST-73aa | Extracellular domain | rabbit | X | | |
| | SorCS2-GST-100aa | Extracellular domain | rabbit | X | | |
| | SorCS2-GST-172aa | Extracellular domain | rabbit | X | | |
| SorCS3 | SorCS3-N | extracellular domain | rabbit | X | | |
| | SorCS3-C | 15 C-terminal aa | rabbit | X | | |
| | Sort3 N Term #5389 | N-terminal domain | rabbit | X | X | Westergaard et al, FEBS Lett. 579: 1172-6, 2005 |
| | #5432 | Extracellular domain | rabbit | X | X | |

TABLE 1-continued

Antibodies against Vps10p-domain receptors

| Receptor | Name | Antigen | Species | Western | IH/IC | Ref. |
|---|---|---|---|---|---|---|
| | MAB3067 | Extracellular domain | mouse | X | | BD Transduction Laboratories |
| | MAB30671 | Extracellular domain | mouse | X | | BD Transduction Laboratories |
| | AF3326 | Extracellular domain | goat | X | | BD Transduction Laboratories |
| | SorCS3 goat | Extracellular domain | goat | X | | |

In one embodiment, the agent of the present invention is an antibody selected from the group consisting of TrpV1 antibodies listed in table 2.

TABLE 2

Antibodies against TrpV1 receptors

| Receptor | Name | Antigen | Species | Western | IH/IC | Ref. |
|---|---|---|---|---|---|---|
| TrpV1 | Ab10296 | Extracellular domain | Rabbit | X | X | Abcam |
| | Ab72142 | Extracellular domain | Rabbit | X | X | Abcam |
| | Ab72173 | Extracellular domain | Rabbit | X | X | Abcam |
| | Ab3487 | Extracellular domain | Rabbit | X | X | Abcam |
| | AF3066 | Extracellular domain | Goat | X | X | R&D Systems |
| | Sc20813 | Extracellular domain | Rabbit | X | X | Santa Cruz Biotechnology |
| | Sc12400 | Extracellular domain | Goat | X | X | Santa Cruz Biotechnology |
| | Sc12498 | Extracellular domain | Goat | X | X | Santa Cruz Biotechnology |
| | Sc28759 | Extracellular domain | rabbit | X | X | Santa Cruz Biotechnology |

In another embodiment, the agent of the present invention is an antibody selected from the group consisting of TrkA antibodies listed in table 3.

TABLE 3

Antibodies against TrkA

| Receptor | Name | Antigen | Species | Western | IH/IC | Ref. |
|---|---|---|---|---|---|---|
| TrkA | 250893 | Extracellular domain | Rabbit | X | X | ABBIOTEC |
| | Ab43416 | Extracellular domain | Mouse | X | X | Abcam |
| | Ab72122 | Extracellular domain | Rabbit | X | X | Abcam |
| | Ab8871 | Extracellular domain | Rabbit | X | X | Abcam |
| | Ab36961 | Extracellular domain | Rabbit | X | X | Abcam |
| | Ab72162 | Extracellular domain | Rabbit | X | X | Abcam |
| | AB72160 | Extracellular domain | rabbit | X | X | Abcam |
| | Sc20539 | Extracellular domain | Goat | X | X | Santa Cruz Biotechnoly |
| | Sc14024 | Extracellular domain | Rabbit | X | X | Santa Cruz Biotechnoly |
| | Sc80961 | Extracellular domain | Mouse | X | X | Santa Cruz Biotechnoly |
| | Sc20537 | Extracellular domain | goat | X | X | Santa Cruz Biotechnoly |
| | Sc80398 | Extracellular domain | mouse | X | X | Santa Cruz Biotechnoly |
| | Sc80399 | Extracellular domain | mouse | X | X | Santa Cruz Biotechnoly |
| | MAB175 | Extracellular domain | Mouse | X | X | R&D systems |
| | AF175 | Extracellular domain | goat | X | X | R&D systems |
| | MAB1751 | Extracellular domain | Mouse | X | X | R&D systems |
| | AF1056 | Extracellular domain | Goat | X | X | R&D systems |
| | BAF1056 | Extracellular domain | Goat | X | X | R&D systems |
| | MAB1056 | Extracellular domain | mouse | X | X | R&D systems |

Generic Use of an Antibody to Inhibit Binding of a Ligand

An antibody binds tightly to a particular target molecule, thereby either inactivating it directly or marking it for destruction. The antibody recognizes its target (antigen) with remarkable specificity and strength dictated by the sum of many chemical forces, including hydrogen bonds, hydrophobic and van der Waal's forces, as well as ionic interactions. In general, the more complex the target is chemically, the more immunogenic it will be. The antigenic determinant may encompass short linear amino acid stretches or a more complicated, three-dimensional protein module.

Procedures for Making Antibodies

Polyclonal and monoclonal antibodies directed against a specific antigen, or epitope of an antigen, can be produced according to standard procedures (see e.g. Antibodies—A laboratory Manual by Ed Harlow and David Lane, Cold Spring Harbor Laboratory 1998, ISBN 0-87969-314-2). The procedure for subsequent generation of humanized antibodies or fragments thereof has also been described (e.g. A. M. Scott et al, Cancer Research 60:3254-3261, 2000; A. Nissim and Y. Chernajovsky, Handb. Exp. Pharmacol. 181:3-18, 2008; A. Mountain and J. R. Adair, Biotechnol. Genet. Eng. Rev. 10:1-142, 1992).

General Expectations of Success in Making Antibodies

It is possible to generate antibodies against any peptide or polypeptide motif of the receptors forming the pain signalling complex which the present invention sets out to inhibit. The antibodies may be generated using short synthetic oligopeptides that encompass the desired target epitope. Therefore, it is guaranteed that antibodies against ligand binding sites on receptors can be generated. Whether or not individual antibody species have the potential to inhibit ligand binding simply depends on the fact that the affinity of the immunoglobulin for the receptor exceeds that of the ligand. In the end, it is a matter of screening the inhibitory potential of a number of individual antibodies to find one with the desired properties.

Screening assays for inhibitory antibodies are common knowledge and typically involve a competitive enzyme linked immunosorbent assay (ELISA). In detail, the recombinant receptor or a fragment encompassing its ligand binding motif are immobilized in replicate wells of microtiter plates. Subsequently, the wells are incubated with a solution containing the ligand. Binding of the ligand to the immobilized receptor is confirmed using an antibody that recognizes the ligand and that is coupled with a color dye reaction. Binding of the ligand to the receptor is tested in the presence of various antibodies to identify those immunoglobulin species that block ligand binding to the receptor and hence prevent color reaction in the respective microtiter plate well.

Successful Clinical Use of Antibodies

A number of therapeutic antibodies are in clinical use. Examples include Genentech's Rituxan, an antibody directed against the CD20 receptor (used in rheumatoid arthritis), Johnson & Johnson's Remicade, an antibody directed against TNF alpha receptor (in Psoriasis), Roche's Avastin, an anti-VEGF antibody used for treatment of colorectal and lung cancer, as well as Herceptin, an antibody against the receptor HRE2 used in breast cancer therapy.

Assessing binding to a receptor is routine work for the person skilled in the biotechnical field. In this regard it has to be mentioned that pro-neurotrophins as well as the Vps10p-domain receptor family were known at the priority date of this invention and binding assays involving for example pro-neurotrophins has been mentioned in the prior art, for example in the article by Lee et al (2001) Science 294:1945-1948.

Accordingly, in one embodiment of the present invention the at least one agent is an antibody is directed against an extracellular part of the Vps10p-domain receptor.

In another embodiment the agent is an antibody directed against an intracellular part of the Vps10p-domain receptor.

In yet another embodiment of the present invention the antibody is directed against the TrpV receptor.

In another embodiment of the present invention the antibody is directed against the TrkA receptor.

In one embodiment of the present invention said antibody is selected from the group consisting of: polyclonal antibodies, monoclonal antibodies, humanised antibodies, single chain antibodies and recombinant antibodies.

In one embodiment the present invention relates to an immunoconjugate comprising the antibody as defined herein above and a conjugate selected from the group consisting of: a cytotoxic agent such as a chemotherapeutic agent, a toxin, or a radioactive isotope; a member of a specific binding pair, such as avidin or streptavidin or an antigen.

Methods of Screening for Agents/antagonists/inhibitors of the Vps10p-domain Receptor:TrpV Receptor Complex The present invention provides specific targets and methods for screening and evaluating candidate agents capable of binding to an entity of the:
Vps10p-domain receptor:TrpV receptor binary complex, and/or Vps10p-domain receptor:TrkA:TrpV receptor ternary complex thus inhibiting formation of said complex, for the preparation of a medicament for the treatment of pain in a mammal.

While the screening of a large number of peptides for a certain physiological activity may be a laborious undertaking, the exact disclosures of the assay herein to be carried out enables the skilled person to reproduce the present invention without undue burden of experimentation and without needing inventive skill.

For this purpose screening libraries of candidate agents are readily available for purchase on the market. Whether a library is a peptide library or a chemical library does not have any impact in the present situation since screening of chemical libraries is also routine work. In fact screening of chemical libraries is a service offered by commercial companies, and it is clear from their presentation material (See e.g. http://www.analyticon.com/) that they do not consider the screening work as such to be inventive.

In one aspect the present invention relates to an in vitro method for screening for the agent as defined herein above, said method comprising the steps of:

i. providing a Vps10p-domain receptor and a TrpV receptor, or
ii. providing a Vps10p-domain receptor and a TrpV receptor and a TrkA receptor, and
iii. providing a library of potential agents, and
iv. providing an assay for measuring the binding of a first entity Vps10p-domain receptor to a second entity TrpV receptor, or
v. providing an assay for measuring the binding of a first entity TrpV receptor to a second entity Vps10p-domain receptor, or
vi. providing an assay for measuring the binding of a first entity TrpV receptor to a second entity (Vps10p-domain receptor:TrkA receptor) binary complex, or
vii. providing an assay for measuring the binding of a first entity (Vps10p-domain receptor:TrkA receptor) binary complex to a second entity TrpV receptor, or
viii. providing an assay for measuring the binding of a first entity Vps10p-domain receptor to a second entity (TrpV:TrkA receptor) binary complex, or
ix. providing an assay for measuring the binding of a first entity (TrpV:TrkA receptor) binary complex to a second entity Vps10p-domain receptor, or
x. providing an assay for measuring the binding of a first entity TrkA receptor to a second entity (TrpV:Vps10-p domain receptor) binary complex, or
xi. providing an assay for measuring the binding of a first entity (TrpV:Vps10p-domain receptor) binary complex to a second entity TrkA receptor, and
xii. adding the library of potential agents to be tested to the assay selected from iv to xi, and
xiii. determining the amount of said first entity to said second entity, and
xiv. comparing the amount determined in step xiv) with an amount measured in the absence of the agent to be tested,
xv. wherein the difference in the two amounts identifies an agent which alters the binding of the first entity to the second entity.

In another aspect the invention relates to a method for determining the degree of inhibition of an agent of the invention, on activity of a Vps10p-domain receptor in a cell culture expressing said receptor, wherein said Vps10p-domain receptor comprises an amino acid sequence having at least 60% sequence identity to SEQ ID NO. 1, SEQ ID NO. 2, SEQ ID NO. 3, SEQ ID NO. 4 or SEQ ID NO. 5, said method comprising the steps of:

a. providing a cell culture expressing a Vps10p-domain receptor, and
b. providing an agonist of the Vps10p-domain receptor, and
c. providing a library of potential agents, and d. providing an assay for determination of binding to, internalisation of and signalling through, a Vps10p-domain receptor, said assay comprising
e. adding the library of potential agents to be tested c) to the cell culture a), in the presence of the agonist b), and
f. determining
   i. the amount of agent bound to the Vps10p-domain receptor, and/or
   ii. the amount of agent internalised by the Vps10p-domain receptor, and/or
   iii. the degree of signalling through the Vps10p-domain receptor, and
g. comparing the amount determined in step f) with an amount measured in the absence of the agents to be tested,
h. wherein the difference in the two amounts identifies an agent
   i. capable of binding to a Vps10p-domain receptor, and/or
   ii. capable of inhibiting signalling through a Vps10p-domain receptor, and/or
   iii. capable of inhibiting internalisation of an agonist of said Vps10p-domain receptor.

In yet another aspect the present invention relates to a method for determining the degree of inhibition of an agent of the present invention as defined herein above, on activity of a TrpV receptor in a cell culture expressing said receptor, wherein said TrpV receptor comprises an amino acid sequence having at least 70% sequence identity to SEQ ID NO. 6, SEQ ID NO. 7, SEQ ID NO. 8 or SEQ ID NO. 9, said method comprising the steps of:
a. providing a cell culture expressing a TrpV receptor, and
b. providing an agonist of the TrpV receptor, and
c. providing a library of potential agents, and
d. providing an assay for determination of binding to a TrpV receptor, said assay comprising
e. adding the library of potential agents to be tested c) to the cell culture a), in the presence of the agonist b), and
f. determining the amount of agent bound to the TrpV receptor and
g. comparing the amount determined in step f) with an amount measured in the absence of the agent to be tested,
h. wherein the difference in the two amounts identifies an agent capable of binding to a TrpV receptor.

In another aspect the present invention relates to a method for determining the degree of inhibition of an agent as defined herein above on activity of a TrkA receptor in a cell culture expressing said receptor, wherein said TrkA receptor comprises an amino acid sequence having at least 70% sequence identity to SEQ ID NO. 10, said method comprising the steps of:
a. providing a cell culture expressing a TrkA receptor, and
b. providing an agonist of the TrkA receptor, and
c. providing a library of potential agents, and
d. providing an assay for determination of binding to a TrkA receptor, said assay comprising
e. adding the library of potential agents to be tested c) to the cell culture a), in the presence of the agonist b), and
f. determining the amount of agent bound to the TrkA receptor and
g. comparing the amount determined in step f) with an amount measured in the absence of the agent to be tested, wherein the difference in the two amounts identifies an agent capable of binding to a TrkA receptor.

In a further aspect the present invention relates to a method for determining the degree of inhibition of an agent as defined herein above on activity of a Vps10p-domain receptor in a cell culture expressing said receptor and with a cell culture lacking expression of said receptor, said method comprising the steps of:
a. providing a cell culture expressing a Vps10p-domain receptor, and
b. providing a cell culture not expressing a Vps10p-domain receptor, and
c. optionally providing a cell culture overexpressing a Vps10p-domain receptor
d. providing an agonist for pain sensation of the Vps10p-domain receptor, and
e. providing a library of potential agents, and
f. providing a first assay comprising a) and a second assay comprising b) and optionally a third assay comprising c), and
g. adding the library of potential agents to be tested to the three assays, and
h. determining
   i. the amount of agent bound to the Vps10p-domain receptor, and/or
   ii. the amount of agent internalised by the Vps10p-domain receptor, and/or
   iii. the degree of signalling through the Vps10p-domain receptor, and
i. comparing the amount of agent determined in step g) using a) with the amount determined in g) using b) and the amount determined in g) using c),
j. wherein the difference in the amounts identifies an agent capable of
   i. binding to a Vps10p-domain receptor, and/or
   ii. inhibiting signalling through a Vps10p-domain receptor, and/or
   iii. inhibiting internalisation of an agonist of said Vps10p-domain receptor.

In yet another aspect the present invention relates to a method for determining the degree of inhibition of an agent as defined herein above on activity of a TrpV receptor in a cell culture expressing said receptor and with a cell culture lacking expression of said receptor, said method comprising the steps of:
a) providing a cell culture expressing a TrpV receptor, and
b) providing a cell culture not expressing a TrpV receptor, and
c) optionally providing a cell culture overexpressing a trpV receptor
d) providing an agonist of the TrpV receptor, and
e) providing a library of potential agents, and
f) providing a first assay comprising a) and a second assay comprising b) and optionally a third assay comprising c), and
g) adding the library of potential agents to be tested to the three assays, and determining
   i. the amount of agent bound to the TrpV receptor, and/or
   ii. the degree of signalling through the TrpV receptor, and
h) comparing the amount of agent determined in step h) using a) with the amount determined in h) using b) and the amount determined in g) using c),
i) wherein the difference in the amounts identifies an agent capable of binding to a TrpV receptor, and/or inhibiting signalling through a TrpV.

In a further aspect the present invention relates to a method for determining the degree of inhibition of an agent as defined herein above on activity of a TrkA receptor in a cell culture expressing said receptor and with a cell culture lacking expression of said receptor, said method comprising the steps of:

a. providing a cell culture expressing a TrkA receptor, and
b. providing a cell culture not expressing a TrkA receptor, and
c. optionally providing a cell culture overexpressing a TrkA receptor
d. providing an agonist of the TrkA receptor, and
e. providing a library of potential agents, and
f. providing a first assay comprising a) and a second assay comprising b) and optionally a third assay comprising c), and
g. adding the library of potential agents to be tested to the three assays, and
h. determining
  i. the amount of agent bound to the TrkA receptor, and/or
  ii. the amount of agent internalised by the TrkA receptor, and/or
  iii. the degree of signalling through the TrkA receptor, and
i. comparing the amount of agent determined in step h) using a) with the amount determined in h) using b) and the amount determined in g) using c),
j. wherein the difference in the amounts identifies an agent capable of binding to a TrkA receptor, and/or inhibiting signalling through a TrkA.

In yet another aspect the present invention relates to a method for determining the degree of inhibition of an agent as defined herein above on activity of a Vps10p-domain receptor in a mammal expressing said receptor with a second mammal lacking expression of said receptor and a third mammal overexpressing said receptor, said method comprising the steps of:
a. providing a mammal expressing a Vps10p-domain receptor, and
b. providing a mammal not expressing a Vps10p-domain receptor, and
c. providing a mammal overexpressing a Vps10p-domain receptor, and
d. providing an agonist for pain sensation of the Vps10p-domain receptor, and
e. providing a library of potential agents, and
f. administering said library of agents to said mammal of a), b) and c) respectively, and
g. determining the degree of pain signalling through the Vps10p-domain receptor, in each of the mammals defined in a), b) and c), using
  i. von Frey test and/or
  ii. Tail immersion assay and/or
  iii. Hot plate test, and
h. comparing the degree of pain signalling in step g) using a) with the degree determined in g) using b) with the degree determined in g) using c),
  wherein the difference in the degree of inhibition identifies an agent capable of binding to a Vps10p-domain receptor, inhibiting signalling through a Vps10p-domain receptor.

In yet another aspect the present invention relates to a method for determining the degree of inhibition of an agent as defined herein above on activity of a TrpV receptor in a mammal expressing said receptor with a second mammal lacking expression of said receptor and a third mammal overexpressing said receptor, said method comprising the steps of:
a. providing a mammal expressing a TrpV receptor, and
b. providing a mammal not expressing a TrpV receptor, and
c. providing a mammal overexpressing a TrpV receptor, and
d. providing an agonist for pain sensation of the TrpV receptor, and
e. providing a library of potential agents, and
f. administering said library of agents to said mammal of a), b) and c) respectively, and
g. determining the degree of pain signalling through the TrpV receptor, in each of the mammals defined in a), b) and c), using von Frey test and/or Tail immersion assay and/or Hot plate test, and
h. comparing the degree of pain signalling in step g) using a) with the degree determined in g) using b) with the degree determined in g) using c),
  wherein the difference in the degree of inhibition identifies an agent capable of binding to a TrpV receptor and inhibiting signalling through said TrpV receptor.

In another aspect the present invention relates to a method for determining the degree of inhibition of an agent as defined herein above, on activity of a Vps10-p domain receptor:TrpV receptor binary complex in a mammal expressing said receptors with a second mammal lacking expression of said receptors and a third mammal overexpressing said receptors, said method comprising the steps of:
a. providing a first and a second mammal expressing both a TrpV receptor and a Vps10p-domain receptor, and
b. providing a first and a second mammal lacking expressing of a TrpV receptor and a Vps10p-domain receptor, and
c. providing a first and a second mammal overexpressing a TrpV receptor and a Vps10p-domain receptor, and
d. providing an agonist for pain sensation of the TrpV receptor and/or Vps10p-domain receptor, and
e. providing a library of potential agents capable of inhibiting signalling through a Vps10p-domain receptor:TrpV receptor binary complex, and
f. administering said library of agents to said first mammal of a), b) and c) respectively, and
g. administering placebo to said second mammal of a), b), and c), and
h. determining the degree of pain signalling through the TrpV receptor, in each of the first and second mammals defined in a), b) and c), using
  i. von Frey test and/or
  ii. Tail immersion assay and/or
  iii. Hot plate test, and
i. comparing the degree of pain signalling in the first and second mammals of step h) using a) and
j. comparing the degree of pain signalling in the first and second mammals of h) using b) and
k. comparing the degree of pain signalling in the first and second mammals of h) using c),
  wherein the difference in the degree of inhibition of pain signalling identifies an agent capable of binding to a Vps10p-domain receptor:TrpV receptor complex and inhibiting signalling through said complex.

In a further embodiment the pain sensation agonist as described in the screening methods herein above, is a TrkA receptor (SEQ ID NO. 10) or a fragment or variant thereof.

In yet another embodiment the pain sensation agonist as described in the screening methods herein above is a neurotrophin selected from the group consisting of NGF, BDNF, NT3 and NT4/5 or a fragment or variant thereof.

SorCS1-2 Knock-out Mouse

In an important aspect the present invention relates to a transgenic knock-out mouse in which the endogenous Vps10p-domain receptor SorCS1 and/or SorCS2 genes have been disrupted to abolish expression of a functional receptor, and wherein said mouse exhibits a reduced response towards pain stimuli relative to a non-transgenic control mouse.

In a further embodiment the gene disruption of the transgenic mouse as defined herein above comprises a deletion of the SorCS1 receptor gene nucleotide sequences encoding the start codon or a region of the mouse SorCS1 receptor from the extracellular domain, transmembrane domain, or the cytoplasmic domain.

In a further embodiment the invention relates to a method for screening a candidate agent for the ability to reduce pain in the transgenic mouse as defined herein above comprising:
a. providing a first and a second transgenic SorCS1 and/or SorCS2 mouse as defined herein above;
b. administering to said first transgenic mouse a candidate agent, and
c. comparing pain behaviour of said first transgenic mouse of step (b) to the pain behaviour of said second transgenic mouse of step (a) not administered said candidate agent; wherein a reduction in pain behaviour in said first transgenic mouse administered said candidate agent relative to said second transgenic mouse not administered said candidate agent indicates that the candidate agent reduces pain behavior.

In one aspect the present invention relates to a method for screening a candidate agent for the ability to reduce pain in the transgenic SorCS1-2 mouse as defined herein above comprising the steps of:
a. providing SorCS1-2 mouse as defined herein above;
b. providing wild type mouse lacking the gene disruption in SorCS1-2 as defined herein above; and
c. providing a control wild type mouse lacking the gene disruption in SorCS1-2 as defined herein above; and
d. administering to said first wild-type mouse (b) a candidate agent, and
e. comparing pain behaviour of said transgenic mouse of step (a) to the pain behaviour of said wild-type mouse of step (b) administered said candidate agent with to the pain behaviour of said control wild-type mouse of step (c) not administered said candidate agent; wherein a reduction in pain behaviour in said wild type mouse (b) administered said candidate agent to a level comparable with said second transgenic mouse not administered said candidate agent relatively to the control wild-type mouse (c) indicates that the candidate agent reduces pain behavior.

Mouse Overexpressing Sortilin or SorCS1 or SorCS2

In another main aspect the present invention relates to a transgenic mouse for conditional or obligate over-expression of Sortilin or SorCS1 or SorCS2 in neuronal tissues.

In one embodiment the transgenic mouse for conditional or obligate over-expression of Sortilin or SorCS1 or SorCS2 in neuronal tissues as defined herein above, relative to a non-transgenic littermate, exhibits protection from pain stimuli as determined by a method selected from the group consisting of Hot plate test, Tail immersion assay and von Frey test.

Pharmaceutical Composition and Administration Forms

The main routes of drug delivery, in the treatment method are intravenous, oral, and topical. Other drug-administration methods, such as subcutaneous injection or via inhalation, which are effective to deliver the drug to a target site or to introduce the drug into the bloodstream, are also contemplated.

The mucosal membrane to which the pharmaceutical preparation of the invention is administered may be any mucosal membrane of the mammal to which the biologically active substance is to be given, e.g. in the nose, vagina, eye, mouth, genital tract, lungs, gastrointestinal tract, or rectum, preferably the mucosa of the nose, mouth or vagina.

Compounds of the invention may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. The compounds may also be administered by inhalation, which is by intranasal and oral inhalation administration. Appropriate dosage forms for such administration, such as an aerosol formulation or a metered dose inhaler, may be prepared by conventional techniques.

The compounds according to the invention may be administered with at least one other compound. The compounds may be administered simultaneously, either as separate formulations or combined in a unit dosage form, or administered sequentially.

Formulations

Whilst it is possible for the compounds or salts of the present invention to be administered as the raw chemical, it is preferred to present them in the form of a pharmaceutical formulation. Accordingly, the present invention further provides a pharmaceutical formulation, for medicinal application, which comprises a compound of the present invention or a pharmaceutically acceptable salt thereof, as herein defined, and a pharmaceutically acceptable carrier therefore.

The compounds of the present invention may be formulated in a wide variety of oral administration dosage forms. The pharmaceutical compositions and dosage forms may comprise the compounds of the invention or its pharmaceutically acceptable salt or a crystal form thereof as the active component. The pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, wetting agents, tablet disintegrating agents, or an encapsulating material.

Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like.

In powders, the carrier is a finely divided solid which is a mixture with the finely divided active component. In tablets, the active component is mixed with the carrier having the necessary binding capacity in suitable proportions and compacted in the shape and size desired. Powders and tablets preferably contain from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

Other forms suitable for oral administration include liquid form preparations including emulsions, syrups, elixirs, aqueous solutions, aqueous suspensions, toothpaste, gel dentrifrice, chewing gum, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavours, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavours, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides; (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-.beta.-aminopropionates, and 2-alkylimidazoline quaternary ammonium salts, and (e) mixtures thereof.

The parenteral formulations typically will contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The compounds of the invention can also be delivered topically. Regions for topical administration include the skin surface and also mucous membrane tissues of the vagina, rectum, nose, mouth, and throat. Compositions for topical administration via the skin and mucous membranes should not give rise to signs of irritation, such as swelling or redness.

The topical composition may include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example. Methods for preparing such compositions are well known in the pharmaceutical industry.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or colouring agents. Formulations suitable for topical administration in the mouth include lozenges comprising active agents in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Transdermal Delivery

The pharmaceutical agent-chemical modifier complexes described herein can be administered transdermally. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the complex to a patient's skin for an extended period of time. Transdermal patches have the added advantage of providing controlled delivery of a pharmaceutical agent-chemical modifier complex to the body. See Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1-3, Kydonieus and Berner (eds.), CRC Press, (1987). Such dosage forms can be made by dissolving, dispersing, or otherwise incorporating the pharmaceutical agent-chemical modifier complex in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Passive Transdermal Drug Delivery

A variety of types of transdermal patches will find use in the methods described herein. For example, a simple adhesive patch can be prepared from a backing material and an acrylate adhesive. The pharmaceutical agent-chemical modifier complex and any enhancer are formulated into the adhesive casting solution and allowed to mix thoroughly. The solution is cast directly onto the backing material and the casting solvent is evaporated in an oven, leaving an adhesive film. The release liner can be attached to complete the system.

Alternatively, a polyurethane matrix patch can be employed to deliver the pharmaceutical agent-chemical modifier complex. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and complex to the prepolymer results in the formation of a tacky firm elastomer that can be directly cast only the backing material.

A further embodiment of this invention will utilize a hydrogel matrix patch. Typically, the hydrogel matrix will comprise alcohol, water, drug, and several hydrophilic polymers. This hydrogel matrix can be incorporated into a transdermal patch between the backing and the adhesive layer.

The liquid reservoir patch will also find use in the methods described herein. This patch comprises an impermeable or semipermeable, heat sealable backing material, a heat sealable membrane, an acrylate based pressure sensitive skin adhesive, and a siliconized release liner. The backing is heat sealed to the membrane to form a reservoir which can then be filled with a solution of the complex, enhancers, gelling agent, and other excipients.

Foam matrix patches are similar in design and components to the liquid reservoir system, except that the gelled pharmaceutical agent-chemical modifier solution is constrained in a thin foam layer, typically a polyurethane. This foam layer is situated between the backing and the membrane which have been heat sealed at the periphery of the patch.

For passive delivery systems, the rate of release is typically controlled by a membrane placed between the reservoir and the skin, by diffusion from a monolithic device, or by the skin itself serving as a rate-controlling barrier in the delivery system. See U.S. Pat. Nos. 4,816,258; 4,927,408; 4,904,475; 4,588,580, 4,788,062; and the like. The rate of drug delivery will be dependent, in part, upon the nature of the membrane. For example, the rate of drug delivery across membranes within the body is generally higher than across dermal barriers. The rate at which the complex is delivered from the device to the membrane is most advantageously controlled by the use of rate-limiting membranes which are placed between the reservoir and the skin. Assuming that the skin is sufficiently permeable to the complex (i.e., absorption through the skin is greater than the rate of passage through the membrane), the membrane will serve to control the dosage rate experienced by the patient.

Suitable permeable membrane materials may be selected based on the desired degree of permeability, the nature of the complex, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Other items may be contained in the device, such as other conventional components of therapeutic products, depending upon the desired device characteristics. For example, the compositions according to this invention may also include one or more preservatives or bacteriostatic agents, e.g., methyl hydroxybenzoate, propyl hydroxybenzoate, chlorocresol, benzalkonium chlorides, and the like. These pharmaceutical compositions also can contain other active ingredients such as antimicrobial agents, particularly antibiotics, anesthetics, analgesics, and antipruritic agents.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The active compound may be formulated into a suppository comprising, for example, about 0.5% to about 50% of a compound of the invention, disposed in a polyethylene glycol (PEG) carrier (e.g., PEG 1000 [96%] and PEG 4000 [4%].

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example with a dropper, pipette or spray. The formulations may be provided in a single or multidose form. In the latter case of a dropper or pipette this may be achieved by the patient administering an appropriate, predetermined volume of the solution or suspension. In the case of a spray this may be achieved for example by means of a metering atomizing spray pump.

The compounds of the present invention may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Pharmaceutically Acceptable Salts

Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

Accordingly, in one aspect the invention relates to a pharmaceutical composition—comprising an agent as defined herein above.

In one embodiment the pharmaceutical composition as defined herein above comprises a pharmaceutically acceptable carrier.

In one embodiment of the present invention the pH of the pharmaceutical composition as defined herein above is between pH 5 and pH 9.

In one embodiment the pharmaceutical composition as defined herein above is formulated for administration by injection, suppository, oral administration, sublingual tablet or spray, cutaneous administration, inhalation or for local administration using an implantable biocompatible capsule.

In a further embodiment the injection is intravenous, intramuscular, intraspinal, intraperitoneal, subcutaneous, a bolus or a continuous administration.

In one embodiment the pharmaceutical composition according to the present invention is administered at intervals of 30 minutes to 24 hours.

In a further embodiment the pharmaceutical composition according to the present invention is administered at intervals of 1 to 6 hours.

In one embodiment, the pharmaceutical composition as defined herein above is administered at intervals of 6 to 24 hours.

In a further embodiment the pharmaceutical composition according to the present invention is administered at intervals of 6 to 72 hours.

In another embodiment, the pharmaceutical as defined herein above is administered at intervals of 1 to 7 days, such as every 2 days, e.g. every 4 days, such as every 6 days.

In one embodiment, the duration of the treatment with the pharmaceutical composition as defined herein above is from 1 to 52 weeks.

In one embodiment, the duration of the treatment with the pharmaceutical composition as defined herein above is from 25 to 104 weeks.

In one embodiment, the duration of the treatment with the pharmaceutical composition as defined herein above is 2 to 7 years.

In one embodiment, the duration of the treatment with the pharmaceutical composition as defined herein above is life long.

In one embodiment the pharmaceutical composition comprising the antagonist/inhibitor to the Vps10p-domain receptor according to the present invention is administered at a dosage of between 10 μg to 500 mg per kg body mass.

In another embodiment, the dosage of the active ingredient of the pharmaceutical composition according to the present invention is between 10 μg to 500 mg per kg body mass, such as 20 μg to 400 mg per kg body mass, e.g. from 50 μg to 200 mg per kg body mass, such as from 70 μg to 100 mg per kg body mass.

Second Active Ingredient

In one embodiment the pharmaceutical composition as defined herein above comprises a second active ingredient.

In a further embodiment said second active ingredient is selected from the group consisting of Antidepressants, Anticonvulsants, Local anaesthetics, Opiods, NMDA anatagonists, Tramadol, Capsazepine, and Capsaicin.

In a further embodiment of the present invention the antidepressants as defined herein above are selected from the group consisting of Tricyclic antidepressants and Amitryptilin.

In a further embodiment of the present invention the Anticonvulsants as defined herein above are selected from the group consisting of Gabapentin, carbamazepin, phenyloin, and lamotrigin.

In a further embodiment of the present invention the local anaesthetics as defined herein above are selected from the group consisting of Lidocaine and mexiletine.

In a further embodiment of the present invention the Opiods as defined herein above are selected from the group consisting of Morphine, fentanyl and oxycodone.

In a further embodiment of the present invention the NMDA antagonists as defined herein above are selected from the group consisting of Ketamine, memantine and amantadine.

In an important aspect the present invention relates to the use of the at least one agent as defined herein above wherein said agent is capable of inhibiting expression of a Vps10p-domain receptor or a TrpV receptor or a TrkA receptor in an animal.

Kit of Parts

In one aspect the present invention relates to a kit in parts comprising:
- a pharmaceutical composition as defined herein above
- a medical instrument or other means for administering the medicament
- instructions on how to use the kit in parts.
- optionally a second active ingredient as defined herein above Method of Treatment In one aspect the present invention relates to a method of treatment of pain in a subject comprising administering to an individual in need thereof a therapeutically effective amount of the pharmaceutical composition herein above.

In one aspect, the present invention relates to a method for treating neuropathy by administering to an individual in need thereof a sufficient amount of the agent as defined herein above.

It is understood that the skilled person would know how to apply the use of the agent of the present invention for the preparation of a medicament for the treatment of pain, as defined herein above, to a method of treating pain in an individual in need thereof.

Business Method

In one aspect, the present invention relates to a method for marketing of a medicinal product, said product comprising at least one isolated agent, said agent being capable of inhibiting formation of the:
a. Vps10p-domain receptor:TrpV receptor binary complex, and/or
b. Vps10p-domain receptor:TrkA:TrpV receptor ternary complex, thus being useful in a method of treatment of pain in a subject, said marketing comprising the public spreading of the information that inhibition of formation of said complex has an impact on pain sensation in said subject.

DETAILED DESCRIPTION OF THE DRAWINGS

FIG. 1: The Vps10p-domain receptor family. Their structural organization is indicated.

Figure 2:
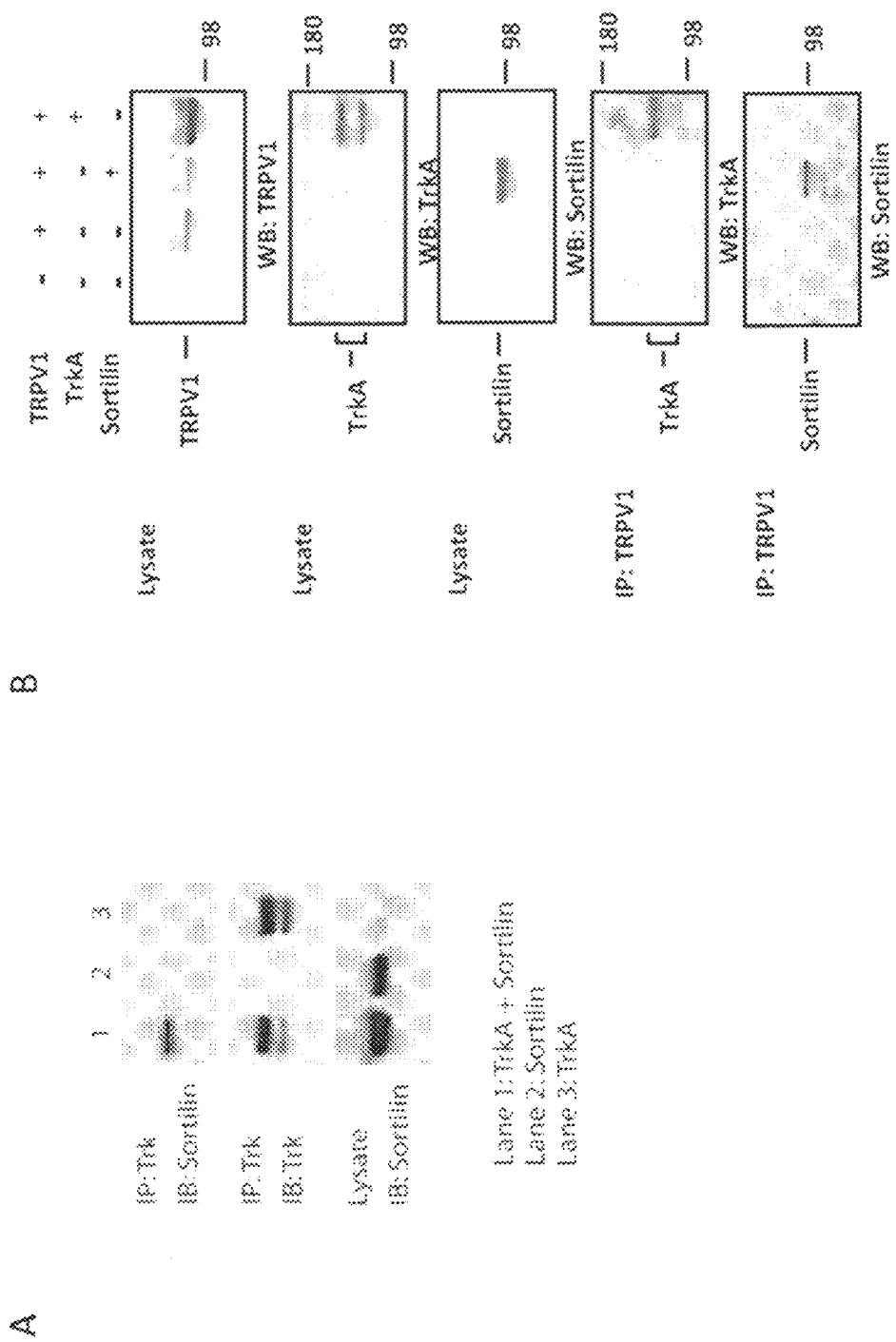

FIG. 2: coIP experiments demonstrating physical interaction between sortilin, TrkA and TrpV1 in HEK293 cells double transfected with the indicated receptors. (A) sortilin and TrkA. (B) TrpV1 and TrkA or sortilin, respectively.

FIG. 3: Schematic representation of di- and trimeric complexes between Sortilin, TrkA and TrpV1 on the plasma membrane. (A) Sortilin and TrpV1. (B) TrkA and TrpV1. (C) Sortilin, TrkA and TrpV1, indicated with TrkA as middle component. (D) Sortilin, TrkA and TrpV1 indicated with TrpV1 as middle component FIG. 4: Stereological and immunofluorescence data demonstrating the expression of sortilin, TrkA and TrpV1 in sensory neuron cell bodies in the dorsal root ganglia (DRG). (A) Count of % positive neuronal profiles of each receptor in DRG. (B) Immunohistology of DRG demonstrating sortilin, TrkA and TrpV1 in small and medium sensory neurons in the DRG.

Figure 5:
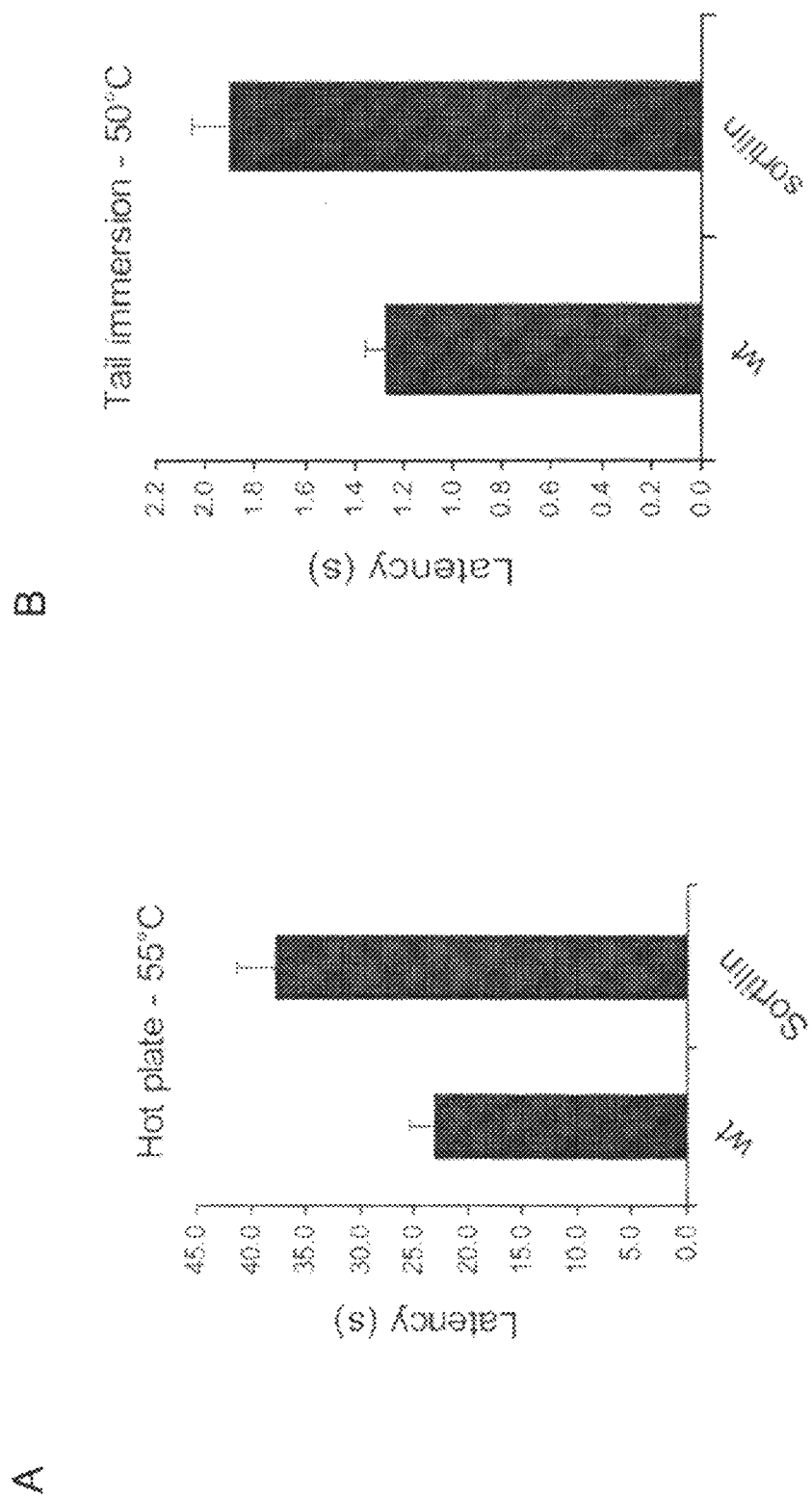

FIG. 5: (A) Hotplate assay and (B) tail flick assay performed on sortilin (+/+) and sortilin (−/−) mice. Lack of sortilin receptor clearly results in increased latency towards painful thermal stimulus, similarly so phenotype observed in TrpV1 (−/−) mice. (C) No change in response to mechanical stimulus (von Frey) is observed from loss of sortilin, in correspondence to observation from TrpV1 (−/−), illustrating that TrpV1 is only involved in thermal/chemical and not mechanical stimulus signaling and loss of sortilin has the same selective phenotype.

Figure 6:
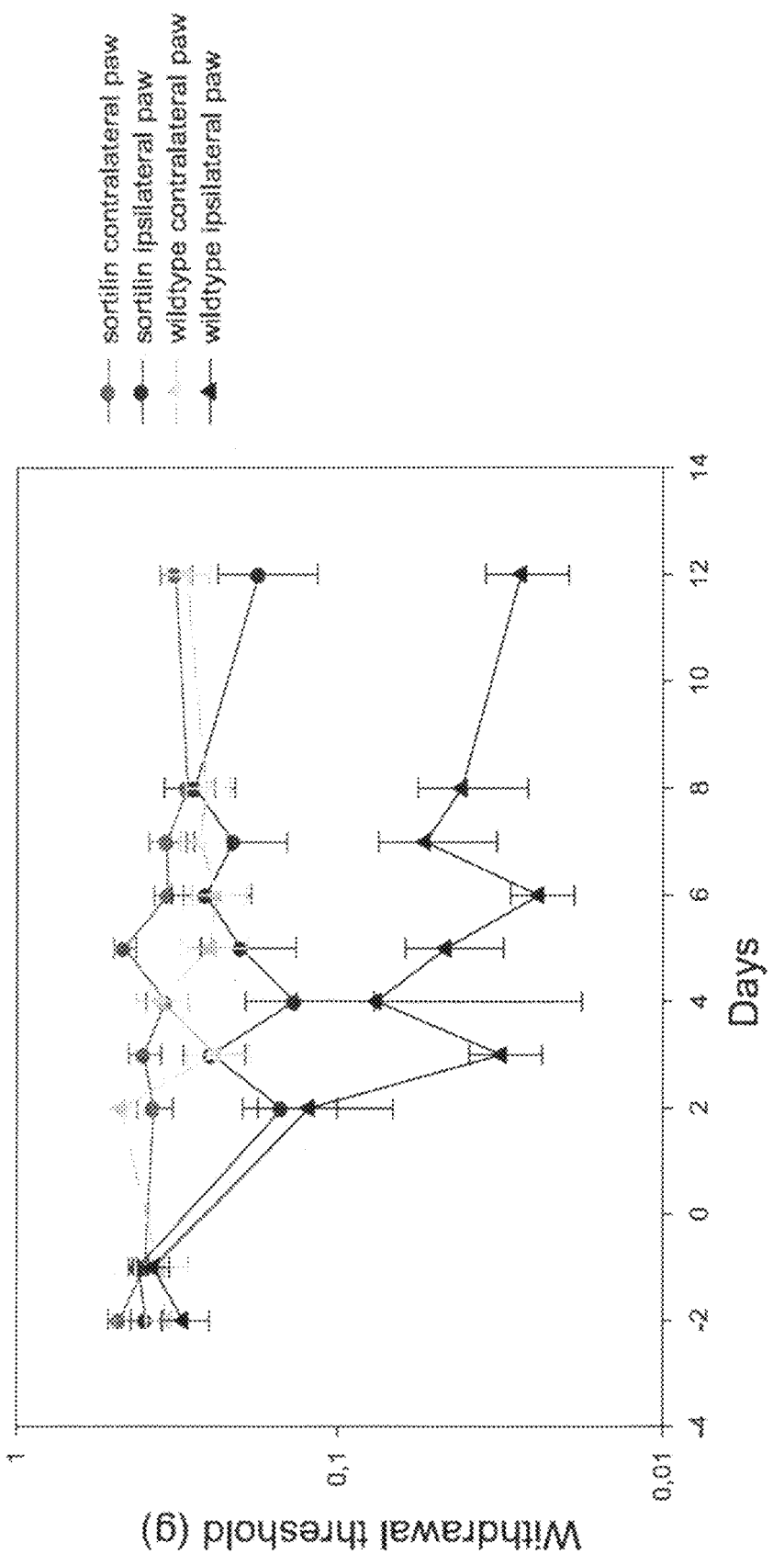

FIG. 6: Development of mechanical allodynia in sciatic nerve injury (SNI) operated wt (n=10) and sortilin (−/−) (=13) mice. The withdrawal threshold on the plantar surface of the hindlimb was measured with von Frey filaments for both the ipsilateral and contralateral paw (data as mean+/−SEM). From day 6 after surgery a significant difference between wt ipsilateral and wt contralateral (p<0.001) was observed whereas the sortilin (−/−) was unable to develop mechanical allodynia.

FIG. 7: (A) Development of mechanical allodynia in Spinal Nerve Ligation (SNL) operated wt (n=9) and sortilin(−/−) (n=11) mice. The withdrawal threshold on the plantar surface of the hindlimb was measured with von Frey filaments for both the ipsilateral and contralateral paw. From the day after surgery a significant difference between wt ipsilateral and wt contralateral was observed whereas the sortilin (−/−) was unable to develop mechanical allodynia.

(B) Development of thermal hyperalgesia in the mice described in (A). The withdrawal threshold of the hindlimb was measured by stimulation with a radiant heat source (Stoelting Plantar Test, Hargreaves Method) for both the ipsilateral and contralateral paw. From the day after surgery a significant difference between wt ipsilateral and wt contralateral was observed whereas the sortilin (−/−) was unable to develop thermal hyperalgesia.

FIG. 8: Competition of peptide based agents of the invention with GST C-terminally tagged with the three C-terminal aminiacids of neurotensin Tyr-11e-Leu (YIL). Binding to immobilized sSortilin was measured by surface plasmon resonance. 100% corresponds to the measured response units obtained for 100 nM GST-YIL in the absence of competing peptide. The EC50 values correspond to the concentration of peptide at which the GST-YIL binding is reduced to 50%.

Sequences are given for the peptides, and for peptides that contain non-natural amino acids the structure is also shown.
Overview of Sequences
SEQ ID NO 1: Sortilin
SEQ ID NO 2: SorLA
SEQ ID NO 3: SorCS1
SEQ ID NO 4: SorCS2
SEQ ID NO 5: SorCS3
SEQ ID NO 6:TrpV1
SEQ ID NO 7:TrpV2
SEQ ID NO 8:TrpV3
SEQ ID NO 9:TrpV4
SEQ ID NO 10:TrkA

EXAMPLES

Example 1

Determining Whether Sortilin, TrkA and TrpV1 are Able to Physically Interact

HEK293 cells stably transfected with combinations of sortilin, TrkA and TrpV1 were crosslinked with DSP (Pierce) and cell lysates were subjected to immunoprecipitation using anti-TrkA or anti-TrpV1 (Santa Cruz Biotechnology) and Sepharose GammabindG beads (G&E Biosciences). IP eluate and lysates were subjected to SDS-PAGE and western blotting. Sortilin-TrkA (FIG. 2A), TrpV1-sortilin and TrpV1-TrkA (FIG. 2B) complexes were demonstrated, suggesting that these receptors are capable of forming dimeric and trimeric complexes with each other.

Example 2

Determining Whether Inactivation of Sortilin Affects Expression of TrkA and TrpV1

Adult mice were decapitated, the lumbar DRG dissected, fixed and cryosectioned at 15 μm. Expression of Sortilin, TrkA and TrpV1 were performed by incubation with primary antibody (anti-sortilin from Alomone Labs, anti-TrkA fra Reichardt lab at UCSF and anti-TrpV1 from Neuromics Lab) followed by fluorescently labeled secondary antibody from Molecular Probes. Samples were coverslipped and images acquired on a Zeiss LSM510 confocal microscope. FIG. 4b illustrates expression of sortilin, TrkA and TrpV1 in L4 DRG neurons and it can be seen that these molecules are all expressed in small and medium size (=nociceptive) neurons. No difference in number of neurons positive for TrkA and TrpV1 was observed between wild-type and Sortilin (−/−) mice, which both demonstrated an expression profile as demonstrated in FIG. 4a (except for sortilin which is absent in sortilin (−/−) mice (data not shown)).

Example 3

Determining Thermal and Mechanical Sensitivity in Response to Sortilin Inactivation Hot plate test: Adult mice (10-20 weeks old) were placed in clear acrylic cages on the hot plate (Buch&Holm, Denmark) set at 55° C. The latency to respond with hind paw lick was measured and the mouse immediately removed (Bannon & Malmberg (2007) Curr. Protoc. Neurosci. 41, 8.9.1-8.9.16). Each animal was tested only once on the same day.

Tail immersion assay: Female mice were briefly (½-1 min) immobilized in a tube restrainer during the procedure. The distal third of the tail was immersed in 50° C. water and the latency to flick the tail was measured. Each animal was tested only once on the same day.

Von Frey test: the mechanical withdrawal threshold on the plantar surface of the hind limbs was measured using calibrated von Frey hairs 0.008 g-1.4 g (Touch-Test® Sensory Evaluators, North Coast Medical, CA). Von Frey hairs of increasing bending force were each applied 5 times to both sides of the plantar hind limb area from below through the mesh floor, and the number of withdrawals counted As shown in FIGS. 5a and 5b, the sortilin (−/−) mice exhibited a significantly decreased response towards thermal stimulus to either the tail or hind leg whereas the response towards mechanical stimulation was unaltered. This shift in sensory phenotype is parallel to that observed in TrpV1 (−/−) mice, strongly suggesting that inactivation of sortilin results in a phenotype similar to that of TrpV1 (−/−) and hence that sortilin is involved in the functional regulation of TrpV1 (Caterina et al. (2000) Science 288, 306-313).

Example 4

Determination of Development of Mechanical Allodynia Following Sciatic Nerve Injury Adult mice were anaesthetized and subjected to unilateral spared nerve injury (SNI) lesion performed by ligation of the sciatic nerve. The following 14 days the animals were tested for the development of mechanical allodynia by measuring the withdrawal threshold on the plantar surface of the hindlimb measured with von Frey filaments (as described in example 3) for both the ipsilateral and contralateral paw. As illustrated in FIG. 6, a significant difference between wt ipsilateral and wt contralateral (p<0.001) was apparent after day 6 whereas the sortilin (−/−) mice were protected against mechanical allodynia.

Example 5a

Demonstration of a Sortilin:TrkA:TrpV1 Receptor Complex

Cells expressing sortilin, TrkA and TrpV1, e.g. following transfection with plasmids encoding all three receptors, respectively, are crosslinked with DSP (Pierce) and subsequently lysed. The cell lysate is incubated with antibody against sortilin covalently bound to sepharose beads. Precipitated complexes are eluted (eluate 1) from the washed beads (acidic buffer and subsequent neutralization) and subjected to another round of immunoprecipitation using anti-TrkA antibody and precipitated proteins eluted (eluate 2) with SDS loading buffer. Eluate 1 is composed of precipitated sortilin alone and/or sortilin-trkA, sortilin-TrpV1 and sortilin-TrkA-TrpV1 complexes whereas eluate 2 only contains sortilin-TrkA and/or sortilin-TrkA-TrpV1 complexes. Western blot analysis of TrpV1 in eluate 2 reveals the formation of a ternary receptor complex between Sortilin, TrkA and TrpV1.

Example 5b

A Cell Based Screening Method for Identifying Agents Disrupting the Formation of Complexes Between Sortilin and TrpV1, and/or Sortilin, TrkA and/or TrpV1, Respectively Determination of binding, internalization or signaling by members of the Vps10p-domain receptor family can be performed in cellular systems. Cells expressing sortilin, TrkA and TrpV1 following e.g. transfection with plasmids encoding all three receptors, respectively, are incubated with a candidate agent (inhibitor/antagonist) compound. Said agent can e.g. represent an antibody against either one of the receptors, Sortilin and TrkA binding ligands such as proNGF, NGF or, fragments of the respective receptors. After incubation, the cells are washed, protein complexes crosslinked with DSP (Pierce) and subsequently lysed. The cell lysate is incubated with antibody against sortilin covalently bound to sepharose beads. Precipitated complexes are eluted (eluate 1) from the washed beads (acidic buffer and subsequent neutralization) and subjected to another round of immunoprecipitation using anti-TrkA antibody and precipitated proteins eluted (eluate 2) with SDS loading buffer. Eluate 1 is composed of precipitated sortilin alone and/or sortilin-TrkA, sortilin-TrpV1 and sortilin-TrkA-TrpV1 complexes whereas eluate 2 only contains sortilin-TrkA and/or sortilin-TrkA-TrpV1 complexes. Western blot analysis of TrkA and TrpV1 in eluate 1 reveals whether candidate compounds are able to inhibit sortilin-TrkA and sortilin-TrpV1 complex formation, respectively. Western blot analysis of TrpV1 in eluate 2 reveals whether candidate compounds are able to inhibit formation of the ternary sortilin-TrkA-TrpV1 complex.

Example 5c

A Cell Based Screening Method for Identifying Receptor Antagonists that Disrupt Signalling by Complexes Comprising Sortilin and TrpV1, and Sortilin, TrkA and/or TrpV1, Respectively Cells expressing sortilin and TrpV1 with or without TrkA, e.g. following transfection with plasmids encoding the relevant receptors are incubated in the absence or presence of candidate antagonists. The cells are subsequently monitored for changes in TrpV1-mediated calcium-influx using AM-Fura2. In brief, cells stably transfected with TrpV1, TrkA and Sortilin are plated in a clear bottom 96 well tissue culture plate (Sigma) and incubated in Dulbecco's Eagle's medium with 1 μM AM-Fura2 (Molecular Probes) at 37° C. in the dark for 30 min. Before $[Ca^{2+}]_i$ measurements, cells are washed three times and incubated for 30 min at room temperature (25° C.) in HEPES-buffered physiological saline solution (HPSS: NaCl, 120 mM; KCl, 5.4 mM; $Mg_2SO_4$, 0.8 mM; HEPES, 20 mM; $CaCl_2$, 1.8 mM; and glucose, 10 mM; with pH 7.4). The cells are stimulated with the TrpV1 agonist capsaicin and/or TrkA agonist NGF and/or other candidate compounds, and fluorescence immediately monitored in a Victor Multilabel plate reader (Perkin Elmer) by excitation alternatively by 340 and 380 nm wavelength and measuring emission fluorescence intensity at 510 nm. All experiments are conducted at room temperature (25° C.) and carried out within 2 h of loading for each coverslip. The data are expressed as the ratio of Fura2 fluorescence due to excitation at 340 nm to that due to excitation at 380 nm ($F_{340}/F_{380}$). The efficacy of candidate antagonists on NGF or capsaicin stimulated calcium-influx can be determined by comparing AM-Fura2 activity in the absence or presence of the antagonist to be tested.

Example 5d

An In Vivo Based Screening Method for Identifying Agents Disrupting the Formation of Complexes Between Sortilin and TrpV1, and/or Sortilin, TrkA and/or TrpV1, Respectively Mice are administered a potential agent (inhibitor or antagonist) e.g. subcutaneously in the absence of presence of a potential agent and pain is evaluated using the hot plate test, tail immersion test, Von Frey test, or the spared nerve injury model as described in examples 3 and 4, respectively. The assay can also be conducted following subcutaneous administration of NGF to the paw to induce TrkA-dependent pain. If an antagonist proves effective it should be able to hamper the pain response elicited in the mouse. Similar studies can be carried out in transgenic mice that overexpress sortilin. Such animals are particularly useful as they exhibit increased sensitivity towards the above described noxious stimuli.

Example 6

An In Vitro Assay for Identifying Agents Disrupting the Formation of Complexes Between, Sortilin and TrpV1, and Sortilin, TrkA and/or TrpV1, Respectively Determination of direct binding of a ligand such as a small organic molecule, a peptide or a soluble receptor including but not limited to Sortilin, TrpV and TrkA, to immobilized protein can be performed by e.g. surface plasmon resonance analysis (Biacore, Sweden) using CaHBS as standard running buffer (10 mM HEPES, pH 7.4, 140 mM NaCl, 2 mM CaCl2, 1 mM EGTA, and 0.005% Tween-20). A biosensor chip from Biacore (CM5, cat. no. BR-1000-14) is activated using the NHS/EDC method as described by supplier followed by coating with a receptor belonging to the Vps10p-domain receptor family. Several different approaches can be applied: Candidate agents can be identified by comparing the binding signal (response units) to a chip immobilized with one of the receptors and comparing this signal to an empty flow cell. In another approach, inhibition of an established ligand can be monitored in the absence or presence of putative inhibitors. The difference in the signal depicts the inhibitory potential of the antagonist. The data collected are analysed by fitting of sensorgrams for affinity estimations and inhibitory potential using the Biaevaluation version 3.1 program. The surface Plasmon resonance assay can easily be transform into other assays in which the Vps10p-domain receptor, the ligand or the putative inhibitor is immobilized on a solid phase. For instance, receptors can be immobilized in e.g. Maxisorp microtiter wells from Nunc (cat. no. 439454) by incubation for 16 h at 4° C. in 50 mM $NaHCO_3$, pH 9.6. After blocking using 5% bovine serum albumin (Sigma, cat. no. A9647) for 2 h at room temperature, the wells are washed three times with MB buffer (10 mM HEPES, pH 7.4, 140 mM NaCl, 2 mM $CaCl_2$, and 1 mM $MgCl_2$) before incubation with a labelled ligand (e.g. iodinated) in the absence or presence of a various concentrations of a candidate inhibitor. Following incubation (e.g. overnight at 4° C.) and washing with MB buffer, bound radioactivity is released by adding 10% SDS. Nonspecific binding of tracer to wells coated only with bovine serum albumin is determined and subtracted from the values determined in the binding experiments. The binding data point can be fitted to binding equations using the Prism software from GraphPad, version 4. Likewise, the antagonist can be labelled and binding to the immobilized receptor directly measured. In yet another setup, the receptor, ligand or antagonist can be immobilized on scintillation beads and binding measured in a scintillation proximity assay in which the receptor-binding molecule has been labelled using radioactivity.

Example 7

A Cell Based Screening Method for Identifying Agents Capable of Inhibiting a Vps10p-Domain Receptor An antagonist directed against an entity of the Vps10p-domain:TrpV:TrkA receptor complex may act as an inhibitor of the entire complex. Accordingly it is relevant to screen for agents capable of binding to e.g. the Vps10p-domain receptor entity. Such a method is described in the present example. Determination of binding, internalization or signalling by members of the Vps10p-domain receptor family can be performed in cellular systems. Cells expressing one of the receptors, either endogenously or following e.g. transfection with a plasmid containing the cDNA of the receptor, are incubated with a radio-labeled ligand, in the absence and the presence respectively, of a candidate inhibitor/antagonist compound. After incubation, the cells are washed to remove unspecific binding and subsequently harvested. The degree of binding of the candidate antagonist/inhibitor to the receptor is determined by using a conventional radioligand assay well known to those skilled in the art. See e.g. Bylund and Toews (1993) Am J. Physiol. 265(5 Pt 1):L421-9 entitled "Radioligand binding methods: practical guide and tips". Likewise, endocytosis/internalization may be determined as described in Nykjr et al (1992) FEBS Letters 300:13-17, and in Nielsen et al (2001) EMBO J., 20:2180-.

Example 8

Methods of Treatment

The resulting developed active agent of peptide nature (possible antibody based) either freeze-dried to be dissolved before use or as a ready to use solution so that it can be given for parenteral administration route (e.g. intravenously (I.V.), intramuscularly (I.M.) or subcutaneously (S.C.). Mucosal application of a solid dose form also represents a possibility in this case.

If the resulting developed active agent is of chemical nature a formulation for oral administration as well as a potential route is prepared e.g. for S.C. or I.M. use.

The developed medicament will either be used for prophylactic purpose or given chronically for long life treatment. In the first case the active agent interferes with, and thereby prevents, the process of molecular events to take place that leads to the chronic lowering of the pain threshold. The developed medicament is also intended to be given before a planned operation or as fast as possible after an injury involving nervous tissue.

In case at that time a genetic test is developed to diagnose individuals predisposed to develop neuropathic pain the medicament should be used were possible in connection with such a diagnostics e.g. as a theranostic treatment.

Have a chronic pain condition such as neuropathic pain developed, i.e. the threshold level activation has taken place, chronic treatment with the medicament represents another possibility. The rationale is constantly to be able to suppress the molecular events keeping the nociceptive pain threshold low.

Finally it will be possible to co-administer the medicament together with conventional treatments for neuropathic pain e.g. with opioids, non-steroidal anti-inflammatory drugs, anti-convulsants, tricyclic anti-depressants and $Na^+$ channel blockers.

Example 8A

Prophylactic Treatment in Case of Accidental Nerve Injury

A 52-year-old woman is brought into hospitals 30 minutes after a traffic crash where the arm and shoulder have been injured and exhibiting severe pain. The objective examination reveals that several muscles of the injured arm are paralysed.

To prevent development of neuropathic pain a subcutaneous injection of the agent of the present invention (e.g. an antibody) of e.g. 1 mg/kg body weight.

To reduce the pain the patient is treated with opioids and NSAIDs. Over the following days the pain pattern is followed and if the pain intensity is not lowered within 5 days the treatment with the agent of the present invention is repeated.

Example 8B

Planned Thoracotectomy for Heart Operation

A 60-year-old man has to go through open heart surgery. He has history of chronic pain with mechanic allodynia since an open leg fracture 20 years ago.

The patient is prone to develop neuropathic pain after the throracotectomy for which reason the patient 12 hours before the operation receives the agent of the present invention (e.g. an antibody) in a dose of e.g. 1 mg/kg body weight as a subcutaneous injection. The treatment is repeated when the patient is stabilized after the operation e.g. 24 hours later.

Over the following days the pain pattern is followed and if the pain intensity is not lowered within 5 days the treatment with the agent of the present invention is repeated.

Example 8C

Treatment of a Patient with Neuropathic Pain Symptoms

A 44-year-old woman with a history of hyperalgesia and mechanical allodynia developed after a traffic accident where the shoulder was injured with subsequent paralysis of *m. subscapularis* and *m. supraspinatus* seek help for further pain relief The patient is in treatment with 2800 mg gabapentin daily. The treatment dampens the pain intensity, but still the pain invalidates the daily life. The pain intensity becomes unbearable upon use of the arm which then demands opioids to dampen.

Further to the gabapentin treatment the patient is treated with the agent of the present invention (e.g. a small organic molecule or synthetic neurotensin analogue) e.g. 100 ug/kg body weight once a day. Good effect is obtained and the patient is set on lifelong treatment.

Example 9

Determination of Development of Mechanical Allodynia and Thermal Hyperalgesia Following Spinal Nerve Ligation Adult mice were anaesthetized and subjected to unilateral spinal nerve lesion (SNL) performed by cutting of the L5 spinal nerve distal to the DRG. The following 12 days the animals were tested for the development of mechanical allodynia by measuring the withdrawal threshold on the plantar surface of the hindlimb measured with von Frey filaments (as described in example 3 and 4) for both the ipsilateral and contralateral paw. Furthermore, the animals were tested during the same time period and both on the ipsilateral and contralateral paws for the development of thermal hyperalgesia by exposing the hind feet to a radient heat source (Stoelting Plantar Test, Hargreaves method) and measuring the paw withdrawal latency.

As illustrated in FIG. 7a (mechanical allodynia) and 7b (thermal hyperalgesia), a significant difference between wt ipsilateral and wt contralateral was apparent after only 1 day postsurgery whereas the sortilin (−/−) mice were protected against mechanical allodynia (FIG. 7a) and thermal hyperalgesia (FIG. 7b).

REFERENCES

[1] Dworkin, R. H. "An overview of neuropathic pain: syndromes, symptoms, signs, and several mechanisms", *Clin. J. Pain* 18:343-349 (2002)
[2] Green, B. G. "Temperature perception and nociception", *J. Neurobial* 61:13-29. (2004.)
[3] Tegeder, I., Costigan, M., Griffin, R. S., Abele, A., Belfer, I., Schmidt, H., Ehnert, C., Nejim, J., Marian, C., Scholz, J., Wu, T., Allchorne, A., Diatchenko, L., Binshtok, A. M., Goldman, D., Adolph, J., Sama, S., Atlas, S. J., Carlezon, W. A., Parsegian, A., Lötsch, J., Fillingim, R. B., Maixner, W., Geisslinger, G., Max, M. B., Woolf, C. J. "GTP cyklohydrolase and tetrahydrobiopterin regulate pain sensitivity and persistence", *Nature Medicine* 1:1269-77 (2006).
[4] Bisgaard, T., Rosenberg, J and Kejlet, H. "From acute to clinic pain after Laparoscopic cholecystectomy: a prospective fellow-up analysis". *Scand. J. Gastroenreol.* 40:1358-1364 (2005)
[5] Devor, M. & Seltzer, Z. Textbook of pain. Wall, P. D. & Melzack, R. (eds.). Elsevier Science (1999).
[6] Raja, S. N., Meyer, R. A., Ringkamp, M., & Campbell, J. N. Textbook of pain. Wall, P. D. & Melzack, R. (eds.). *Elsevier Science* (1999).
[7] Jensen, T. S. & Baron, R. "Translation of symptoms and signs into mechanisms in neuropathic pain", *Pain* 102:1-8 (2003).
[8] Zimmermann, M. "Pathobiology of neuropathic pain", *Eur. J. Pharmacol.* 429:23-37 (2001)
[9] Dickensen, A. H., Matthews, E. A. & Suziki, R. Neurobiology of neuropathic pain: mode of action of anticonvulsants. *European Journal of Pain-London* 6.
[10] Lai, J., Porreca, F., Hunter, J. C. & Gold, M. S. "Voltage-gated sodium channels and hyperalgesia", *Annu. Rev. Pharmacol. Toxicol.* 44:371-397 (2004)
[11] McCleane, G. "Pharmacological management of neuropathic pain", CNS. Drugs 17:1031-1043 (2003)
[12] Mattia, C. & Coluzzi, F. "Antidepressants in chronic neuropathic pain", *Mini. Rev. Med. Chem.* 3:773-784 (2003)
[13] Tamayo, N., Liao, H., Stec, M. M., Wang, X., Chakrabarti, P., Retz, D., Doherty, E. M., Surapaneni, S., Tamir, R., Bannon, A. W., Gavva, N. R., Norman, M. H. "Design and synthesis of peripherally restricted transient receptor potential vanilloid 1 (TRPV1) antagonists", *J. Med. Chem.* 2008, 51:2744-57).
[14] Scholz, J. and Woolf, C. J. "Can we conquer pain?" Nat *Neurosci* 5 *Suppl.* 1062-7
[15] Hald, A., Nedergaard, S., Hansen, R. R., Ding, M., Heegaard, A.-M. "Differential activation of spinal cord glial cells in murine models of neuropathic and cancer pain", *Eur. J. Pain* in press (2008)
[16] Smeyne, R. J., Klein, R., Schnapp, A., Long, L. K., Bryant, S., Lewin, A., Lira, S. A. Barbacid, M. "Severe sensory and sympathetic neuropathies in mice carrying a disrupted Trk/NGF receptor gene", Nature 368:246-9 (1994).
[17] Arnett, M. G., Ryals, J. M., Wright, D. E. "pro-NGF, sortilin, and p75$^{NTR}$: Potential mediators of injury-induced apoptosis in the mouse dorsal root ganglion". *Brain Research* 1183:32-42 (2007).
[18] Petersen et al., J. Biol. Chem., 272:3599-3605 (1997)
[19] Herman-Borgmeyer et al., Mol. Brain. Res., 65:216-219 (1999)
[20] Jacobsen et al., J. Biol. Chem., 271:31379-31383 (1996)
[21] Marcusson, E. G., et al., Cell, 77:579-586 (1994)
[22] J. Mazella et al., J Biol Chem 273, 26273 (1998).
[23] C. Munck Petersen et al., Embo J 18, 595 (1999).
[24] A. Nykjaer et al., Nature 427, 843 (2004).
[25] H. K. Teng et al., J Neurosci 25, 5455 (2005).
[26] U. B. Westergaard et al., J Biol Chem 279, 50221 (2004).
[27] S. Maeda et al., J Cell Physiol 193, 73 (2002).
[28] M. S, Nielsen, C. Jacobsen, G. Olivecrona, J. Gliemann, C. M. Petersen, Biol Chem 274, 8832 (1999).
[29] M. S, Nielsen et al., Embo J 20, 2180 (2001).
[30] K. Nakamura, K. Namekata, C. Harada, T. Harada, Cell Death Differ 14, 1552 (2007).
[31] P. Jansen et al., Nat Neurosci 10, 1449 (2007).
[32] P. Chalon et al., FEBS Lett 386, 91 (1996).
[33] L. Jacobsen et al., J Biol Chem 276, 22788 (2001).
[34] K. Tanaka, M. Masu, S, Nakanishi, Neuron 4, 847 (1990).
[35] J. P. Vincent, J. Mazella, P. Kitabgi, Trends Pharmacol Sci 20, 302 (1999).
[36] Willer et al. (2008) Nature Genetics 40(2): 161-169
[37] Kathiresan et al. (2008) Nature Genetics 40(2): 189-97
[38] U. B. Westergaard, K. Kirkegaard, E. S. Sørensen, C. Jacobsen, M. S, Nielsen, C. M. Petersen, P. Madsen, (2005) FEBS Letters 579:1172-1176
[39] Chao, M. V. "Neurotrophins and their receptors: a convergence point for many signalling pathways", Nat Rev Neurosci. 4:299-309 (2003)
[40] Huang, E. J., Reichardt, L. F. "Trk receptors: roles in neuronal signal transduction", Annu Rev Biochem. 72:609-42 (2003)
[41] Huang, E. J., Reichardt, L. F. "Neurotrophins: roles in neuronal development and function", Annu Rev Neurosci. 24:677-736 (2001)
[42] Chuang, H. H., Prescott, E. D., Kong, H., Shields, S., Jordt, S. E., Basbaum, A. I., Chao, M. V., Julius, D. "Bradykinin and nerve growth factor release the capsaicin receptor from PtdIns(4,5)P2-mediated inhibition", Nature 411: 957-62 (2001).
[43] Dhaka, A., Viswanath, V., Patapoutian, A. "Trp ion channels and temperature sensation", Annu Rev Neurosci. 29:135-61 (2006)
[44] Patapoutian, A., Peier, A. M., Story, G. M., Viswanath, V. "ThermoTRP channels and beyond: mechanisms of temperature sensation" *Nature Reviews Neuroscience* 4:529-539 (2003)

The invention claimed is:

1. A method of treating pain comprising administering to a mammal in need thereof an antibody or fragment thereof which binds the extracellular domain of Sortilin and inhibits formation of the:
    a. Sortilin receptor:TrpV receptor binary complex, and/or
    b. Sortilin receptor:TrkA:TrpV receptor ternary complex.

2. The method of claim 1, wherein the pain is chronic pain.

3. The method of claim 1, wherein the pain is neuropathic pain.

4. The method of claim 1, wherein the antibody is selected from the group consisting of humanised antibodies, single chain antibodies, and recombinant antibodies.

5. The method of claim 1, wherein the antibody fragment is a Fab fragment.

* * * * *

UNITED STATES PATENT AND TRADEMARK OFFICE
CERTIFICATE OF CORRECTION

| | | |
|---|---|---|
| PATENT NO. | : 8,460,657 B2 | Page 1 of 1 |
| APPLICATION NO. | : 13/000854 | |
| DATED | : June 11, 2013 | |
| INVENTOR(S) | : Nykjaer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 218 days.

Signed and Sealed this
Twenty-third Day of December, 2014

Michelle K. Lee
*Deputy Director of the United States Patent and Trademark Office*

SEQUENCE LISTING

<160> NUMBER OF SEQ ID NOS: 10

<210> SEQ ID NO 1
<211> LENGTH: 831
<212> TYPE: PRT
<213> ORGANISM: Homo sapiens
<220> FEATURE:
<221> NAME/KEY: SIGNAL
<222> LOCATION: (1)..(33)
<223> OTHER INFORMATION: Sortilin signal peptide
<220> FEATURE:
<221> NAME/KEY: PROPEP
<222> LOCATION: (34)..(77)
<223> OTHER INFORMATION: Sortilin propeptide
<220> FEATURE:
<221> NAME/KEY: MISC_FEATURE
<222> LOCATION: (78)..(755)
<223> OTHER INFORMATION: Extracellular part of Sortilin (sSortilin)
<220> FEATURE:
<221> NAME/KEY: TRANSMEM
<222> LOCATION: (756)..(778)
<223> OTHER INFORMATION: Membrane spanning part of Sortilin
<220> FEATURE:
<221> NAME/KEY: MISC_FEATURE
<222> LOCATION: (779)..(831)
<223> OTHER INFORMATION: Intracellular (cytoplasmic) domain of Sortilin

<400> SEQUENCE: 1

```
Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255
```

-continued

Cys Leu Ala Lys Trp Gly Ser Asp Asn Thr Ile Phe Phe Thr Thr Tyr
         260                 265                 270

Ala Asn Gly Ser Cys Lys Ala Asp Leu Gly Ala Leu Glu Leu Trp Arg
         275                 280                 285

Thr Ser Asp Leu Gly Lys Ser Phe Lys Thr Ile Gly Val Lys Ile Tyr
290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Phe Tyr Ser
             340                 345                 350

Ile Leu Ala Ala Asn Asp Asp Met Val Phe Met His Val Asp Glu Pro
             355                 360                 365

Gly Asp Thr Gly Phe Gly Thr Ile Phe Thr Ser Asp Asp Arg Gly Ile
         370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
             420                 425                 430

Gln Gly Gly Arg Trp Thr His Leu Arg Lys Pro Glu Asn Ser Glu Cys
         435                 440                 445

Asp Ala Thr Ala Lys Asn Lys Asn Glu Cys Ser Leu His Ile His Ala
         450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                 485                 490                 495

Ala Ile Ser Val Met Val Pro Asp Val Tyr Ile Ser Asp Asp Gly Gly
             500                 505                 510

Tyr Ser Trp Thr Lys Met Leu Glu Gly Pro His Tyr Tyr Thr Ile Leu
         515                 520                 525

Asp Ser Gly Gly Ile Ile Val Ala Ile Glu His Ser Ser Arg Pro Ile
         530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                 565                 570                 575

Gly Ala Arg Ser Met Asn Ile Ser Ile Trp Gly Phe Thr Glu Ser Phe
             580                 585                 590

Leu Thr Ser Gln Trp Val Ser Tyr Thr Ile Asp Phe Lys Asp Ile Leu
         595                 600                 605

Glu Arg Asn Cys Glu Glu Lys Asp Tyr Thr Ile Trp Leu Ala His Ser
         610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                 645                 650                 655

Tyr Val Val Thr Lys Gln Pro Ser Ile Cys Leu Cys Ser Leu Glu Asp
             660                 665                 670

Phe Leu Cys Asp Phe Gly Tyr Tyr Arg Pro Glu Asn Asp Ser Lys Cys
         675                 680                 685

Val Glu Gln Pro Glu Leu Lys Gly His Asp Leu Glu Phe Cys Leu Tyr
    690             695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Val Pro Ile Ile Leu Ala Ile Val Gly Leu Met Leu
        755                 760                 765

Val Thr Val Val Ala Gly Val Leu Ile Val Lys Lys Tyr Val Cys Gly
    770                 775                 780

Gly Arg Phe Leu Val His Arg Tyr Ser Val Leu Gln Gln His Ala Glu
785                 790                 795                 800

Ala Asn Gly Val Asp Gly Val Asp Ala Leu Asp Thr Ala Ser His Thr
                805                 810                 815

Asn Lys Ser Gly Tyr His Asp Asp Ser Asp Glu Asp Leu Leu Glu
            820                 825                 830

<210> SEQ ID NO 2
<211> LENGTH: 2214
<212> TYPE: PRT
<213> ORGANISM: Homo sapiens
<220> FEATURE:
<221> NAME/KEY: SIGNAL
<222> LOCATION: (1)..(28)
<223> OTHER INFORMATION: Signal peptide of SorLA
<220> FEATURE:
<221> NAME/KEY: PROPEP
<222> LOCATION: (29)..(81)
<223> OTHER INFORMATION: Propeptide of SorLA

<400> SEQUENCE: 2

Met Ala Thr Arg Ser Ser Arg Arg Glu Ser Arg Leu Pro Phe Leu Phe
1               5                   10                  15

Thr Leu Val Ala Leu Leu Pro Pro Gly Ala Leu Cys Glu Val Trp Thr
            20                  25                  30

Gln Arg Leu His Gly Gly Ser Ala Pro Leu Pro Gln Asp Arg Gly Phe
        35                  40                  45

Leu Val Val Gln Gly Asp Pro Arg Glu Leu Arg Leu Trp Ala Arg Gly
    50                  55                  60

Asp Ala Arg Gly Ala Ser Arg Ala Asp Glu Lys Pro Leu Arg Arg Lys
65                  70                  75                  80

Arg Ser Ala Ala Leu Gln Pro Glu Pro Ile Lys Val Tyr Gly Gln Val
                85                  90                  95

Ser Leu Asn Asp Ser His Asn Gln Met Val Val His Trp Ala Gly Glu
            100                 105                 110

Lys Ser Asn Val Ile Val Ala Leu Ala Arg Asp Ser Leu Ala Leu Ala
        115                 120                 125

Arg Pro Lys Ser Ser Asp Val Tyr Val Ser Tyr Asp Tyr Gly Lys Ser
    130                 135                 140

Phe Lys Lys Ile Ser Asp Lys Leu Asn Phe Gly Leu Gly Asn Arg Ser
145                 150                 155                 160

Glu Ala Val Ile Ala Gln Phe Tyr His Ser Pro Ala Asp Asn Lys Arg
                165                 170                 175

Tyr Ile Phe Ala Asp Ala Tyr Ala Gln Tyr Leu Trp Ile Thr Phe Asp
            180                 185                 190

-continued

```
Phe Cys Asn Thr Leu Gln Gly Phe Ser Ile Pro Phe Arg Ala Ala Asp
            195                 200                 205
Leu Leu Leu His Ser Lys Ala Ser Asn Leu Leu Leu Gly Phe Asp Arg
210                 215                 220
Ser His Pro Asn Lys Gln Leu Trp Lys Ser Asp Asp Phe Gly Gln Thr
225                 230                 235                 240
Trp Ile Met Ile Gln Glu His Val Lys Ser Phe Ser Trp Gly Ile Asp
            245                 250                 255
Pro Tyr Asp Lys Pro Asn Thr Ile Tyr Ile Glu Arg His Glu Pro Ser
            260                 265                 270
Gly Tyr Ser Thr Val Phe Arg Ser Thr Asp Phe Phe Gln Ser Arg Glu
            275                 280                 285
Asn Gln Glu Val Ile Leu Glu Glu Val Arg Asp Phe Gln Leu Arg Asp
290                 295                 300
Lys Tyr Met Phe Ala Thr Lys Val Val His Leu Leu Gly Ser Glu Gln
305                 310                 315                 320
Gln Ser Ser Val Gln Leu Trp Val Ser Phe Gly Arg Lys Pro Met Arg
            325                 330                 335
Ala Ala Gln Phe Val Thr Arg His Pro Ile Asn Glu Tyr Tyr Ile Ala
            340                 345                 350
Asp Ala Ser Glu Asp Gln Val Phe Val Cys Val Ser His Ser Asn Asn
            355                 360                 365
Arg Thr Asn Leu Tyr Ile Ser Glu Ala Glu Gly Leu Lys Phe Ser Leu
370                 375                 380
Ser Leu Glu Asn Val Leu Tyr Tyr Ser Pro Gly Gly Ala Gly Ser Asp
385                 390                 395                 400
Thr Leu Val Arg Tyr Phe Ala Asn Glu Pro Phe Ala Asp Phe His Arg
            405                 410                 415
Val Glu Gly Leu Gln Gly Val Tyr Ile Ala Thr Leu Ile Asn Gly Ser
            420                 425                 430
Met Asn Glu Glu Asn Met Arg Ser Val Ile Thr Phe Asp Lys Gly Gly
            435                 440                 445
Thr Trp Glu Phe Leu Gln Ala Pro Ala Phe Thr Gly Tyr Gly Glu Lys
            450                 455                 460
Ile Asn Cys Glu Leu Ser Gln Gly Cys Ser Leu His Leu Ala Gln Arg
465                 470                 475                 480
Leu Ser Gln Leu Leu Asn Leu Gln Leu Arg Arg Met Pro Ile Leu Ser
            485                 490                 495
Lys Glu Ser Ala Pro Gly Leu Ile Ile Ala Thr Gly Ser Val Gly Lys
            500                 505                 510
Asn Leu Ala Ser Lys Thr Asn Val Tyr Ile Ser Ser Ser Ala Gly Ala
            515                 520                 525
Arg Trp Arg Glu Ala Leu Pro Gly Pro His Tyr Tyr Thr Trp Gly Asp
530                 535                 540
His Gly Gly Ile Ile Thr Ala Ile Ala Gln Gly Met Glu Thr Asn Glu
545                 550                 555                 560
Leu Lys Tyr Ser Thr Asn Glu Gly Glu Thr Trp Lys Thr Phe Ile Phe
            565                 570                 575
Ser Glu Lys Pro Val Phe Val Tyr Gly Leu Leu Thr Glu Pro Gly Glu
            580                 585                 590
Lys Ser Thr Val Phe Thr Ile Phe Gly Ser Asn Lys Glu Asn Val His
            595                 600                 605
Ser Trp Leu Ile Leu Gln Val Asn Ala Thr Asp Ala Leu Gly Val Pro
610                 615                 620
```

```
Cys Thr Glu Asn Asp Tyr Lys Leu Trp Ser Pro Ser Asp Glu Arg Gly
625                 630                 635                 640

Asn Glu Cys Leu Leu Gly His Lys Thr Val Phe Lys Arg Arg Thr Pro
            645                 650                 655

His Ala Thr Cys Phe Asn Gly Glu Asp Phe Asp Arg Pro Val Val Val
                660                 665                 670

Ser Asn Cys Ser Cys Thr Arg Glu Asp Tyr Glu Cys Asp Phe Gly Phe
            675                 680                 685

Lys Met Ser Glu Asp Leu Ser Leu Glu Val Cys Val Pro Asp Pro Glu
690                 695                 700

Phe Ser Gly Lys Ser Tyr Ser Pro Val Pro Cys Pro Val Gly Ser
705                 710                 715                 720

Thr Tyr Arg Arg Thr Arg Gly Tyr Arg Lys Ile Ser Gly Asp Thr Cys
                725                 730                 735

Ser Gly Gly Asp Val Glu Ala Arg Leu Glu Gly Glu Leu Val Pro Cys
                740                 745                 750

Pro Leu Ala Glu Glu Asn Glu Phe Ile Leu Tyr Ala Val Arg Lys Ser
            755                 760                 765

Ile Tyr Arg Tyr Asp Leu Ala Ser Gly Ala Thr Glu Gln Leu Pro Leu
            770                 775                 780

Thr Gly Leu Arg Ala Ala Val Ala Leu Asp Phe Asp Tyr Glu His Asn
785                 790                 795                 800

Cys Leu Tyr Trp Ser Asp Leu Ala Leu Asp Val Ile Gln Arg Leu Cys
                805                 810                 815

Leu Asn Gly Ser Thr Gly Gln Glu Val Ile Ile Asn Ser Gly Leu Glu
                820                 825                 830

Thr Val Glu Ala Leu Ala Phe Glu Pro Leu Ser Gln Leu Leu Tyr Trp
            835                 840                 845

Val Asp Ala Gly Phe Lys Lys Ile Glu Val Ala Asn Pro Asp Gly Asp
850                 855                 860

Phe Arg Leu Thr Ile Val Asn Ser Ser Val Leu Asp Arg Pro Arg Ala
865                 870                 875                 880

Leu Val Leu Val Pro Gln Glu Gly Val Met Phe Trp Thr Asp Trp Gly
                885                 890                 895

Asp Leu Lys Pro Gly Ile Tyr Arg Ser Asn Met Asp Gly Ser Ala Ala
            900                 905                 910

Tyr His Leu Val Ser Glu Asp Val Lys Trp Pro Asn Gly Ile Ser Val
            915                 920                 925

Asp Asp Gln Trp Ile Tyr Trp Thr Asp Ala Tyr Leu Glu Cys Ile Glu
930                 935                 940

Arg Ile Thr Phe Ser Gly Gln Gln Arg Ser Val Ile Leu Asp Asn Leu
945                 950                 955                 960

Pro His Pro Tyr Ala Ile Ala Val Phe Lys Asn Glu Ile Tyr Trp Asp
            965                 970                 975

Asp Trp Ser Gln Leu Ser Ile Phe Arg Ala Ser Lys Tyr Ser Gly Ser
            980                 985                 990

Gln Met Glu Ile Leu Ala Asn Gln Leu Thr Gly Leu Met Asp Met Lys
            995                 1000                1005

Ile Phe Tyr Lys Gly Lys Asn  Thr Gly Ser Asn Ala  Cys Val Pro
            1010                1015                1020

Arg Pro Cys Ser Leu Leu Cys  Leu Pro Lys Ala Asn  Asn Ser Arg
            1025                1030                1035

Ser Cys Arg Cys Pro Glu Asp  Val Ser Ser Ser Val  Leu Pro Ser
```

```
                1040            1045            1050
Gly Asp Leu Met Cys Asp Cys Pro Gln Gly Tyr Gln Leu Lys Asn
    1055            1060            1065

Asn Thr Cys Val Lys Glu Glu Asn Thr Cys Leu Arg Asn Gln Tyr
    1070            1075            1080

Arg Cys Ser Asn Gly Asn Cys Ile Asn Ser Ile Trp Trp Cys Asp
    1085            1090            1095

Phe Asp Asn Asp Cys Gly Asp Met Ser Asp Glu Arg Asn Cys Pro
    1100            1105            1110

Thr Thr Ile Cys Asp Leu Asp Thr Gln Phe Arg Cys Gln Glu Ser
    1115            1120            1125

Gly Thr Cys Ile Pro Leu Ser Tyr Lys Cys Asp Leu Glu Asp Asp
    1130            1135            1140

Cys Gly Asp Asn Ser Asp Glu Ser His Cys Glu Met His Gln Cys
    1145            1150            1155

Arg Ser Asp Glu Tyr Asn Cys Ser Ser Gly Met Cys Ile Arg Ser
    1160            1165            1170

Ser Trp Val Cys Asp Gly Asp Asn Asp Cys Arg Asp Trp Ser Asp
    1175            1180            1185

Glu Ala Asn Cys Thr Ala Ile Tyr His Thr Cys Glu Ala Ser Asn
    1190            1195            1200

Phe Gln Cys Arg Asn Gly His Cys Ile Pro Gln Arg Trp Ala Cys
    1205            1210            1215

Asp Gly Asp Thr Asp Cys Gln Asp Gly Ser Asp Glu Asp Pro Val
    1220            1225            1230

Asn Cys Glu Lys Lys Cys Asn Gly Phe Arg Cys Pro Asn Gly Thr
    1235            1240            1245

Cys Ile Pro Ser Ser Lys His Cys Asp Gly Leu Arg Asp Cys Ser
    1250            1255            1260

Asp Gly Ser Asp Glu Gln His Cys Glu Pro Leu Cys Thr His Phe
    1265            1270            1275

Met Asp Phe Val Cys Lys Asn Arg Gln Gln Cys Leu Phe His Ser
    1280            1285            1290

Met Val Cys Asp Gly Ile Ile Gln Cys Arg Asp Gly Ser Asp Glu
    1295            1300            1305

Asp Ala Ala Phe Ala Gly Cys Ser Gln Asp Pro Glu Phe His Lys
    1310            1315            1320

Val Cys Asp Glu Phe Gly Phe Gln Cys Gln Asn Gly Val Cys Ile
    1325            1330            1335

Ser Leu Ile Trp Lys Cys Asp Gly Met Asp Asp Cys Gly Asp Tyr
    1340            1345            1350

Ser Asp Glu Ala Asn Cys Glu Asn Pro Thr Glu Ala Pro Asn Cys
    1355            1360            1365

Ser Arg Tyr Phe Gln Phe Arg Cys Glu Asn Gly His Cys Ile Pro
    1370            1375            1380

Asn Arg Trp Lys Cys Asp Arg Glu Asn Asp Cys Gly Asp Trp Ser
    1385            1390            1395

Asp Glu Lys Asp Cys Gly Asp Ser His Ile Leu Pro Phe Ser Thr
    1400            1405            1410

Pro Gly Pro Ser Thr Cys Leu Pro Asn Tyr Tyr Arg Cys Ser Ser
    1415            1420            1425

Gly Thr Cys Val Met Asp Thr Trp Val Cys Asp Gly Tyr Arg Asp
    1430            1435            1440
```

-continued

Cys Ala Asp Gly Ser Asp Glu Ala Cys Pro Leu Leu Ala Asn
1445                     1450                1455

Val Thr Ala Ala Ser Thr Pro Thr Gln Leu Gly Arg Cys Asp Arg
1460                     1465                1470

Phe Glu Phe Glu Cys His Gln Pro Lys Thr Cys Ile Pro Asn Trp
1475                     1480                1485

Lys Arg Cys Asp Gly His Gln Asp Cys Gln Asp Gly Arg Asp Glu
1490                     1495                1500

Ala Asn Cys Pro Thr His Ser Thr Leu Thr Cys Met Ser Arg Glu
1505                     1510                1515

Phe Gln Cys Glu Asp Gly Glu Ala Cys Ile Val Leu Ser Glu Arg
1520                     1525                1530

Cys Asp Gly Phe Leu Asp Cys Ser Asp Glu Ser Asp Glu Lys Ala
1535                     1540                1545

Cys Ser Asp Glu Leu Thr Val Tyr Lys Val Gln Asn Leu Gln Trp
1550                     1555                1560

Thr Ala Asp Phe Ser Gly Asp Val Thr Leu Thr Trp Met Arg Pro
1565                     1570                1575

Lys Lys Met Pro Ser Ala Ser Cys Val Tyr Asn Val Tyr Tyr Arg
1580                     1585                1590

Val Val Gly Glu Ser Ile Trp Lys Thr Leu Glu Thr His Ser Asn
1595                     1600                1605

Lys Thr Asn Thr Val Leu Lys Val Leu Lys Pro Asp Thr Thr Tyr
1610                     1615                1620

Gln Val Lys Val Gln Val Gln Cys Leu Ser Lys Ala His Asn Thr
1625                     1630                1635

Asn Asp Phe Val Thr Leu Arg Thr Pro Glu Gly Leu Pro Asp Ala
1640                     1645                1650

Pro Arg Asn Leu Gln Leu Ser Leu Pro Arg Glu Ala Glu Gly Val
1655                     1660                1665

Ile Val Gly His Trp Ala Pro Pro Ile His Thr His Gly Leu Ile
1670                     1675                1680

Arg Glu Tyr Ile Val Glu Tyr Ser Arg Ser Gly Ser Lys Met Trp
1685                     1690                1695

Ala Ser Gln Arg Ala Ala Ser Asn Phe Thr Glu Ile Lys Asn Leu
1700                     1705                1710

Leu Val Asn Thr Leu Tyr Thr Val Arg Val Ala Ala Val Thr Ser
1715                     1720                1725

Arg Gly Ile Gly Asn Trp Ser Asp Ser Lys Ser Ile Thr Thr Ile
1730                     1735                1740

Lys Gly Lys Val Ile Pro Pro Asp Ile His Ile Asp Ser Tyr
1745                     1750                1755

Gly Glu Asn Tyr Leu Ser Phe Thr Leu Thr Met Glu Ser Asp Ile
1760                     1765                1770

Lys Val Asn Gly Tyr Val Val Asn Leu Phe Trp Ala Phe Asp Thr
1775                     1780                1785

His Lys Gln Glu Arg Arg Thr Leu Asn Phe Arg Gly Ser Ile Leu
1790                     1795                1800

Ser His Lys Val Gly Asn Leu Thr Ala His Thr Ser Tyr Glu Ile
1805                     1810                1815

Ser Ala Trp Ala Lys Thr Asp Leu Gly Asp Ser Pro Leu Ala Phe
1820                     1825                1830

Glu His Val Met Thr Arg Gly Val Arg Pro Pro Ala Pro Ser Leu
1835                     1840                1845

Lys Ala Lys Ala Ile Asn Gln Thr Ala Val Glu Cys Thr Trp Thr
1850                1855                1860

Gly Pro Arg Asn Val Val Tyr Gly Ile Phe Tyr Ala Thr Ser Phe
1865                1870                1875

Leu Asp Leu Tyr Arg Asn Pro Lys Ser Leu Thr Thr Ser Leu His
1880                1885                1890

Asn Lys Thr Val Ile Val Ser Lys Asp Glu Gln Tyr Leu Phe Leu
1895                1900                1905

Val Arg Val Val Val Pro Tyr Gln Gly Pro Ser Ser Asp Tyr Val
1910                1915                1920

Val Val Lys Met Ile Pro Asp Ser Arg Leu Pro Pro Arg His Leu
1925                1930                1935

His Val Val His Thr Gly Lys Thr Ser Val Val Ile Lys Trp Glu
1940                1945                1950

Ser Pro Tyr Asp Ser Pro Gln Asp Leu Leu Tyr Ala Ile Ala
1955                1960                1965

Val Lys Asp Leu Ile Arg Lys Thr Asp Arg Ser Tyr Lys Val Lys
1970                1975                1980

Ser Arg Asn Ser Thr Val Glu Tyr Thr Leu Asn Lys Leu Glu Pro
1985                1990                1995

Gly Gly Lys Tyr His Ile Ile Val Gln Leu Gly Asn Met Ser Lys
2000                2005                2010

Asp Ser Ser Ile Lys Ile Thr Thr Val Ser Leu Ser Ala Pro Asp
2015                2020                2025

Ala Leu Lys Ile Ile Thr Glu Asn Asp His Val Leu Leu Phe Trp
2030                2035                2040

Lys Ser Leu Ala Leu Lys Glu Lys His Phe Asn Glu Ser Arg Gly
2045                2050                2055

Tyr Glu Ile His Met Phe Asp Ser Ala Met Asn Ile Thr Ala Tyr
2060                2065                2070

Leu Gly Asn Thr Thr Asp Asn Phe Phe Lys Ile Ser Asn Leu Lys
2075                2080                2085

Met Gly His Asn Tyr Thr Phe Thr Val Gln Ala Arg Cys Leu Phe
2090                2095                2100

Gly Asn Gln Ile Cys Gly Glu Pro Ala Ile Leu Leu Tyr Asp Glu
2105                2110                2115

Leu Gly Ser Gly Ala Asp Ala Ser Ala Thr Gln Ala Ala Arg Ser
2120                2125                2130

Thr Asp Val Ala Ala Val Val Val Pro Ile Leu Phe Leu Ile Leu
2135                2140                2145

Leu Ser Leu Gly Val Gly Phe Ala Ile Leu Tyr Thr Lys His Arg
2150                2155                2160

Arg Leu Gln Ser Ser Phe Thr Ala Phe Ala Asn Ser His Tyr Ser
2165                2170                2175

Ser Arg Leu Gly Ser Ala Ile Phe Ser Ser Gly Asp Asp Leu Gly
2180                2185                2190

Glu Asp Asp Glu Asp Ala Pro Met Ile Thr Gly Phe Ser Asp Asp
2195                2200                2205

Val Pro Met Val Ile Ala
2210

<210> SEQ ID NO 3
<211> LENGTH: 1168
<212> TYPE: PRT

<213> ORGANISM: Homo Sapiens
<220> FEATURE:
<221> NAME/KEY: MISC_FEATURE
<222> LOCATION: (1)..(1168)
<223> OTHER INFORMATION: SorCS1

<400> SEQUENCE: 3

Met Gly Lys Val Gly Ala Gly Gly Ser Gln Ala Arg Leu Ser Ala
1               5                   10                  15

Leu Leu Ala Gly Ala Gly Leu Leu Ile Leu Cys Ala Pro Gly Val Cys
                20                  25                  30

Gly Gly Gly Ser Cys Cys Pro Ser Pro His Pro Ser Ser Ala Pro Arg
                35              40                  45

Ser Ala Ser Thr Pro Arg Gly Phe Ser His Gln Gly Arg Pro Gly Arg
        50              55                  60

Ala Pro Ala Thr Pro Leu Pro Leu Val Val Arg Pro Leu Phe Ser Val
65                  70                  75                  80

Ala Pro Gly Asp Arg Ala Leu Ser Leu Glu Arg Ala Arg Gly Thr Gly
                85                  90                  95

Ala Ser Met Ala Val Ala Ala Arg Ser Gly Arg Arg Arg Ser Gly
                100                 105                 110

Ala Asp Gln Glu Lys Ala Glu Arg Gly Glu Gly Ala Ser Arg Ser Pro
        115                 120                 125

Arg Gly Val Leu Arg Asp Gly Gly Gln Gln Glu Pro Gly Thr Arg Glu
130                 135                 140

Arg Asp Pro Asp Lys Ala Thr Arg Phe Arg Met Glu Glu Leu Arg Leu
145                 150                 155                 160

Thr Ser Thr Thr Phe Ala Leu Thr Gly Asp Ser Ala His Asn Gln Ala
                165                 170                 175

Met Val His Trp Ser Gly His Asn Ser Ser Val Ile Leu Ile Leu Thr
                180                 185                 190

Lys Leu Tyr Asp Tyr Asn Leu Gly Ser Ile Thr Glu Ser Ser Leu Trp
        195                 200                 205

Arg Ser Thr Asp Tyr Gly Thr Thr Tyr Glu Lys Leu Asn Asp Lys Val
210                 215                 220

Gly Leu Lys Thr Ile Leu Gly Tyr Leu Tyr Val Cys Pro Thr Asn Lys
225                 230                 235                 240

Arg Lys Ile Met Leu Leu Thr Asp Pro Glu Ile Glu Ser Ser Leu Leu
                245                 250                 255

Ile Ser Ser Asp Glu Gly Ala Thr Tyr Gln Lys Tyr Arg Leu Asn Phe
        260                 265                 270

Tyr Ile Gln Ser Leu Leu Phe His Pro Lys Gln Glu Asp Trp Ile Leu
        275                 280                 285

Ala Tyr Ser Gln Asp Gln Lys Leu Tyr Ser Ser Ala Glu Phe Gly Arg
        290                 295                 300

Arg Trp Gln Leu Ile Gln Glu Gly Val Val Pro Asn Arg Phe Tyr Trp
305                 310                 315                 320

Ser Val Met Gly Ser Asn Lys Glu Pro Asp Leu Val His Leu Glu Ala
                325                 330                 335

Arg Thr Val Asp Gly His Ser His Tyr Leu Thr Cys Arg Met Gln Asn
                340                 345                 350

Cys Thr Glu Ala Asn Arg Asn Gln Pro Phe Pro Gly Tyr Ile Asp Pro
        355                 360                 365

Asp Ser Leu Ile Val Gln Asp His Tyr Val Phe Val Gln Leu Thr Ser
        370                 375                 380

```
Gly Gly Arg Pro His Tyr Tyr Val Ser Tyr Arg Arg Asn Ala Phe Ala
385                 390                 395                 400

Gln Met Lys Leu Pro Lys Tyr Ala Leu Pro Lys Asp Met His Val Ile
            405                 410                 415

Ser Thr Asp Glu Asn Gln Val Phe Ala Ala Val Gln Glu Trp Asn Gln
        420                 425                 430

Asn Asp Thr Tyr Asn Leu Tyr Ile Ser Asp Thr Arg Gly Val Tyr Phe
        435                 440                 445

Thr Leu Ala Leu Glu Asn Val Gln Ser Ser Arg Gly Pro Glu Gly Asn
    450                 455                 460

Ile Met Ile Asp Leu Tyr Glu Val Ala Gly Ile Lys Gly Met Phe Leu
465                 470                 475                 480

Ala Asn Lys Lys Ile Asp Tyr Gln Val Lys Thr Phe Ile Thr Tyr Asn
            485                 490                 495

Lys Gly Arg Asp Trp Arg Leu Leu Gln Ala Pro Asp Thr Asp Leu Arg
            500                 505                 510

Gly Asp Pro Val His Cys Leu Pro Tyr Cys Ser Leu His Leu His
    515                 520                 525

Leu Lys Val Ser Glu Asn Pro Tyr Thr Ser Gly Ile Ile Ala Ser Lys
530                 535                 540

Asp Thr Ala Pro Ser Ile Ile Val Ala Ser Gly Asn Ile Gly Ser Glu
545                 550                 555                 560

Leu Ser Asp Thr Asp Ile Ser Met Phe Val Ser Ser Asp Ala Gly Asn
            565                 570                 575

Thr Trp Arg Gln Ile Phe Glu Glu His Ser Val Leu Tyr Leu Asp
            580                 585                 590

Gln Gly Gly Val Leu Val Ala Met Lys His Thr Ser Leu Pro Ile Arg
    595                 600                 605

His Leu Trp Leu Ser Phe Asp Glu Gly Arg Ser Trp Ser Lys Tyr Ser
    610                 615                 620

Phe Thr Ser Ile Pro Leu Phe Val Asp Gly Val Leu Gly Glu Pro Gly
625                 630                 635                 640

Glu Glu Thr Leu Ile Met Thr Val Phe Gly His Phe Ser His Arg Ser
            645                 650                 655

Glu Trp Gln Leu Val Lys Val Asp Tyr Lys Ser Ile Phe Asp Arg Arg
        660                 665                 670

Cys Ala Glu Glu Asp Tyr Arg Pro Trp Gln Leu His Ser Gln Gly Glu
        675                 680                 685

Ala Cys Ile Met Gly Ala Lys Arg Ile Tyr Lys Lys Arg Lys Ser Glu
        690                 695                 700

Arg Lys Cys Met Gln Gly Lys Tyr Ala Gly Ala Met Glu Ser Glu Pro
705                 710                 715                 720

Cys Val Cys Thr Glu Ala Asp Phe Asp Cys Asp Tyr Gly Tyr Glu Arg
            725                 730                 735

His Ser Asn Gly Gln Cys Leu Pro Ala Phe Trp Phe Asn Pro Ser Ser
            740                 745                 750

Leu Ser Lys Asp Cys Ser Leu Gly Gln Ser Tyr Leu Asn Ser Thr Gly
            755                 760                 765

Tyr Arg Lys Val Val Ser Asn Asn Cys Thr Asp Gly Val Arg Glu Gln
770                 775                 780

Tyr Thr Ala Lys Pro Gln Lys Cys Pro Gly Lys Ala Pro Arg Gly Leu
785                 790                 795                 800

Arg Ile Val Thr Ala Asp Gly Lys Leu Thr Ala Glu Gln Gly His Asn
            805                 810                 815
```

```
Val Thr Leu Met Val Gln Leu Glu Glu Gly Asp Val Gln Arg Thr Leu
            820                 825                 830

Ile Gln Val Asp Phe Gly Asp Gly Ile Ala Val Ser Tyr Val Asn Leu
            835                 840                 845

Ser Ser Met Glu Asp Gly Ile Lys His Val Tyr Gln Asn Val Gly Ile
    850                 855                 860

Phe Arg Val Thr Val Gln Val Asp Asn Ser Leu Gly Ser Asp Ser Ala
865                 870                 875                 880

Val Leu Tyr Leu His Val Thr Cys Pro Leu Glu His Val His Leu Ser
                885                 890                 895

Leu Pro Phe Val Thr Thr Lys Asn Lys Glu Val Asn Ala Thr Ala Val
            900                 905                 910

Leu Trp Pro Ser Gln Val Gly Thr Leu Thr Tyr Val Trp Trp Tyr Gly
            915                 920                 925

Asn Asn Thr Glu Pro Leu Ile Thr Leu Glu Gly Ser Ile Ser Phe Arg
930                 935                 940

Phe Thr Ser Glu Gly Met Asn Thr Ile Thr Val Gln Val Ser Ala Gly
945                 950                 955                 960

Asn Ala Ile Leu Gln Asp Thr Lys Thr Ile Ala Val Tyr Glu Glu Phe
                965                 970                 975

Arg Ser Leu Arg Leu Ser Phe Ser Pro Asn Leu Asp Asp Tyr Asn Pro
            980                 985                 990

Asp Ile Pro Glu Trp Arg Arg Asp Ile Gly Arg Val Ile Lys Lys Ser
            995                 1000                1005

Leu Val Glu Ala Thr Gly Val Pro Gly Gln His Ile Leu Val Ala
    1010                1015                1020

Val Leu Pro Gly Leu Pro Thr Thr Ala Glu Leu Phe Val Leu Pro
    1025                1030                1035

Tyr Gln Asp Pro Ala Gly Glu Asn Lys Arg Ser Thr Asp Asp Leu
    1040                1045                1050

Glu Gln Ile Ser Glu Leu Leu Ile His Thr Leu Asn Gln Asn Ser
    1055                1060                1065

Val His Phe Glu Leu Lys Pro Gly Val Arg Val Leu Val His Ala
    1070                1075                1080

Ala His Leu Thr Ala Ala Pro Leu Val Asp Leu Thr Pro Thr His
    1085                1090                1095

Ser Gly Ser Ala Met Leu Met Leu Leu Ser Val Val Phe Val Gly
    1100                1105                1110

Leu Ala Val Phe Val Ile Tyr Lys Phe Lys Arg Arg Val Ala Leu
    1115                1120                1125

Pro Ser Pro Pro Ser Pro Ser Thr Gln Pro Gly Asp Ser Ser Leu
    1130                1135                1140

Arg Leu Gln Arg Ala Arg His Ala Thr Pro Pro Ser Thr Pro Lys
    1145                1150                1155

Arg Gly Ser Ala Gly Ala Gln Tyr Ala Ile
    1160                1165

<210> SEQ ID NO 4
<211> LENGTH: 907
<212> TYPE: PRT
<213> ORGANISM: Homo Sapiens
<220> FEATURE:
<221> NAME/KEY: MISC_FEATURE
<222> LOCATION: (1)..(907)
<223> OTHER INFORMATION: SorCS2
```

-continued

```
<400> SEQUENCE: 4

Leu Ile Phe His Pro Lys Glu Glu Asp Lys Val Leu Ala Tyr Thr Lys
1               5                   10                  15

Glu Ser Lys Leu Tyr Val Ser Ser Asp Leu Gly Lys Lys Trp Thr Leu
            20                  25                  30

Leu Gln Glu Arg Val Thr Lys Asp His Val Phe Trp Ser Val Ser Gly
        35                  40                  45

Val Asp Ala Asp Pro Asp Leu Val His Val Glu Ala Gln Asp Leu Gly
    50                  55                  60

Gly Asp Phe Arg Tyr Val Thr Cys Ala Ile His Asn Cys Ser Glu Lys
65                  70                  75                  80

Met Leu Thr Ala Pro Phe Ala Gly Pro Ile Asp His Gly Ser Leu Thr
                85                  90                  95

Val Gln Asp Asp Tyr Ile Phe Phe Lys Ala Thr Ser Ala Asn Gln Thr
            100                 105                 110

Lys Tyr Tyr Val Ser Tyr Arg Arg Asn Glu Phe Val Leu Met Lys Leu
        115                 120                 125

Pro Lys Tyr Ala Leu Pro Lys Asp Leu Gln Ile Ile Ser Thr Asp Glu
    130                 135                 140

Ser Gln Val Phe Val Ala Val Gln Glu Trp Tyr Gln Met Asp Thr Tyr
145                 150                 155                 160

Asn Leu Tyr Gln Ser Asp Pro Arg Gly Val Arg Tyr Ala Leu Val Leu
                165                 170                 175

Gln Asp Val Arg Ser Ser Arg Gln Ala Glu Glu Ser Val Leu Ile Asp
            180                 185                 190

Ile Leu Glu Val Arg Gly Val Lys Gly Val Phe Leu Ala Asn Gln Lys
        195                 200                 205

Ile Asp Gly Lys Val Met Thr Leu Ile Thr Tyr Asn Lys Gly Arg Asp
    210                 215                 220

Trp Asp Tyr Leu Arg Pro Pro Ser Met Asp Met Asn Gly Lys Pro Thr
225                 230                 235                 240

Asn Cys Lys Pro Pro Asp Cys His Leu His Leu His Leu Arg Trp Ala
                245                 250                 255

Asp Asn Pro Tyr Val Ser Gly Thr Val His Thr Lys Asp Thr Ala Pro
            260                 265                 270

Gly Leu Ile Met Gly Ala Gly Asn Leu Gly Ser Gln Leu Val Glu Tyr
        275                 280                 285

Lys Glu Glu Met Tyr Ile Thr Ser Asp Cys Gly His Thr Trp Arg Gln
    290                 295                 300

Val Phe Glu Glu Glu His His Ile Leu Tyr Leu Asp His Gly Gly Val
305                 310                 315                 320

Ile Val Ala Ile Lys Asp Thr Ser Ile Pro Leu Lys Ile Leu Lys Phe
                325                 330                 335

Ser Val Asp Glu Gly Leu Thr Trp Ser Thr His Asn Phe Thr Ser Thr
            340                 345                 350

Ser Val Phe Val Asp Gly Leu Leu Ser Glu Pro Gly Asp Glu Thr Leu
        355                 360                 365

Val Met Thr Val Phe Gly His Ile Ser Phe Arg Ser Asp Trp Glu Leu
    370                 375                 380

Val Lys Val Asp Phe Arg Pro Ser Phe Ser Arg Gln Cys Gly Glu Glu
385                 390                 395                 400

Asp Tyr Ser Ser Trp Glu Leu Ser Asn Leu Gln Gly Asp Arg Cys Ile
                405                 410                 415
```

```
Met Gly Gln Gln Arg Ser Phe Arg Lys Arg Lys Ser Thr Ser Trp Cys
            420                 425                 430

Ile Lys Gly Arg Ser Phe Thr Ser Ala Leu Thr Ser Arg Val Cys Glu
            435                 440                 445

Cys Arg Asp Ser Asp Phe Leu Cys Asp Tyr Gly Phe Glu Arg Ser Pro
            450                 455                 460

Ser Ser Glu Ser Ser Thr Asn Lys Cys Ser Ala Asn Phe Trp Phe Asn
465                 470                 475                 480

Pro Leu Ser Pro Asp Asp Cys Ala Leu Gly Gln Thr Tyr Thr Ser
                485                 490                 495

Ser Leu Gly Tyr Arg Lys Val Val Ser Asn Val Cys Glu Gly Val
            500                 505                 510

Asp Met Gln Gln Ser Gln Val Gln Leu Gln Cys Pro Leu Thr Pro Pro
            515                 520                 525

Arg Gly Leu Gln Val Ser Ile Gln Gly Glu Ala Val Ala Val Arg Pro
            530                 535                 540

Gly Glu Asp Val Leu Phe Val Val Arg Gln Glu Gln Gly Asp Val Leu
545                 550                 555                 560

Thr Thr Lys Tyr Gln Val Asp Leu Gly Asp Gly Phe Lys Ala Met Tyr
            565                 570                 575

Val Asn Leu Thr Leu Thr Gly Glu Pro Ile Arg His Arg Tyr Glu Ser
            580                 585                 590

Pro Gly Ile Tyr Arg Val Ser Val Arg Ala Glu Asn Thr Ala Gly His
            595                 600                 605

Asp Glu Ala Val Leu Phe Val Gln Val Asn Ser Pro Leu Gln Ala Leu
            610                 615                 620

Tyr Leu Glu Val Val Pro Val Ile Gly Leu Asn Gln Glu Val Asn Leu
625                 630                 635                 640

Thr Ala Val Leu Leu Pro Leu Asn Pro Asn Leu Thr Val Phe Tyr Trp
            645                 650                 655

Trp Ile Gly His Ser Leu Gln Pro Leu Leu Ser Leu Asp Asn Ser Val
            660                 665                 670

Thr Thr Arg Phe Ser Asp Thr Gly Asp Val Arg Val Thr Val Gln Ala
            675                 680                 685

Ala Cys Gly Asn Ser Val Leu Gln Asp Ser Arg Val Leu Arg Val Leu
            690                 695                 700

Asp Gln Phe Gln Val Met Pro Leu Gln Phe Ser Lys Glu Leu Asp Ala
705                 710                 715                 720

Tyr Asn Pro Asn Thr Pro Glu Trp Arg Glu Asp Val Gly Leu Val Val
            725                 730                 735

Thr Arg Leu Leu Ser Lys Glu Thr Ser Val Pro Gln Glu Leu Leu Val
            740                 745                 750

Thr Val Val Lys Pro Gly Leu Pro Thr Leu Ala Asp Leu Tyr Val Leu
            755                 760                 765

Leu Pro Pro Pro Arg Pro Thr Arg Lys Arg Ser Leu Ser Ser Asp Lys
            770                 775                 780

Arg Leu Ala Ala Ile Gln Gln Val Leu Asn Ala Gln Lys Ile Ser Phe
785                 790                 795                 800

Leu Leu Arg Gly Gly Val Arg Val Leu Ala Leu Arg Asp Thr Gly
            805                 810                 815

Thr Gly Ala Glu Gln Leu Gly Gly Gly Gly Tyr Trp Ala Val Val
            820                 825                 830

Val Leu Phe Val Ile Gly Leu Phe Ala Ala Gly Ala Phe Ile Leu Tyr
            835                 840                 845
```

```
Lys Phe Lys Arg Lys Arg Pro Gly Arg Thr Val Tyr Ala Gln Met His
    850                 855                 860
Asn Glu Lys Glu Gln Glu Met Thr Ser Pro Val Ser His Ser Glu Asp
865                 870                 875                 880
Val Gln Gly Ala Val Gln Gly Asn His Ser Gly Val Val Leu Ser Ile
                885                 890                 895
Asn Ser Arg Glu Met His Ser Tyr Leu Val Ser
            900                 905
```

<210> SEQ ID NO 5
<211> LENGTH: 1222
<212> TYPE: PRT
<213> ORGANISM: Homo Sapiens
<220> FEATURE:
<221> NAME/KEY: MISC_FEATURE
<222> LOCATION: (1)..(1222)
<223> OTHER INFORMATION: SorCS3

<400> SEQUENCE: 5

```
Met Glu Ala Ala Arg Thr Glu Arg Pro Ala Gly Arg Pro Gly Ala Pro
1               5                   10                  15
Leu Val Arg Thr Gly Leu Leu Leu Ser Thr Trp Val Leu Ala Gly
            20                  25                  30
Ala Glu Ile Thr Trp Asp Ala Thr Gly Gly Pro Gly Arg Pro Ala Ala
        35                  40                  45
Pro Ala Ser Arg Pro Pro Ala Leu Ser Pro Leu Ser Pro Arg Ala Val
    50                  55                  60
Ala Ser Gln Trp Pro Glu Glu Leu Ala Ser Ala Arg Arg Ala Ala Val
65                  70                  75                  80
Leu Gly Arg Arg Ala Gly Pro Glu Leu Leu Pro Gln Gln Gly Gly Gly
                85                  90                  95
Arg Gly Gly Glu Met Gln Val Glu Ala Gly Gly Thr Ser Pro Ala Gly
            100                 105                 110
Glu Arg Arg Gly Arg Gly Ile Pro Ala Pro Ala Lys Leu Gly Gly Ala
        115                 120                 125
Arg Arg Ser Arg Arg Ala Gln Pro Pro Ile Thr Gln Glu Arg Gly Asp
    130                 135                 140
Ala Trp Ala Thr Ala Pro Ala Asp Gly Ser Arg Gly Ser Arg Pro Leu
145                 150                 155                 160
Ala Lys Gly Ser Arg Glu Glu Val Lys Ala Pro Arg Ala Gly Gly Ser
                165                 170                 175
Ala Ala Glu Asp Leu Arg Leu Pro Ser Thr Ser Phe Ala Leu Thr Gly
            180                 185                 190
Asp Ser Ala His Asn Gln Ala Met Val His Trp Ser Gly His Asn Ser
        195                 200                 205
Ser Val Ile Leu Ile Leu Thr Lys Leu Tyr Asp Phe Asn Leu Gly Ser
    210                 215                 220
Val Thr Glu Ser Ser Leu Trp Arg Ser Thr Asp Tyr Gly Thr Thr Tyr
225                 230                 235                 240
Glu Lys Leu Asn Asp Lys Val Gly Leu Lys Thr Val Leu Ser Tyr Leu
                245                 250                 255
Tyr Val Asn Pro Thr Asn Lys Arg Lys Ile Met Leu Leu Ser Asp Pro
            260                 265                 270
Glu Met Glu Ser Ser Ile Leu Ile Ser Ser Asp Glu Gly Ala Thr Tyr
        275                 280                 285
Gln Lys Tyr Arg Leu Thr Phe Tyr Ile Gln Ser Leu Leu Phe His Pro
```

```
                290                 295                 300
Lys Gln Glu Asp Trp Val Leu Ala Tyr Ser Leu Asp Gln Lys Leu Tyr
305                 310                 315                 320

Ser Ser Met Asp Phe Gly Arg Arg Trp Gln Leu Met His Glu Arg Ile
                325                 330                 335

Thr Pro Asn Arg Phe Tyr Trp Ser Val Ala Gly Leu Asp Lys Glu Ala
                340                 345                 350

Asp Leu Val His Met Glu Val Arg Thr Thr Asp Gly Tyr Ala His Tyr
                355                 360                 365

Leu Thr Cys Arg Ile Gln Glu Cys Ala Glu Thr Thr Arg Ser Gly Pro
370                 375                 380

Phe Ala Arg Ser Ile Asp Ile Ser Ser Leu Val Val Gln Asp Glu Tyr
385                 390                 395                 400

Ile Phe Ile Gln Val Thr Thr Ser Gly Arg Ala Ser Tyr Tyr Val Ser
                405                 410                 415

Tyr Arg Arg Glu Ala Phe Ala Gln Ile Lys Leu Pro Lys Tyr Ser Leu
                420                 425                 430

Pro Lys Asp Met His Ile Ile Ser Thr Asp Glu Asn Gln Val Phe Ala
                435                 440                 445

Ala Val Gln Glu Trp Asn Gln Asn Asp Thr Tyr Asn Leu Tyr Ile Ser
450                 455                 460

Asp Thr Arg Gly Ile Tyr Phe Thr Leu Ala Met Glu Asn Ile Lys Ser
465                 470                 475                 480

Ser Arg Gly Leu Met Gly Asn Ile Ile Ile Glu Leu Tyr Glu Val Ala
                485                 490                 495

Gly Ile Lys Gly Ile Phe Leu Ala Asn Lys Lys Val Asp Asp Gln Val
                500                 505                 510

Lys Thr Tyr Ile Thr Tyr Asn Lys Gly Arg Asp Trp Arg Leu Leu Gln
                515                 520                 525

Ala Pro Asp Val Asp Leu Arg Gly Ser Pro Val His Cys Leu Leu Pro
530                 535                 540

Phe Cys Ser Leu His Leu His Leu Gln Leu Ser Glu Asn Pro Tyr Ser
545                 550                 555                 560

Ser Gly Arg Ile Ser Ser Lys Glu Thr Ala Pro Gly Leu Val Val Ala
                565                 570                 575

Thr Gly Asn Ile Gly Pro Glu Leu Ser Tyr Thr Asp Ile Gly Val Phe
                580                 585                 590

Ile Ser Ser Asp Gly Gly Asn Thr Trp Arg Gln Ile Phe Asp Glu Glu
                595                 600                 605

Tyr Asn Val Trp Phe Leu Asp Trp Gly Gly Ala Leu Val Ala Met Lys
                610                 615                 620

His Thr Pro Leu Pro Val Arg His Leu Trp Val Ser Phe Asp Glu Gly
625                 630                 635                 640

His Ser Trp Asp Lys Tyr Gly Phe Thr Ser Val Pro Leu Phe Val Asp
                645                 650                 655

Gly Ala Leu Val Glu Ala Gly Met Glu Thr His Ile Met Thr Val Phe
                660                 665                 670

Gly His Phe Ser Leu Arg Ser Glu Trp Gln Leu Val Lys Val Asp Tyr
                675                 680                 685

Lys Ser Ile Phe Ser Arg His Cys Thr Lys Glu Asp Tyr Gln Thr Trp
                690                 695                 700

His Leu Leu Asn Gln Gly Glu Pro Cys Val Met Gly Glu Arg Lys Ile
705                 710                 715                 720
```

-continued

```
Phe Lys Lys Arg Lys Pro Gly Ala Gln Cys Ala Leu Gly Arg Asp His
            725                 730                 735

Ser Gly Ser Val Val Ser Glu Pro Cys Val Cys Ala Asn Trp Asp Phe
        740                 745                 750

Glu Cys Asp Tyr Gly Tyr Glu Arg His Gly Glu Ser Gln Cys Val Pro
    755                 760                 765

Ala Phe Trp Tyr Asn Pro Ala Ser Pro Ser Lys Asp Cys Ser Leu Gly
770                 775                 780

Gln Ser Tyr Leu Asn Ser Thr Gly Tyr Arg Arg Ile Val Ser Asn Asn
785                 790                 795                 800

Cys Thr Asp Gly Leu Arg Glu Lys Tyr Thr Ala Lys Ala Gln Met Cys
                805                 810                 815

Pro Gly Lys Ala Pro Arg Gly Leu His Val Val Thr Thr Asp Gly Arg
            820                 825                 830

Leu Val Ala Glu Gln Gly His Asn Ala Thr Phe Ile Ile Leu Met Glu
        835                 840                 845

Glu Gly Asp Leu Gln Arg Thr Asn Ile Gln Leu Asp Phe Gly Asp Gly
    850                 855                 860

Ile Ala Val Ser Tyr Ala Asn Phe Ser Pro Ile Glu Asp Gly Ile Lys
865                 870                 875                 880

His Val Tyr Lys Ser Ala Gly Ile Phe Gln Val Thr Ala Tyr Ala Glu
                885                 890                 895

Asn Asn Leu Gly Ser Asp Thr Ala Val Leu Phe Leu His Val Val Cys
            900                 905                 910

Pro Val Glu His Val His Leu Arg Val Pro Phe Val Ala Ile Arg Asn
        915                 920                 925

Lys Glu Val Asn Ile Ser Ala Val Val Trp Pro Ser Gln Leu Gly Thr
    930                 935                 940

Leu Thr Tyr Phe Trp Trp Phe Gly Asn Ser Thr Lys Pro Leu Ile Thr
945                 950                 955                 960

Leu Asp Ser Ser Ile Ser Phe Thr Phe Leu Ala Glu Gly Thr Asp Thr
                965                 970                 975

Ile Thr Val Gln Val Ala Ala Gly Asn Ala Leu Ile Gln Asp Thr Lys
            980                 985                 990

Glu Ile Ala Val His Glu Tyr Phe  Gln Ser Gln Leu Leu  Ser Phe Ser
        995                 1000                1005

Pro Asn  Leu Asp Tyr His Asn  Pro Asp Ile Pro Glu  Trp Arg Lys
    1010                1015                1020

Asp Ile  Gly Asn Val Ile Lys  Arg Ala Leu Val Lys  Val Thr Ser
    1025                1030                1035

Val Pro  Glu Asp Gln Ile Leu  Ile Ala Val Phe Pro  Gly Leu Pro
    1040                1045                1050

Thr Ser  Ala Glu Leu Phe Ile  Leu Pro Pro Lys Asn  Leu Thr Glu
    1055                1060                1065

Arg Arg  Lys Gly Asn Glu Gly  Asp Leu Glu Gln Ile  Val Glu Thr
    1070                1075                1080

Leu Phe  Asn Ala Leu Asn Gln  Asn Leu Val Gln Phe  Glu Leu Lys
    1085                1090                1095

Pro Gly  Val Gln Val Ile Val  Tyr Val Thr Gln Leu  Thr Leu Ala
    1100                1105                1110

Pro Leu  Val Asp Ser Ser Ala  Gly His Ser Ser Ser  Ala Met Leu
    1115                1120                1125

Met Leu  Leu Ser Val Val Phe  Val Gly Leu Ala Val  Phe Leu Ile
    1130                1135                1140
```

-continued

```
Tyr Lys Phe Lys Arg Lys Ile Pro Trp Ile Asn Ile Tyr Ala Gln
    1145                1150                1155

Val Gln His Asp Lys Glu Gln Glu Met Ile Gly Ser Val Ser Gln
    1160                1165                1170

Ser Glu Asn Ala Pro Lys Ile Thr Leu Ser Asp Phe Thr Glu Pro
    1175                1180                1185

Glu Glu Leu Leu Asp Lys Glu Leu Asp Thr Arg Val Ile Gly Gly
    1190                1195                1200

Ile Ala Thr Ile Ala Asn Ser Glu Ser Thr Lys Glu Ile Pro Asn
    1205                1210                1215

Cys Thr Ser Val
    1220

<210> SEQ ID NO 6
<211> LENGTH: 839
<212> TYPE: PRT
<213> ORGANISM: Homo sapiens
<220> FEATURE:
<221> NAME/KEY: MISC_FEATURE
<222> LOCATION: (1)..(839)
<223> OTHER INFORMATION: TrpV1

<400> SEQUENCE: 6

Met Lys Lys Trp Ser Ser Thr Asp Leu Gly Ala Ala Ala Asp Pro Leu
1               5                   10                  15

Gln Lys Asp Thr Cys Pro Asp Pro Leu Asp Gly Asp Pro Asn Ser Arg
                20                  25                  30

Pro Pro Pro Ala Lys Pro Gln Leu Ser Thr Ala Lys Ser Arg Thr Arg
            35                  40                  45

Leu Phe Gly Lys Gly Asp Ser Glu Glu Ala Phe Pro Val Asp Cys Pro
        50                  55                  60

His Glu Glu Gly Glu Leu Asp Ser Cys Pro Thr Ile Thr Val Ser Pro
65                  70                  75                  80

Val Ile Thr Ile Gln Arg Pro Gly Asp Gly Pro Thr Gly Ala Arg Leu
                85                  90                  95

Leu Ser Gln Asp Ser Val Ala Ala Ser Thr Glu Lys Thr Leu Arg Leu
            100                 105                 110

Tyr Asp Arg Arg Ser Ile Phe Glu Ala Val Ala Gln Asn Asn Cys Gln
        115                 120                 125

Asp Leu Glu Ser Leu Leu Leu Phe Leu Gln Lys Ser Lys Lys His Leu
    130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
            180                 185                 190

Ala Ser Tyr Thr Asp Ser Tyr Tyr Lys Gly Gln Thr Ala Leu His Ile
        195                 200                 205

Ala Ile Glu Arg Arg Asn Met Ala Leu Val Thr Leu Leu Val Glu Asn
    210                 215                 220

Gly Ala Asp Val Gln Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
```

```
              260                 265                 270
Trp Gln Thr Ala Asp Ile Ser Ala Arg Asp Ser Val Gly Asn Thr Val
        275                 280                 285

Leu His Ala Leu Val Glu Val Ala Asp Asn Thr Ala Asp Asn Thr Lys
        290                 295                 300

Phe Val Thr Ser Met Tyr Asn Glu Ile Leu Ile Leu Gly Ala Lys Leu
305                 310                 315                 320

His Pro Thr Leu Lys Leu Glu Glu Leu Thr Asn Lys Lys Gly Met Thr
                    325                 330                 335

Pro Leu Ala Leu Ala Ala Gly Thr Gly Lys Ile Gly Val Leu Ala Tyr
                340                 345                 350

Ile Leu Gln Arg Glu Ile Gln Glu Pro Glu Cys Arg His Leu Ser Arg
                355                 360                 365

Lys Phe Thr Glu Trp Ala Tyr Gly Pro Val His Ser Ser Leu Tyr Asp
        370                 375                 380

Leu Ser Cys Ile Asp Thr Cys Glu Lys Asn Ser Val Leu Glu Val Ile
385                 390                 395                 400

Ala Tyr Ser Ser Ser Glu Thr Pro Asn Arg His Asp Met Leu Leu Val
                    405                 410                 415

Glu Pro Leu Asn Arg Leu Leu Gln Asp Lys Trp Asp Arg Phe Val Lys
                420                 425                 430

Arg Ile Phe Tyr Phe Asn Phe Leu Val Tyr Cys Leu Tyr Met Ile Ile
                435                 440                 445

Phe Thr Met Ala Ala Tyr Tyr Arg Pro Val Asp Gly Leu Pro Pro Phe
        450                 455                 460

Lys Met Glu Lys Thr Gly Asp Tyr Phe Arg Val Thr Gly Glu Ile Leu
465                 470                 475                 480

Ser Val Leu Gly Gly Val Tyr Phe Phe Phe Arg Gly Ile Gln Tyr Phe
                    485                 490                 495

Leu Gln Arg Arg Pro Ser Met Lys Thr Leu Phe Val Asp Ser Tyr Ser
                500                 505                 510

Glu Met Leu Phe Phe Leu Gln Ser Leu Phe Met Leu Ala Thr Val Val
                515                 520                 525

Leu Tyr Phe Ser His Leu Lys Glu Tyr Val Ala Ser Met Val Phe Ser
        530                 535                 540

Leu Ala Leu Gly Trp Thr Asn Met Leu Tyr Tyr Thr Arg Gly Phe Gln
545                 550                 555                 560

Gln Met Gly Ile Tyr Ala Val Met Ile Glu Lys Met Ile Leu Arg Asp
                    565                 570                 575

Leu Cys Arg Phe Met Phe Val Tyr Ile Val Phe Leu Phe Gly Phe Ser
                580                 585                 590

Thr Ala Val Val Thr Leu Ile Glu Asp Gly Lys Asn Asp Ser Leu Pro
                595                 600                 605

Ser Glu Ser Thr Ser His Arg Trp Arg Gly Pro Ala Cys Arg Pro Pro
        610                 615                 620

Asp Ser Ser Tyr Asn Ser Leu Tyr Ser Thr Cys Leu Glu Leu Phe Lys
625                 630                 635                 640

Phe Thr Ile Gly Met Gly Asp Leu Glu Phe Thr Glu Asn Tyr Asp Phe
                    645                 650                 655

Lys Ala Val Phe Ile Ile Leu Leu Leu Ala Tyr Val Ile Leu Thr Tyr
                660                 665                 670

Ile Leu Leu Leu Asn Met Leu Ile Ala Leu Met Gly Glu Thr Val Asn
                675                 680                 685
```

```
Lys Ile Ala Gln Glu Ser Lys Asn Ile Trp Lys Leu Gln Arg Ala Ile
        690             695                 700
Thr Ile Leu Asp Thr Glu Lys Ser Phe Leu Lys Cys Met Arg Lys Ala
705             710                 715                 720
Phe Arg Ser Gly Lys Leu Leu Gln Val Gly Tyr Thr Pro Asp Gly Lys
                725                 730                 735
Asp Asp Tyr Arg Trp Cys Phe Arg Val Asp Glu Val Asn Trp Thr Thr
            740                 745                 750
Trp Asn Thr Asn Val Gly Ile Ile Asn Glu Asp Pro Gly Asn Cys Glu
        755                 760                 765
Gly Val Lys Arg Thr Leu Ser Phe Ser Leu Arg Ser Arg Val Ser
770                 775                 780
Gly Arg His Trp Lys Asn Phe Ala Leu Val Pro Leu Leu Arg Glu Ala
785                 790                 795                 800
Ser Ala Arg Asp Arg Gln Ser Ala Gln Pro Glu Glu Val Tyr Leu Arg
                805                 810                 815
Gln Phe Ser Gly Ser Leu Lys Pro Glu Asp Ala Glu Val Phe Lys Ser
                820                 825                 830
Pro Ala Ala Ser Gly Glu Lys
            835
```

<210> SEQ ID NO 7
<211> LENGTH: 764
<212> TYPE: PRT
<213> ORGANISM: Homo sapiens
<220> FEATURE:
<221> NAME/KEY: MISC_FEATURE
<222> LOCATION: (1)..(764)
<223> OTHER INFORMATION: TrpV2

<400> SEQUENCE: 7

```
Met Thr Ser Pro Ser Ser Ser Pro Val Phe Arg Leu Glu Thr Leu Asp
1               5                   10                  15
Gly Gly Gln Glu Asp Gly Ser Glu Ala Asp Arg Gly Lys Leu Asp Phe
            20                  25                  30
Gly Ser Gly Leu Pro Pro Met Glu Ser Gln Phe Gln Gly Glu Asp Arg
        35                  40                  45
Lys Phe Ala Pro Gln Ile Arg Val Asn Leu Asn Tyr Arg Lys Gly Thr
50                  55                  60
Gly Ala Ser Gln Pro Asp Pro Asn Arg Phe Asp Arg Asp Arg Leu Phe
65                  70                  75                  80
Asn Ala Val Ser Arg Gly Val Pro Glu Asp Leu Ala Gly Leu Pro Glu
                85                  90                  95
Tyr Leu Ser Lys Thr Ser Lys Tyr Leu Thr Asp Ser Glu Tyr Thr Glu
            100                 105                 110
Gly Ser Thr Gly Lys Thr Cys Leu Met Lys Ala Val Leu Asn Leu Lys
        115                 120                 125
Asp Gly Val Asn Ala Cys Ile Leu Pro Leu Leu Gln Ile Asp Arg Asp
130                 135                 140
Ser Gly Asn Pro Gln Pro Leu Val Asn Ala Gln Cys Thr Asp Asp Tyr
145                 150                 155                 160
Tyr Arg Gly His Ser Ala Leu His Ile Ala Ile Glu Lys Arg Ser Leu
                165                 170                 175
Gln Cys Val Lys Leu Leu Val Glu Asn Gly Ala Asn Val His Ala Arg
            180                 185                 190
Ala Cys Gly Arg Phe Phe Gln Lys Gly Gln Gly Thr Cys Phe Tyr Phe
        195                 200                 205
```

```
Gly Glu Leu Pro Leu Ser Leu Ala Ala Cys Thr Lys Gln Trp Asp Val
    210                 215                 220
Val Ser Tyr Leu Leu Glu Asn Pro His Gln Pro Ala Ser Leu Gln Ala
225                 230                 235                 240
Thr Asp Ser Gln Gly Asn Thr Val Leu His Ala Leu Val Met Ile Ser
                245                 250                 255
Asp Asn Ser Ala Glu Asn Ile Ala Leu Val Thr Ser Met Tyr Asp Gly
                260                 265                 270
Leu Leu Gln Ala Gly Ala Arg Leu Cys Pro Thr Val Gln Leu Glu Asp
            275                 280                 285
Ile Arg Asn Leu Gln Asp Leu Thr Pro Leu Lys Leu Ala Ala Lys Glu
        290                 295                 300
Gly Lys Ile Glu Ile Phe Arg His Ile Leu Gln Arg Glu Phe Ser Gly
305                 310                 315                 320
Leu Ser His Leu Ser Arg Lys Phe Thr Glu Trp Cys Tyr Gly Pro Val
                325                 330                 335
Arg Val Ser Leu Tyr Asp Leu Ala Ser Val Asp Ser Cys Glu Glu Asn
                340                 345                 350
Ser Val Leu Glu Ile Ile Ala Phe His Cys Lys Ser Pro His Arg His
            355                 360                 365
Arg Met Val Val Leu Glu Pro Leu Asn Lys Leu Leu Gln Ala Lys Trp
        370                 375                 380
Asp Leu Leu Ile Pro Lys Phe Phe Leu Asn Phe Leu Cys Asn Leu Ile
385                 390                 395                 400
Tyr Met Phe Ile Phe Thr Ala Val Ala Tyr His Gln Pro Thr Leu Lys
                405                 410                 415
Lys Gln Ala Ala Pro His Leu Lys Ala Glu Val Gly Asn Ser Met Leu
            420                 425                 430
Leu Thr Gly His Ile Leu Ile Leu Leu Gly Gly Ile Tyr Leu Leu Val
        435                 440                 445
Gly Gln Leu Trp Tyr Phe Trp Arg Arg His Val Phe Ile Trp Ile Ser
    450                 455                 460
Phe Ile Asp Ser Tyr Phe Glu Ile Leu Phe Leu Phe Gln Ala Leu Leu
465                 470                 475                 480
Thr Val Val Ser Gln Val Leu Cys Phe Leu Ala Ile Glu Trp Tyr Leu
                485                 490                 495
Pro Leu Leu Val Ser Ala Leu Val Leu Gly Trp Leu Asn Leu Leu Tyr
            500                 505                 510
Tyr Thr Arg Gly Phe Gln His Thr Gly Ile Tyr Ser Val Met Ile Gln
        515                 520                 525
Lys Val Ile Leu Arg Asp Leu Leu Arg Phe Leu Leu Ile Tyr Leu Val
    530                 535                 540
Phe Leu Phe Gly Phe Ala Val Ala Leu Val Ser Leu Ser Gln Glu Ala
545                 550                 555                 560
Trp Arg Pro Glu Ala Pro Thr Gly Pro Asn Ala Thr Glu Ser Val Gln
                565                 570                 575
Pro Met Glu Gly Gln Glu Asp Glu Gly Asn Gly Ala Gln Tyr Arg Gly
            580                 585                 590
Ile Leu Glu Ala Ser Leu Glu Leu Phe Lys Phe Thr Ile Gly Met Gly
        595                 600                 605
Glu Leu Ala Phe Gln Glu Gln Leu His Phe Arg Gly Met Val Leu Leu
    610                 615                 620
Leu Leu Leu Ala Tyr Val Leu Leu Thr Tyr Ile Leu Leu Leu Asn Met
```

```
625                 630                 635                 640
Leu Ile Ala Leu Met Ser Glu Thr Val Asn Ser Val Ala Thr Asp Ser
                    645                 650                 655

Trp Ser Ile Trp Lys Leu Gln Lys Ala Ile Ser Val Leu Glu Met Glu
                660                 665                 670

Asn Gly Tyr Trp Trp Cys Arg Lys Lys Gln Arg Ala Gly Val Met Leu
            675                 680                 685

Thr Val Gly Thr Lys Pro Asp Gly Ser Pro Asp Glu Arg Trp Cys Phe
        690                 695                 700

Arg Val Glu Glu Val Asn Trp Ala Ser Trp Glu Gln Thr Leu Pro Thr
705                 710                 715                 720

Leu Cys Glu Asp Pro Ser Gly Ala Gly Val Pro Arg Thr Leu Glu Asn
                725                 730                 735

Pro Val Leu Ala Ser Pro Pro Lys Glu Asp Glu Asp Gly Ala Ser Glu
                740                 745                 750

Glu Asn Tyr Val Pro Val Gln Leu Leu Gln Ser Asn
            755                 760

<210> SEQ ID NO 8
<211> LENGTH: 790
<212> TYPE: PRT
<213> ORGANISM: Homo sapiens
<220> FEATURE:
<221> NAME/KEY: MISC_FEATURE
<222> LOCATION: (1)..(790)
<223> OTHER INFORMATION: TrpV3

<400> SEQUENCE: 8

Met Lys Ala His Pro Lys Glu Met Val Pro Leu Met Gly Lys Arg Val
1               5                   10                  15

Ala Ala Pro Ser Gly Asn Pro Ala Ile Leu Pro Glu Lys Arg Pro Ala
                20                  25                  30

Glu Ile Thr Pro Thr Lys Lys Ser Ala His Phe Phe Leu Glu Ile Glu
            35                  40                  45

Gly Phe Glu Pro Asn Pro Thr Val Ala Lys Thr Ser Pro Pro Val Phe
        50                  55                  60

Ser Lys Pro Met Asp Ser Asn Ile Arg Gln Cys Ile Ser Gly Asn Cys
65                  70                  75                  80

Asp Asp Met Asp Ser Pro Gln Ser Pro Gln Asp Val Thr Glu Thr
                85                  90                  95

Pro Ser Asn Pro Asn Ser Pro Ala Gln Leu Ala Lys Glu Glu Gln
                100                 105                 110

Arg Arg Lys Lys Arg Arg Leu Lys Lys Arg Ile Phe Ala Ala Val Ser
        115                 120                 125

Glu Gly Cys Val Glu Glu Leu Val Glu Leu Leu Val Glu Leu Gln Glu
    130                 135                 140

Leu Cys Arg Arg Arg His Asp Glu Asp Val Pro Asp Phe Leu Met His
145                 150                 155                 160

Lys Leu Thr Ala Ser Asp Thr Gly Lys Thr Cys Leu Met Lys Ala Leu
                165                 170                 175

Leu Asn Ile Asn Pro Asn Thr Lys Glu Ile Val Arg Ile Leu Leu Ala
            180                 185                 190

Phe Ala Glu Glu Asn Asp Ile Leu Gly Arg Phe Ile Asn Ala Glu Tyr
        195                 200                 205

Thr Glu Glu Ala Tyr Glu Gly Gln Thr Ala Leu Asn Ile Ala Ile Glu
    210                 215                 220
```

-continued

Arg Arg Gln Gly Asp Ile Ala Ala Leu Leu Ile Ala Ala Gly Ala Asp
225                 230                 235                 240

Val Asn Ala His Ala Lys Gly Ala Phe Phe Asn Pro Lys Tyr Gln His
            245                 250                 255

Glu Gly Phe Tyr Phe Gly Glu Thr Pro Leu Ala Leu Ala Ala Cys Thr
                260                 265                 270

Asn Gln Pro Glu Ile Val Gln Leu Leu Met Glu His Glu Gln Thr Asp
        275                 280                 285

Ile Thr Ser Arg Asp Ser Arg Gly Asn Asn Ile Leu His Ala Leu Val
        290                 295                 300

Thr Val Ala Glu Asp Phe Lys Thr Gln Asn Asp Phe Val Lys Arg Met
305                 310                 315                 320

Tyr Asp Met Ile Leu Leu Arg Ser Gly Asn Trp Glu Leu Glu Thr Thr
                325                 330                 335

Arg Asn Asn Asp Gly Leu Thr Pro Leu Gln Leu Ala Ala Lys Met Gly
            340                 345                 350

Lys Ala Glu Ile Leu Lys Tyr Ile Leu Ser Arg Glu Ile Lys Glu Lys
        355                 360                 365

Arg Leu Arg Ser Leu Ser Arg Lys Phe Thr Asp Trp Ala Tyr Gly Pro
370                 375                 380

Val Ser Ser Ser Leu Tyr Asp Leu Thr Asn Val Asp Thr Thr Thr Asp
385                 390                 395                 400

Asn Ser Val Leu Glu Ile Thr Val Tyr Asn Thr Asn Ile Asp Asn Arg
                405                 410                 415

His Glu Met Leu Thr Leu Glu Pro Leu His Thr Leu Leu His Met Lys
            420                 425                 430

Trp Lys Lys Phe Ala Lys His Met Phe Phe Leu Ser Phe Cys Phe Tyr
        435                 440                 445

Phe Phe Tyr Asn Ile Thr Leu Thr Leu Val Ser Tyr Tyr Arg Pro Arg
450                 455                 460

Glu Glu Glu Ala Ile Pro His Pro Leu Ala Leu Thr His Lys Met Gly
465                 470                 475                 480

Trp Leu Gln Leu Leu Gly Arg Met Phe Val Leu Ile Trp Ala Met Cys
                485                 490                 495

Ile Ser Val Lys Glu Gly Ile Ala Ile Phe Leu Leu Arg Pro Ser Asp
            500                 505                 510

Leu Gln Ser Ile Leu Ser Asp Ala Trp Phe His Phe Val Phe Phe Ile
        515                 520                 525

Gln Ala Val Leu Val Ile Leu Ser Val Phe Leu Tyr Leu Phe Ala Tyr
    530                 535                 540

Lys Glu Tyr Leu Ala Cys Leu Val Leu Ala Met Ala Leu Gly Trp Ala
545                 550                 555                 560

Asn Met Leu Tyr Tyr Thr Arg Gly Phe Gln Ser Met Gly Met Tyr Ser
                565                 570                 575

Val Met Ile Gln Lys Val Ile Leu His Asp Val Leu Lys Phe Leu Phe
            580                 585                 590

Val Tyr Ile Val Phe Leu Leu Gly Phe Gly Val Ala Leu Ala Ser Leu
        595                 600                 605

Ile Glu Lys Cys Pro Lys Asp Asn Lys Asp Cys Ser Ser Tyr Gly Ser
    610                 615                 620

Phe Ser Asp Ala Val Leu Glu Leu Phe Lys Leu Thr Ile Gly Leu Gly
625                 630                 635                 640

Asp Leu Asn Ile Gln Gln Asn Ser Lys Tyr Pro Ile Leu Phe Leu Phe
                645                 650                 655

```
Leu Leu Ile Thr Tyr Val Ile Leu Thr Phe Val Leu Leu Asn Met
            660                 665                 670
Leu Ile Ala Leu Met Gly Glu Thr Val Glu Asn Val Ser Lys Glu Ser
            675                 680                 685
Glu Arg Ile Trp Arg Leu Gln Arg Ala Arg Thr Ile Leu Glu Phe Glu
            690                 695                 700
Lys Met Leu Pro Glu Trp Leu Arg Ser Arg Phe Arg Met Gly Glu Leu
705                 710                 715                 720
Cys Lys Val Ala Glu Asp Phe Arg Leu Cys Leu Arg Ile Asn Glu
            725                 730                 735
Val Lys Trp Thr Glu Trp Lys Thr His Val Ser Phe Leu Asn Glu Asp
            740                 745                 750
Pro Gly Pro Val Arg Arg Thr Asp Phe Asn Lys Ile Gln Asp Ser Ser
            755                 760                 765
Arg Asn Asn Ser Lys Thr Thr Leu Asn Ala Phe Glu Glu Val Glu Glu
            770                 775                 780
Phe Pro Glu Thr Ser Val
785                 790

<210> SEQ ID NO 9
<211> LENGTH: 871
<212> TYPE: PRT
<213> ORGANISM: Homo sapiens
<220> FEATURE:
<221> NAME/KEY: MISC_FEATURE
<222> LOCATION: (1)..(871)
<223> OTHER INFORMATION: TrpV4

<400> SEQUENCE: 9

Met Ala Asp Ser Ser Glu Gly Pro Arg Ala Gly Pro Gly Glu Val Ala
1               5                   10                  15
Glu Leu Pro Gly Asp Glu Ser Gly Thr Pro Gly Gly Glu Ala Phe Pro
            20                  25                  30
Leu Ser Ser Leu Ala Asn Leu Phe Glu Gly Glu Asp Gly Ser Leu Ser
            35                  40                  45
Pro Ser Pro Ala Asp Ala Ser Arg Pro Ala Gly Pro Gly Asp Gly Arg
        50                  55                  60
Pro Asn Leu Arg Met Lys Phe Gln Gly Ala Phe Arg Lys Gly Val Pro
65              70                  75                  80
Asn Pro Ile Asp Leu Leu Glu Ser Thr Leu Tyr Glu Ser Ser Val Val
            85                  90                  95
Pro Gly Pro Lys Lys Ala Pro Met Asp Ser Leu Phe Asp Tyr Gly Thr
            100                 105                 110
Tyr Arg His His Ser Ser Asp Asn Lys Arg Trp Arg Lys Lys Ile Ile
            115                 120                 125
Glu Lys Gln Pro Gln Ser Pro Lys Ala Pro Ala Pro Gln Pro Pro Pro
        130                 135                 140
Ile Leu Lys Val Phe Asn Arg Pro Ile Leu Phe Asp Ile Val Ser Arg
145                 150                 155                 160
Gly Ser Thr Ala Asp Leu Asp Gly Leu Leu Pro Phe Leu Leu Thr His
            165                 170                 175
Lys Lys Arg Leu Thr Asp Glu Glu Phe Arg Glu Pro Ser Thr Gly Lys
            180                 185                 190
Thr Cys Leu Pro Lys Ala Leu Leu Asn Leu Ser Asn Gly Arg Asn Asp
            195                 200                 205
Thr Ile Pro Val Leu Leu Asp Ile Ala Glu Arg Thr Gly Asn Met Arg
```

-continued

```
            210                 215                 220
Glu Phe Ile Asn Ser Pro Phe Arg Asp Ile Tyr Tyr Arg Gly Gln Thr
225                 230                 235                 240

Ala Leu His Ile Ala Ile Glu Arg Arg Cys Lys His Tyr Val Glu Leu
                245                 250                 255

Leu Val Ala Gln Gly Ala Asp Val His Ala Gln Ala Arg Gly Arg Phe
                260                 265                 270

Phe Gln Pro Lys Asp Glu Gly Gly Tyr Phe Tyr Phe Gly Glu Leu Pro
                275                 280                 285

Leu Ser Leu Ala Ala Cys Thr Asn Gln Pro His Ile Val Asn Tyr Leu
290                 295                 300

Thr Glu Asn Pro His Lys Lys Ala Asp Met Arg Arg Gln Asp Ser Arg
305                 310                 315                 320

Gly Asn Thr Val Leu His Ala Leu Val Ala Ile Ala Asp Asn Thr Arg
                325                 330                 335

Glu Asn Thr Lys Phe Val Thr Lys Met Tyr Asp Leu Leu Leu Leu Lys
                340                 345                 350

Cys Ala Arg Leu Phe Pro Asp Ser Asn Leu Glu Ala Val Leu Asn Asn
                355                 360                 365

Asp Gly Leu Ser Pro Leu Met Met Ala Ala Lys Thr Gly Lys Ile Gly
370                 375                 380

Ile Phe Gln His Ile Ile Arg Arg Glu Val Thr Asp Glu Asp Thr Arg
385                 390                 395                 400

His Leu Ser Arg Lys Phe Lys Asp Trp Ala Tyr Gly Pro Val Tyr Ser
                405                 410                 415

Ser Leu Tyr Asp Leu Ser Ser Leu Asp Thr Cys Gly Glu Glu Ala Ser
                420                 425                 430

Val Leu Glu Ile Leu Val Tyr Asn Ser Lys Ile Glu Asn Arg His Glu
                435                 440                 445

Met Leu Ala Val Glu Pro Ile Asn Glu Leu Leu Arg Asp Lys Trp Arg
450                 455                 460

Lys Phe Gly Ala Val Ser Phe Tyr Ile Asn Val Val Ser Tyr Leu Cys
465                 470                 475                 480

Ala Met Val Ile Phe Thr Leu Thr Ala Tyr Tyr Gln Pro Leu Glu Gly
                485                 490                 495

Thr Pro Pro Tyr Pro Tyr Arg Thr Thr Val Asp Tyr Leu Arg Leu Ala
                500                 505                 510

Gly Glu Val Ile Thr Leu Phe Thr Gly Val Leu Phe Phe Phe Thr Asn
                515                 520                 525

Ile Lys Asp Leu Phe Met Lys Lys Cys Pro Gly Val Asn Ser Leu Phe
530                 535                 540

Ile Asp Gly Ser Phe Gln Leu Leu Tyr Phe Ile Tyr Ser Val Leu Val
545                 550                 555                 560

Ile Val Ser Ala Ala Leu Tyr Leu Ala Gly Ile Glu Ala Tyr Leu Ala
                565                 570                 575

Val Met Val Phe Ala Leu Val Leu Gly Trp Met Asn Ala Leu Tyr Phe
                580                 585                 590

Thr Arg Gly Leu Lys Leu Thr Gly Thr Tyr Ser Ile Met Ile Gln Lys
                595                 600                 605

Ile Leu Phe Lys Asp Leu Phe Arg Phe Leu Leu Val Tyr Leu Leu Phe
610                 615                 620

Met Ile Gly Tyr Ala Ser Ala Leu Val Ser Leu Leu Asn Pro Cys Ala
625                 630                 635                 640
```

```
Asn Met Lys Val Cys Asn Glu Asp Gln Thr Asn Cys Thr Val Pro Thr
            645                 650                 655

Tyr Pro Ser Cys Arg Asp Ser Glu Thr Phe Ser Thr Phe Leu Leu Asp
            660                 665                 670

Leu Phe Lys Leu Thr Ile Gly Met Gly Asp Leu Glu Met Leu Ser Ser
            675                 680                 685

Thr Lys Tyr Pro Val Val Phe Ile Ile Leu Leu Val Thr Tyr Ile Ile
            690                 695                 700

Leu Thr Phe Val Leu Leu Leu Asn Met Leu Ile Ala Leu Met Gly Glu
705                     710                 715                 720

Thr Val Gly Gln Val Ser Lys Glu Ser Lys His Ile Trp Lys Leu Gln
                725                 730                 735

Trp Ala Thr Thr Ile Leu Asp Ile Glu Arg Ser Phe Pro Val Phe Leu
            740                 745                 750

Arg Lys Ala Phe Arg Ser Gly Glu Met Val Thr Val Gly Lys Ser Ser
            755                 760                 765

Asp Gly Thr Pro Asp Arg Arg Trp Cys Phe Arg Val Asp Glu Val Asn
            770                 775                 780

Trp Ser His Trp Asn Gln Asn Leu Gly Ile Ile Asn Glu Asp Pro Gly
785                 790                 795                 800

Lys Asn Glu Thr Tyr Gln Tyr Tyr Gly Phe Ser His Thr Val Gly Arg
                805                 810                 815

Leu Arg Arg Asp Arg Trp Ser Ser Val Val Pro Arg Val Val Glu Leu
            820                 825                 830

Asn Lys Asn Ser Asn Pro Asp Glu Val Val Val Pro Leu Asp Ser Met
            835                 840                 845

Gly Asn Pro Arg Cys Asp Gly His Gln Gln Gly Tyr Pro Arg Lys Trp
            850                 855                 860

Arg Thr Asp Asp Ala Pro Leu
865                 870

<210> SEQ ID NO 10
<211> LENGTH: 796
<212> TYPE: PRT
<213> ORGANISM: Homo sapiens
<220> FEATURE:
<221> NAME/KEY: MISC_FEATURE
<222> LOCATION: (1)..(796)
<223> OTHER INFORMATION: TrkA

<400> SEQUENCE: 10

Met Leu Arg Gly Gly Arg Arg Gly Gln Leu Gly Trp His Ser Trp Ala
1               5                   10                  15

Ala Gly Pro Gly Ser Leu Leu Ala Trp Leu Ile Leu Ala Ser Ala Gly
            20                  25                  30

Ala Ala Pro Cys Pro Asp Ala Cys Cys Pro His Gly Ser Ser Gly Leu
            35                  40                  45

Arg Cys Thr Arg Asp Gly Ala Leu Asp Ser Leu His His Leu Pro Gly
            50                  55                  60

Ala Glu Asn Leu Thr Glu Leu Tyr Ile Glu Asn Gln Gln His Leu Gln
65                  70                  75                  80

His Leu Glu Leu Arg Asp Leu Arg Gly Leu Gly Glu Leu Arg Asn Leu
                85                  90                  95

Thr Ile Val Lys Ser Gly Leu Arg Phe Val Ala Pro Asp Ala Phe His
            100                 105                 110

Phe Thr Pro Arg Leu Ser Arg Leu Asn Leu Ser Phe Asn Ala Leu Glu
            115                 120                 125
```

-continued

Ser Leu Ser Trp Lys Thr Val Gln Gly Leu Ser Leu Gln Glu Leu Val
    130                 135                 140

Leu Ser Gly Asn Pro Leu His Cys Ser Cys Ala Leu Arg Trp Leu Gln
145                 150                 155                 160

Arg Trp Glu Glu Glu Gly Leu Gly Gly Val Pro Glu Gln Lys Leu Gln
                165                 170                 175

Cys His Gly Gln Gly Pro Leu Ala His Met Pro Asn Ala Ser Cys Gly
            180                 185                 190

Val Pro Thr Leu Lys Val Gln Val Pro Asn Ala Ser Val Asp Val Gly
        195                 200                 205

Asp Asp Val Leu Leu Arg Cys Gln Val Glu Gly Arg Gly Leu Glu Gln
    210                 215                 220

Ala Gly Trp Ile Leu Thr Glu Leu Glu Gln Ser Ala Thr Val Met Lys
225                 230                 235                 240

Ser Gly Gly Leu Pro Ser Leu Gly Leu Thr Leu Ala Asn Val Thr Ser
                245                 250                 255

Asp Leu Asn Arg Lys Asn Val Thr Cys Trp Ala Glu Asn Asp Val Gly
            260                 265                 270

Arg Ala Glu Val Ser Val Gln Val Asn Val Ser Phe Pro Ala Ser Val
        275                 280                 285

Gln Leu His Thr Ala Val Glu Met His His Trp Cys Ile Pro Phe Ser
    290                 295                 300

Val Asp Gly Gln Pro Ala Pro Ser Leu Arg Trp Leu Phe Asn Gly Ser
305                 310                 315                 320

Val Leu Asn Glu Thr Ser Phe Ile Phe Thr Glu Phe Leu Glu Pro Ala
                325                 330                 335

Ala Asn Glu Thr Val Arg His Gly Cys Leu Arg Leu Asn Gln Pro Thr
            340                 345                 350

His Val Asn Asn Gly Asn Tyr Thr Leu Leu Ala Ala Asn Pro Phe Gly
        355                 360                 365

Gln Ala Ser Ala Ser Ile Met Ala Ala Phe Met Asp Asn Pro Phe Glu
    370                 375                 380

Phe Asn Pro Glu Asp Pro Ile Pro Val Ser Phe Ser Pro Val Asp Thr
385                 390                 395                 400

Asn Ser Thr Ser Gly Asp Pro Val Glu Lys Lys Asp Glu Thr Pro Phe
                405                 410                 415

Gly Val Ser Val Ala Val Gly Leu Ala Val Phe Ala Cys Leu Phe Leu
            420                 425                 430

Ser Thr Leu Leu Leu Val Leu Asn Lys Cys Gly Arg Arg Asn Lys Phe
    435                 440                 445

Gly Ile Asn Arg Pro Ala Val Leu Ala Pro Glu Asp Gly Leu Ala Met
450                 455                 460

Ser Leu His Phe Met Thr Leu Gly Gly Ser Ser Leu Ser Pro Thr Glu
465                 470                 475                 480

Gly Lys Gly Ser Gly Leu Gln Gly His Ile Ile Glu Asn Pro Gln Tyr
                485                 490                 495

Phe Ser Asp Ala Cys Val His His Ile Lys Arg Arg Asp Ile Val Leu
            500                 505                 510

Lys Trp Glu Leu Gly Glu Gly Ala Phe Gly Lys Val Phe Leu Ala Glu
        515                 520                 525

Cys His Asn Leu Leu Pro Glu Gln Asp Lys Met Leu Val Ala Val Lys
    530                 535                 540

Ala Leu Lys Glu Ala Ser Glu Ser Ala Arg Gln Asp Phe Gln Arg Glu

-continued

```
            545                 550                 555                 560
        Ala Glu Leu Leu Thr Met Leu Gln His Gln His Ile Val Arg Phe Phe
                        565                 570                 575
        Gly Val Cys Thr Glu Gly Arg Pro Leu Leu Met Val Phe Glu Tyr Met
                        580                 585                 590
        Arg His Gly Asp Leu Asn Arg Phe Leu Arg Ser His Gly Pro Asp Ala
                        595                 600                 605
        Lys Leu Leu Ala Gly Gly Glu Asp Val Ala Pro Gly Pro Leu Gly Leu
                        610                 615                 620
        Gly Gln Leu Leu Ala Val Ala Ser Gln Val Ala Ala Gly Met Val Tyr
        625                 630                 635                 640
        Leu Ala Gly Leu His Phe Val His Arg Asp Leu Ala Thr Arg Asn Cys
                        645                 650                 655
        Leu Val Gly Gln Gly Leu Val Val Lys Ile Gly Asp Phe Gly Met Ser
                        660                 665                 670
        Arg Asp Ile Tyr Ser Thr Asp Tyr Tyr Arg Val Gly Gly Arg Thr Met
                        675                 680                 685
        Leu Pro Ile Arg Trp Met Pro Pro Glu Ser Ile Leu Tyr Arg Lys Phe
                        690                 695                 700
        Thr Thr Glu Ser Asp Val Trp Ser Phe Gly Val Val Leu Trp Glu Ile
        705                 710                 715                 720
        Phe Thr Tyr Gly Lys Gln Pro Trp Tyr Gln Leu Ser Asn Thr Glu Ala
                        725                 730                 735
        Ile Asp Cys Ile Thr Gln Gly Arg Glu Leu Glu Arg Pro Arg Ala Cys
                        740                 745                 750
        Pro Pro Glu Val Tyr Ala Ile Met Arg Gly Cys Trp Gln Arg Glu Pro
                        755                 760                 765
        Gln Gln Arg His Ser Ile Lys Asp Val His Ala Arg Leu Gln Ala Leu
                        770                 775                 780
        Ala Gln Ala Pro Pro Val Tyr Leu Asp Val Leu Gly
        785                 790                 795
```